(12) United States Patent
Wu et al.

(10) Patent No.: US 10,780,164 B2
(45) Date of Patent: Sep. 22, 2020

(54) MULTIFUNCTIONAL NANOPARTICLE COMPOSITIONS AND USES THEREOF

(71) Applicants: THE GOVERNING COUNCIL OF THE UNIVERSITY OF TORONTO, Toronto (CA); UNIVERSITY HEALTH NETWORK, Toronto (CA)

(72) Inventors: Xiaoyu Wu, Toronto (CA); Claudia Regina Gordijo, Toronto (CA); Azhar Z. Abbasi, Toronto (CA); Preethy Prasad, Toronto (CA); Ralph Dacosta, Toronto (CA); Azusa Maeda, Toronto (CA); Mohammad Ali Amini, Toronto (CA)

(73) Assignees: THE GOVERNING COUNCIL OF THE UNIVERSITY OF TORONTO, Toronto (CA); UNIVERSITY HEALTH NETWORK, Toronto (CA)

( * ) Notice: Subject to any disclaimer, the term of this patent is extended or adjusted under 35 U.S.C. 154(b) by 218 days.

(21) Appl. No.: 15/301,682

(22) PCT Filed: Apr. 7, 2015

(86) PCT No.: PCT/CA2015/050277
§ 371 (c)(1),
(2) Date: Oct. 3, 2016

(87) PCT Pub. No.: WO2015/149188
PCT Pub. Date: Oct. 8, 2015

(65) Prior Publication Data
US 2017/0252440 A1    Sep. 7, 2017

Related U.S. Application Data

(60) Provisional application No. 61/974,878, filed on Apr. 3, 2014.

(51) Int. Cl.
*A61K 41/00*    (2020.01)
*A61N 5/10*    (2006.01)
(Continued)

(52) U.S. Cl.
CPC ........ *A61K 41/0038* (2013.01); *A61K 9/0019* (2013.01); *A61K 9/14* (2013.01);
(Continued)

(58) Field of Classification Search
CPC .............. A61K 41/0038; A61K 9/5146; A61K 9/5149; A61K 51/1241; A61K 51/1244;
(Continued)

(56) References Cited

U.S. PATENT DOCUMENTS

| | | | |
|---|---|---|---|
| 8,702,645 B2 | 4/2014 | Wu et al. | |
| 2003/0129130 A1* | 7/2003 | Guire | A61K 9/2081 424/1.11 |

(Continued)

FOREIGN PATENT DOCUMENTS

WO    WO2013/127004    9/2013

OTHER PUBLICATIONS

Rockwell, S. et al. (2009) Hypoxia and Radiation Therapy: Past History, Ongoing Research, and Future Promise. Curr. Mol. Med. 9: 442-458.
(Continued)

*Primary Examiner* — Carrie R Dorna
(74) *Attorney, Agent, or Firm* — Eduardo Krupnik

(57) ABSTRACT

Disclosed herein are multifunctional nanoparticle compositions. The compositions can be useful for the treatment of cancer by enhancing the anti-tumor effectiveness of radiation directed to a tissue, cell or a tumor and the methods of use thereof. The multifunctional nanoparticle composition comprises a metal oxide nanoparticle core; a functional
(Continued)

coating on the surface of the metal oxide nanoparticle core; and a matrix carrier in which the coated nanoparticle is embedded.

16 Claims, 42 Drawing Sheets

(51) Int. Cl.
  A61K 9/14      (2006.01)
  C01G 45/02     (2006.01)
  A61K 9/00      (2006.01)
  A61K 9/51      (2006.01)
  A61K 33/32     (2006.01)
  A61K 47/32     (2006.01)
  A61K 47/34     (2017.01)
  A61K 47/42     (2017.01)

(52) U.S. Cl.
  CPC .......... *A61K 9/5146* (2013.01); *A61K 33/32* (2013.01); *A61K 47/32* (2013.01); *A61K 47/34* (2013.01); *A61K 47/42* (2013.01); *A61N 5/1001* (2013.01); *C01G 45/02* (2013.01); *A61K 9/5169* (2013.01); *A61N 5/10* (2013.01); *A61N 2005/1021* (2013.01); *A61N 2005/1098* (2013.01); *C01P 2002/72* (2013.01); *C01P 2002/84* (2013.01); *C01P 2004/04* (2013.01); *C01P 2004/24* (2013.01); *C01P 2004/64* (2013.01); *C01P 2006/22* (2013.01)

(58) Field of Classification Search
  CPC .............. A61K 51/1282; A61N 5/1001; A61N 2005/1019; A61N 2005/1024; A61N 2005/1098
  See application file for complete search history.

(56) References Cited

U.S. PATENT DOCUMENTS

| | | | | |
|---|---|---|---|---|
| 2004/0047804 | A1* | 3/2004 | Wolf | A61K 41/0038 424/1.11 |
| 2004/0181114 | A1* | 9/2004 | Hainfeld | A61K 41/0038 600/1 |
| 2007/0026069 | A1* | 2/2007 | Shastri | A61K 9/06 424/486 |
| 2007/0217996 | A1* | 9/2007 | Levy | A61K 41/0038 424/1.33 |

OTHER PUBLICATIONS

Chan, N. (2007) Tumor hypoxia, DNA repair and prostate cancer progression: new targets and new therapies. Future Oncol. 3: 329-41.

Semenza, G. (2012) Hypoxia-Inducible Factors: Mediators of Cancer Progression and Targets of Cancer Therapy. Trends Pharmacol. Sci. 33: 207-214.

Chiche, J. et al. (2010) Tumour Hypoxia Induces a Metabolic Shift Causing Acidosis: A Common Feature in Cancer. J. Cell Mol. Med. 14: 771-794.

López-Lázaro, M. (2007) Dual Role of Hydrogen Peroxide in Cancer: Possible Relevance to Cancer Chemoprovention and Therapy. Cancer Lett. 252: 1-8.

Calcinotto, A. et al. (2012) Modulation of Microenvironment Acidity Reverses Anergy in Human and Murine Tumor-Infiltrating T Lymphocytes. Cancer Res. 72: OF1-OF11.

Fischer, B. (2000) Acidic pH inhibits non-MHC-restricted killer cell functions. Clin. Immunol. 96, 252-263.

Overgaard, J.; Horsman, M.R. (1996) Modification of Hypoxia Induced Radioresistance in Tumors by the Use of Oxygen and Sensitizers. Semin. Radiat. Oncol. 10-12.

Luo, X.L. et al. (2004) A Novel Glucose ENFET Based on the Special Reactivity of MnO2 Nanoparticles. Biosens. Bioelectron. 19: 1295-1300.

Luo, Y. (2007) Preparation of MnO2 Nanoparticles by Directly Mixing Potassium Permanganate and Polyelectrolyte Aqueous Solutions. Mater. Lett. 61: 1893-1895.

Bai, Y. et al. (2007) Choline Biosensors Based on a Bi-Electrocatalytic Property of MnO2 Nanoparticles Modified Electrodes to H2O2. Electrochem. Commun. 9: 2611-2616.

Gordijo, C.R. et al. (2010) Glucose-Responsive Bio-Inorganic Nanohybrid Membrane for Self-Regulated Insulin Release. Adv. Func. Mater. 20: 1404-1412.

Liu, X. (2012) BSA-Templated MnO2 Nanoparticles as Both Peroxidase and Oxidase Mimics. Analyst. 137: 4552-4558.

Shalviri, A et al. (2013) Design of pH-responsive nanoparticles of terpolymer of poly(methacrylic acid), polysorbate 80 and starch for delivery of doxorubicin, Colloids and Surfaces-Biointerfaces. 101: 405-13.

Shuhendler, A.J.et al. (2011) Hybrid quantum dot-fatty ester stealth nanoparticles: Toward clinically relevant in vivo optical imaging of deep tissue, ACS Nano. 5: 1958-66.

Prasad, P. et al. (2013) Doxorubicin and mitomycin C co-loaded polymer-lipid hybrid nanoparticles inhibit growth of sensitive and multidrug resistant human mammary tumor xenografts, Cancer Letters. 334: 263-273.

\* cited by examiner

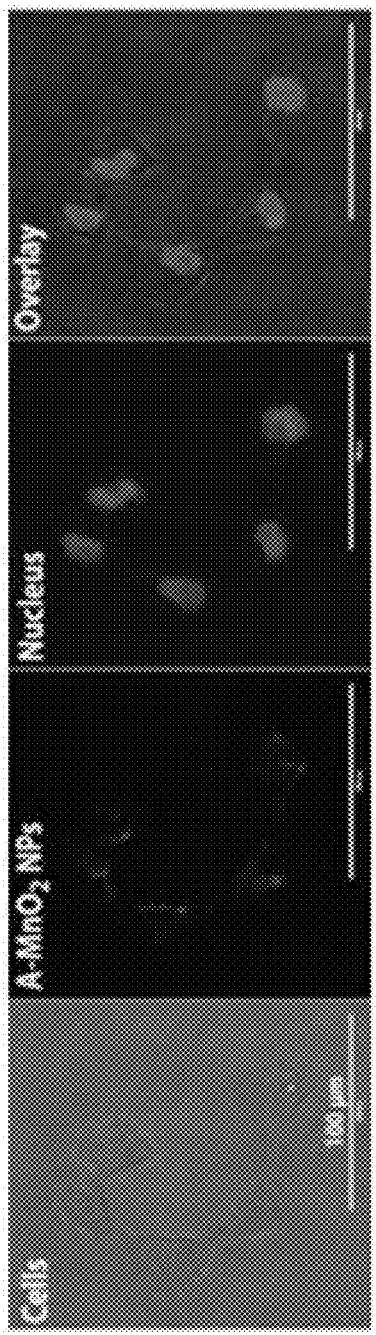
Fig. 6d
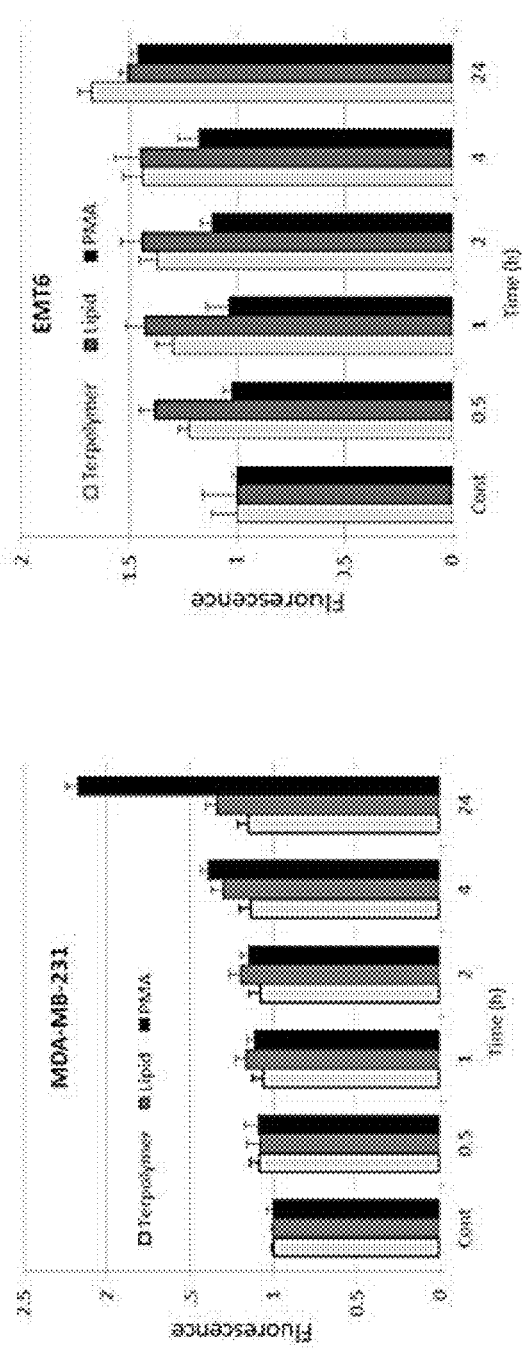
Fig. 6g
Fig. 6f

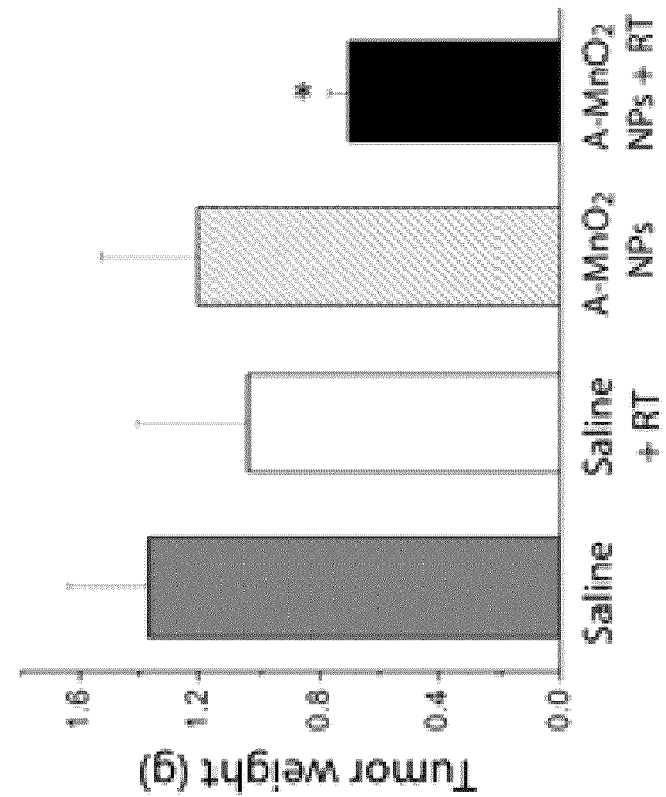
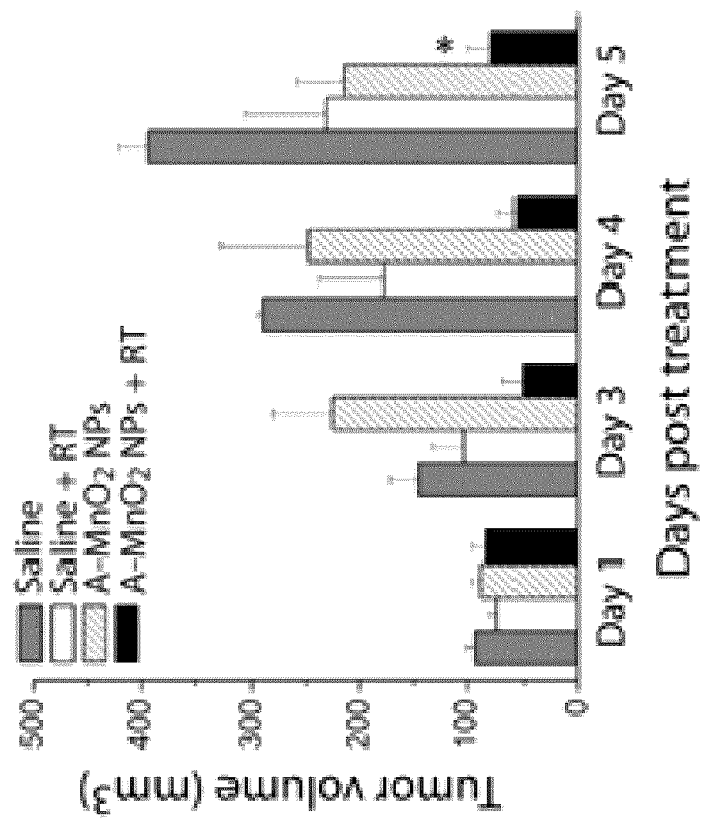
Fig. 12b
Fig. 12a

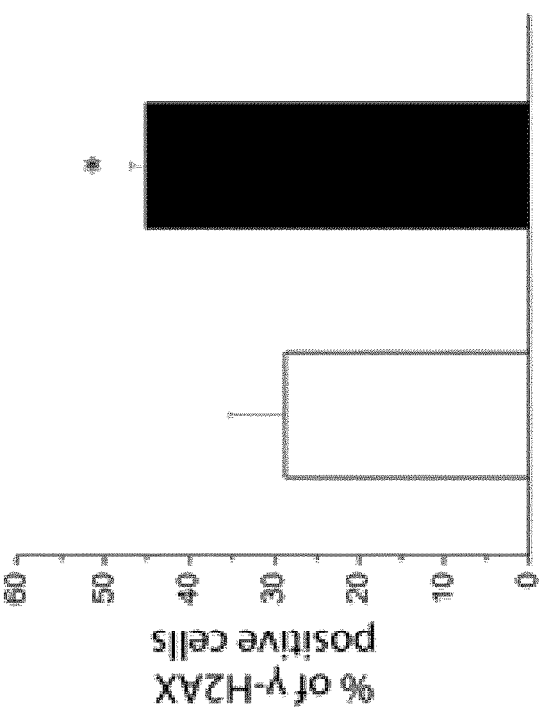
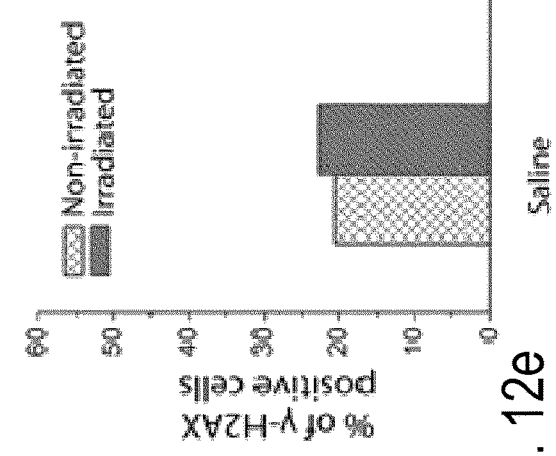
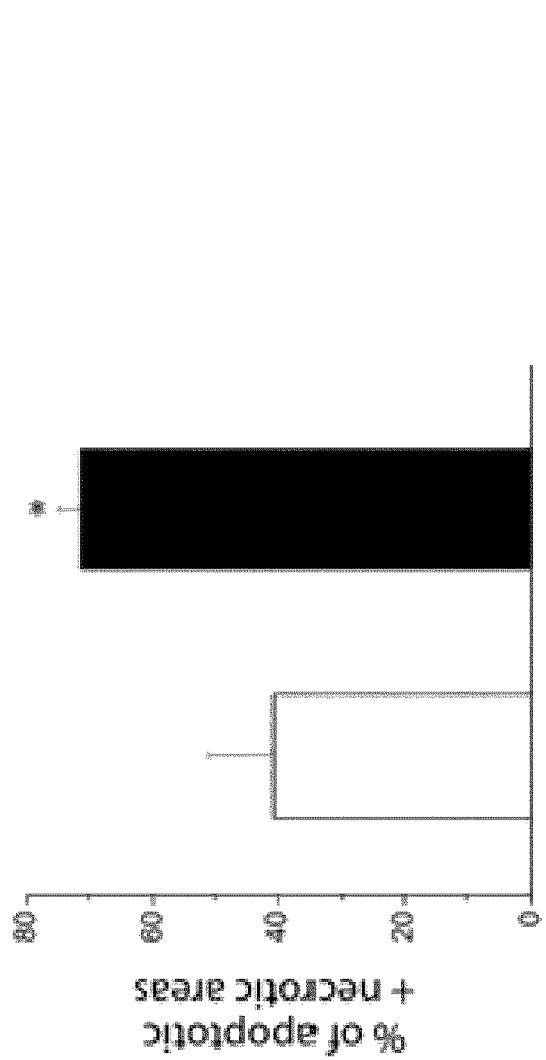
Fig. 12c
Fig. 12d
Fig. 12e

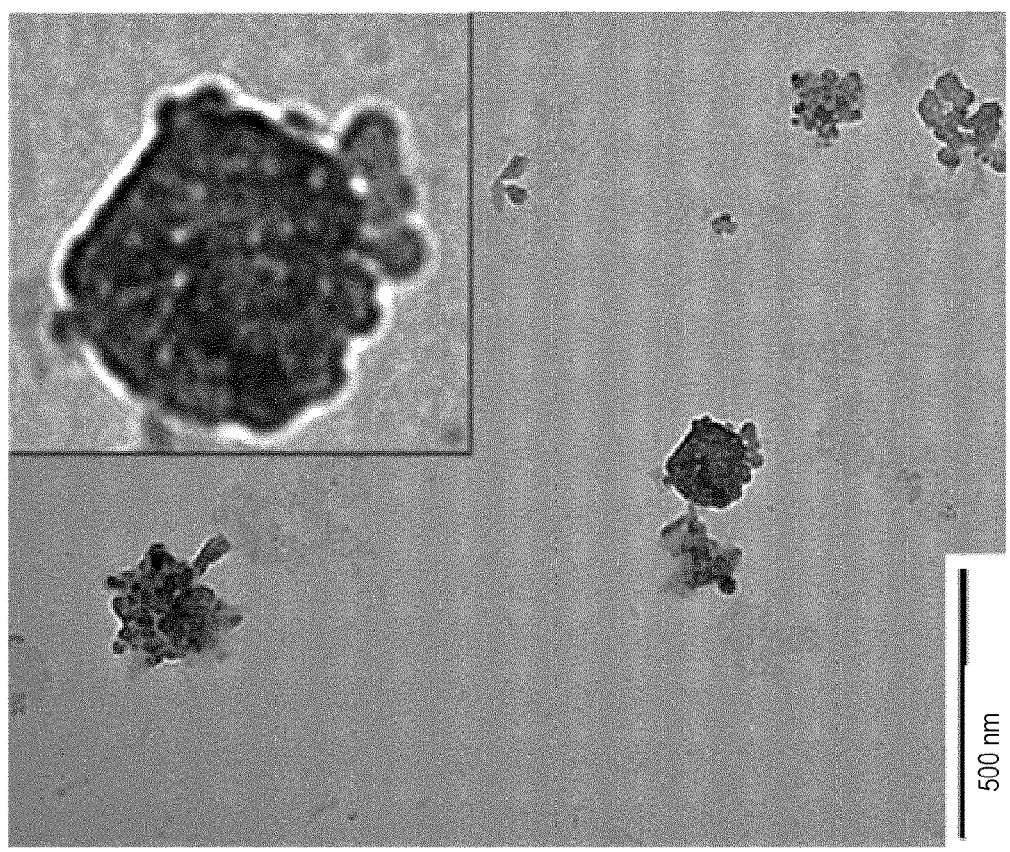
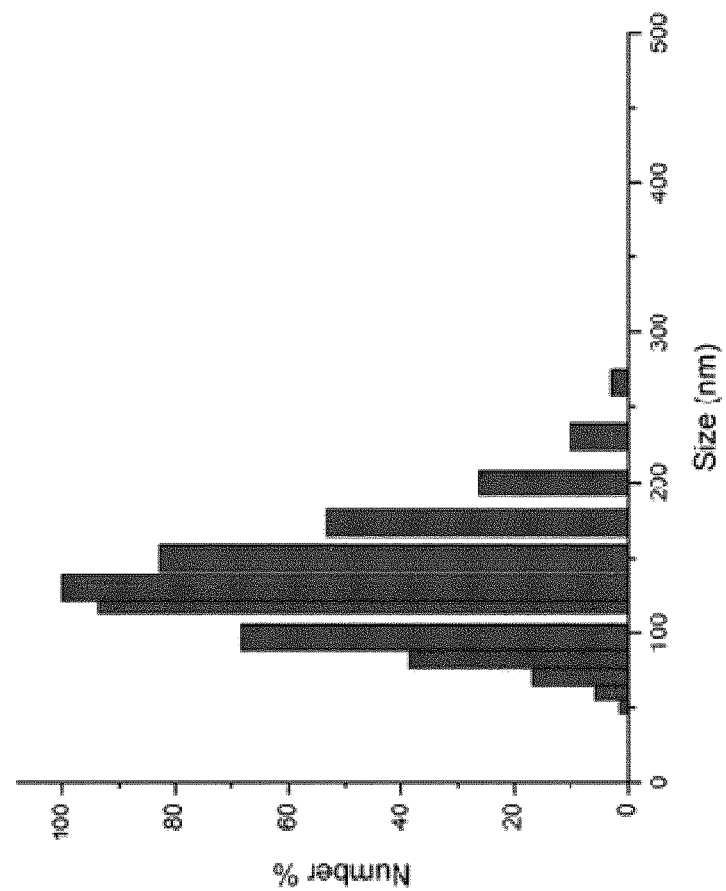
Fig. 14b
Fig. 14a

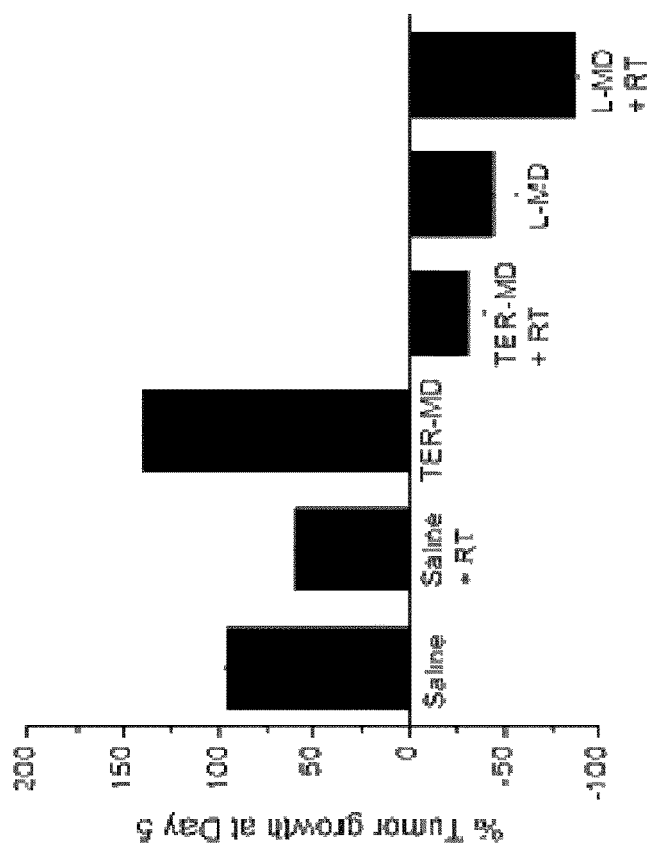
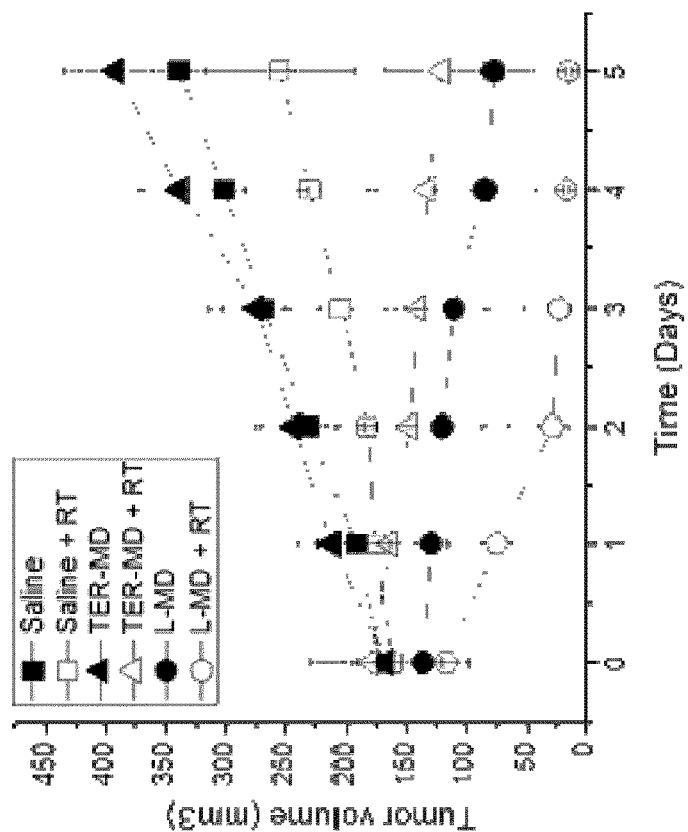
Fig. 23a
Fig. 23b

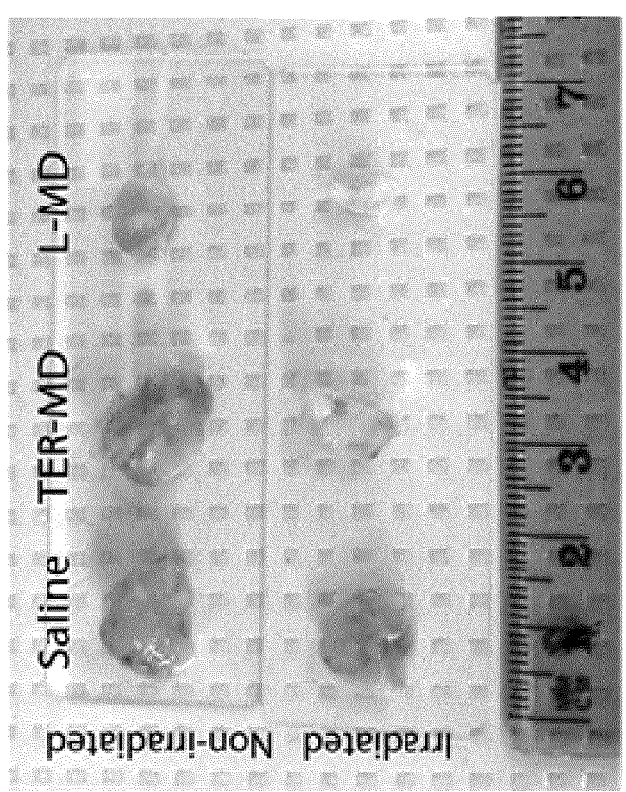
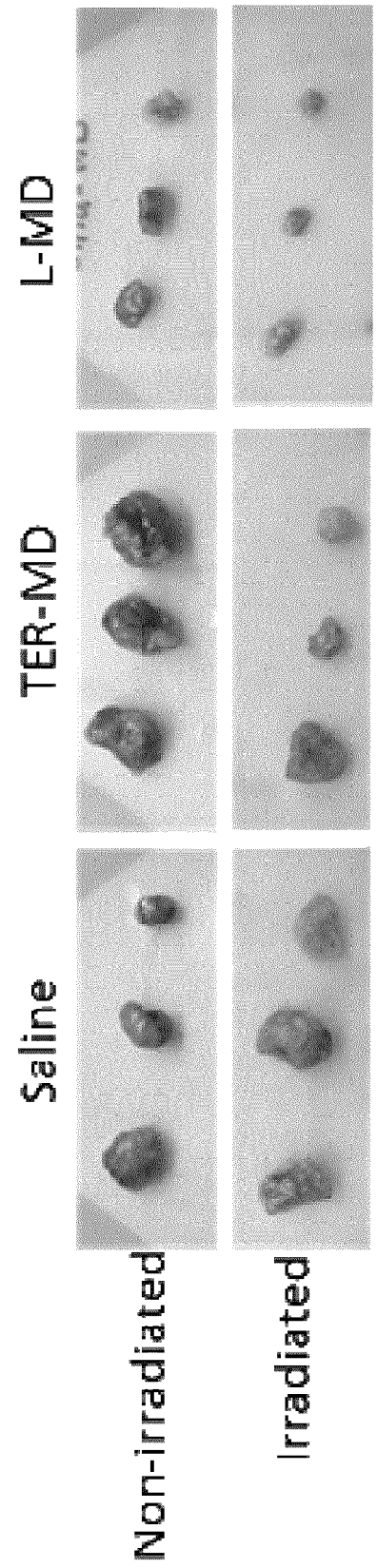
Fig. 24b
Fig. 24c

MULTIFUNCTIONAL NANOPARTICLE COMPOSITIONS AND USES THEREOF

CROSS REFERENCE TO RELATED APPLICATIONS

This application is a national stage application under 35 U.S.C. 371 of International Application No. PCT/CA2015/050277, filed Apr. 7, 2015, which in turn claims the benefit under 35 U.S.C. 119(e) of U.S. provisional application Ser. No. 61/974,878, filed Apr. 3, 2014, the contents of each of which are hereby incorporated by reference into the present disclosure.

STATEMENT REGARDING FEDERALLY SPONSORED RESEARCH OR DEVELOPMENT

Not applicable.

BACKGROUND

Insufficient oxygenation (hypoxia), acidic pH (acidosis), and elevated levels of reactive oxygen species (ROS), such as $H_2O_2$, are characteristic abnormalities of the tumor microenvironment (TME). These abnormalities promote tumor aggressiveness, metastasis and resistance to therapies. To date, there is no treatment available for comprehensive modulation of the TME. Approaches so far have been limited to regulating hypoxia, acidosis or ROS individually, without accounting for their interdependent effects on tumor progression and response to treatments.

In solid tumors, hypoxia (low oxygenation) often occurs as a consequence of a disrupted balance between the supply and consumption of $O_2$, owing in part to tumor growth and vascular abnormalities, the latter also affecting $O_2$ transport insufficiencies.[1] Hypoxia, a characteristic of the TME, has been shown to contribute to the cancer resistance to radiation therapy (RT) and to promote clinically aggressive phenotypes in cancer.[2,3] It has been shown that clinically relevant hypoxic levels are detected in 30-90% prostate cancers and nearly 40% of breast cancers with oxygen concentrations below that required for half-maximal radiosensitivity, which significantly reduces the effectiveness of ionizing radiation therapy[4,5].

Hypoxia also leads to chronic over activation of hypoxia-inducible-factor-1 (HIF-1) which plays a pivotal role in adaptive responses to hypoxia by modulating various cellular functions like proliferation, apoptosis, angiogenesis, pH balance and anaerobic glycolysis.[6,7] Upon activation, HIF-1 binds to the hypoxic responsive element, thereby promoting transcription of various genes including VEGF (vascular endothelial growth factor) and genes encoding for glucose transporters8. The expression of VEGF further induces angiogenesis and plays a key role in promoting malignant tumor growth.[9,10] HIF-1 also mediates the switch from aerobic to anaerobic metabolism in hypoxic tumors for energy preservation by activating glucose transporters and glycolytic enzymes leading to an increase in levels of lactic acid and acidosis (lower extracellular pH, pHe<6.9).[11,12] In addition, hypoxia and high proliferation of cancer cells produce excess amounts of reactive oxygen species (ROS), e.g. hydrogen peroxide ($H_2O_2$).[13] Together, hypoxia, acidosis and ROS promote mutagenesis, metastasis of cancer cells, angiogenesis and resistance to therapies, contributing to treatment failures.

Known effects of the TME are the culmination of tumor resistance to RT and chemotherapy (CT). TME-related chemoresistance is attributed to several intrinsic cellular mechanisms, mostly to the increase in ABC transporters and gene transcription induced by HIFs.[14] HIF-1α and ROS are crucial mediators of hypoxia-mediated ABC transporter gene expression[14]. ROS may contribute to hypoxia-independent upregulation and activation of HIFs or nuclear factor kappa B (NF-kB). ROS may also induce multidrug resistance protein-1 (MDR1) expression through functional HIF-1α of NF-kB transcriptional binding sites on the promoter of MDR1[15,16]. On top of hypoxia and ROS, tumor acidosis may render cancer cells chemoresistant as many cancer drugs are mildly basic (pKa>7.5) and their protonation in the extracellular space of tumors may decrease the drug permeation through cell membranes (ion trapping effect). In vivo studies have shown that the uptake and efficacy of several clinically used cancer drugs are reduced by the acidic pHe of solid tumors[17]. The physiologic changes cancer cells undergo in response to low pHe also contribute to chemoresistance, including reduced apoptotic potential, genetic alteration (p53 mutations) and elevated activity of P-glycoprotein 1 (Pgp). The radioresistance, on the other hand, can be directly caused by hypoxia. Radiation and oxygen combine to "fix" DNA thus inhibiting intrinsic DNA repair mechanisms to make DNA damage permanent.

Besides its direct effect on chemoresistance, acidosis alone exhibits many effects on cancer malignancy, tumor development, and immune cell proliferation and activity against cancer cells. The acidic TME regulates apoptosis, cell proliferation, clonal evolution, cancer cell metastasis, and angiogenesis and also modulates tumor inflammatory response and anti-tumor immunity (immune cell function)[17]. It has been demonstrated that tumor acidosis reduces the inflammatory and immune response in the tumor. Acidosis decreases the activity of natural killer (NK) and lymphokine-activated killer (LAK) cells. Acidosis also reduces the release of tumor necrosis factor (TNF-α), which primary role is the regulation of immune cells[19]. Significantly elevated serum lactate levels were detected in cancer pateints with high tumor burden and lactate was found to inhibit T-cell proliferation and cytotoxic activity. Counteracting tumor acidosis (i.e., by neutralization of the acidic tumor pH) can improve tumor prognosis by promoting tumor self-destructive mechanisms.

Another aspect of the TME is the effect of excessive ROS, such as $H_2O_2$. Increased $H_2O_2$ levels in the solid tumor induce the activation of HIF-1α, which in turn triggers a cascade of expression of numerous genes and proteins associated with acquisition of a more malignant behavior, treatment resistance, and disease relapse. It has been demonstrated that the malignant phenotype of cancer cells can be reversed just by decreasing the cellular levels of $H_2O_2$[13]. Hydrogen peroxide has been identified as a "fertilizer" to promote tumor initiation, growth, progression, recurrence and metastasis. Abnormal production of hydrogen peroxide by cancer cells and cancer-associated fibroblasts has been shown to drive accelerated DNA damage, inflammation, and altered metabolism in the TME[21]. It is known that cancer cells release $H_2O_2$ which can trigger oxidative stress in neighboring fibroblasts and activation of nuclear factor kappa B (NF-kB) and HIF, driving to cancer stromal inflammation and aerobic glycolysis. The $H_2O_2$-activated glycolytic fibroblasts will then produce high-energy nutrients such as lactate to promote tumor growth[21].

Manganese (Mn) is the second most abundant transition metal on Earth occurring in multiple valence states in the environment, and is an essential micronutrient for most organisms. Its oxo-compounds (which include oxides, hydroxides, and oxyhydroxides) are some of the strongest oxidants naturally found in the environment showing a wide range of biological and technological applications[20]. Besides its traditional applications in catalysis and electrodes in lithium batteries, manganese dioxide (MD) NPs have also been employed in the field of glucose biosensors[98]. Such applications are based on the high reactivity of MD NPs towards $H_2O_2$. Thus, the high reactivity and specificity of MD NPs towards $H_2O_2$ can be used for the simultaneous and sustained production of $O_2$ and regulation of pH. Another advantage of MD NPs is their dual functions as both catalyst and reactant. In the latter case, they are decomposed to harmless, water-soluble $Mn^{21}$ ions[26], avoiding the in vivo accumulation of the metal oxide commonly observed for other metal-based nanoparticle (NP) systems[27]. Compared with other metal NPs extensively explored for biological applications, MDNPs have been limited to use in biochemical sensors[26, 28] and bioassays[29] and their reactivity towards in vivo, endogenous $H_2O_2$ has not been studied for in vivo ROS reduction, $O_2$ production or for the regulation of pH in biological systems.

To date, various strategies have been proposed to modify the TME, aimed at the (systemic) improvement of tumor oxygenation to surmount hypoxia-associated radioresistance. These strategies include hypoxia by hyperbaric oxygen therapy,[22] artificial blood substitutes,[23] and drugs which preferentially kill or sensitize hypoxic cells to radiation.[24] Unfortunately, the utility of such methods in clinical settings is limited due to safety concerns, reagent stability and/or inconsistent clinical response. Therefore, there is a continued and urgent need for new strategies to improve tumor oxygenation in vivo to enhance the radiation response in solid tumors.

SUMMARY

In its first aspect, the present disclosure relates to multifunctional nanoparticle compositions. In certain applications, the compositions are useful for the treatment of cancer by enhancing the anti-tumor effectiveness of radiation directed to a tissue or a tumor. The multifunctional nanoparticle composition can include a coated nanoparticle embedded in a matrix. The coated nanoparticle can include a metal oxide nanoparticle and a functional coating on the surface of the metal oxide nanoparticle. The coated nanoparticle embedded in the matrix can be in nanoparticulate form.

In some embodiments, the matrix can include organic groups, inorganic compounds, proteins, nucleic acids, polymers, lipids and the mixtures thereof.

In some embodiments, the coated nanoparticle embedded in the matrix further comprises a functional moiety, such as a targeting moiety, a detectable moiety, a radioisotope, a radionuclide, a labeling agent, an imaging agent and the mixtures thereof.

In some embodiments, the metal oxide nanoparticle is a manganese dioxide nanoparticle (MD NP).

In some embodiments, the functional coating is selected from the group consisting of a biocompatibility coating, a colloidal coating, an organic coating, an inorganic coating, a hydrophilic coating, and the mixtures thereof.

In some embodiments, the functional coating comprises a first layer. For example, the first layer can be poly(allylamine hydrochloride) (PAH). The first layer may also be linked to an oleic acid (o) introduced by covalent bond or physical attachment.

In some embodiments, the multifunctional nanoparticle composition is A-MD NP (Formulation #1) in the size of about 20 nm to about 1000 nm in diameter.

In some embodiments, the multifunctional nanoparticle composition is TER-MD NP (Formulation #2) in the size of about 50 nm to about 1000 nm in diameter.

In some embodiments, the multifunctional nanoparticle composition is a PEG-TER-MD NP (Formulation #3) in the size of about 50 nm to about 1000 nm in diameter.

In some embodiments, the multifunctional nanoparticle composition is L-MD NP (Formulation #4) in the size of about 50 nm to about 1000 nm in diameter.

In some embodiments, the multifunctional nanoparticle composition is PMA-MD NP (Formulation #5) in the size of about 50 nm to about 1000 nm in diameter.

In some embodiments, the nanoparticles are mixed with a pharmaceutically acceptable vehicle is in the form suitable for intratumoral injection, peritumoral injection or intravenous injection.

In its second aspect, the present disclosure relates to methods of preparing a multifunctional nanoparticle composition for the treatment of cancer by enhancing the anti-tumor effectiveness of radiation directed to a tissue or a tumor, the method comprising the steps of (1) preparing a metal oxide nanoparticle, (2) treating the metal oxide nanoparticle of step (1) with a first functional layer to form a single-coated functional metal oxide nanoparticle; and (3) loading single-coated functional metal oxide nanoparticles of step (2) in a matrix to form a particle loaded with one or more functional metal oxide nanoparticles.

In some embodiments, the method may further comprise a step of treating the particle loaded with one or more coated functional metal oxide nanoparticles of step (3) with a functional moiety to form a functional loaded particle.

In its third aspect, the present disclosure relates to methods of treating cancer disease in a subject comprising the steps of administering an effective amount of a multifunctional nanoparticle composition disclosed herein to the subject, and applying an ionizing radiation treatment to the subject, wherein the cancer disease is treated.

In some embodiments, the administration of the composition is prior to the application of the radiation treatment. More preferably, the composition is intravenously injected to the subject about 1 to about 24 hours prior to the radiation, or the composition is intratumorally injected to the subject about 5 minutes to about 3 hours prior to the radiation.

In its fourth aspect, the present disclosure relates to methods of enhancing a radiation directed to a tissue or a tumor in a subject comprising the steps of (1) administering an effective amount of a multifunctional nanoparticle composition disclosed herein to the subject, and (2) applying radiation to the subject, wherein the radiation is enhanced in the subject.

In its fifth aspect, the present disclosure relates to the use of a multifunctional nanoparticle composition as described herein for the manufacture of a medicament for the treatment of cancer in combination with radiation in a subject.

In its sixth aspect, the present disclosure relates to the use of a multifunctional nanoparticle composition as described herein for the manufacture of a medicament for the enhancement of a radiation directed to a tissue or a tumor in a subject.

BRIEF DESCRIPTION OF THE DRAWINGS

FIGS. 12a-f show the effect on tumor growth after treatment with radiation and A-MD NPs: Tumors (n=3/group) were treated with intratumoral injection of 1) Saline, 2) Saline+RT, 3) A-MD NP, or 4) A-MD NP+RT. A radiation dose of 10 Gy was given 30 minutes after saline or A-MD NP treatment. (a) Tumor volume measured over time following treatment. (b) Ex vivo measurement of tumor weight at the end of Day 5. (c) Quantification of % necrotic+ apoptotic area in tumors after treatment. (d) Quantification of DNA DSBs as measured by γ-H2AX staining in tumors after treatment. (e) Quantification of DNA DSBs determined by measuring % of positive γ-H2AX cells in tumor tissue implanted in dorsal window chamber and treated with Saline and A-MD NPs. (f) Representative image of tumor implanted in dorsal window chamber and treated with Saline and A-MD NPs, and immunohistochemical image of tumor tissue stained with γ-H2AX.*=statistically significant difference (*p<0.05) as compared to all other groups.

FIG. 14 shows (a) size distribution and (b) TEM image of pMD NPs loaded in a terpolymer crosslinked denatured BSA matrix (TER-MD).

FIG. 23 shows effect on tumor growth of treatment with various MD-containing NP formulations and NPs+RT up to 5 days. Tumors (n=3/group) were treated with a single intratumoral injection of 1) saline, 2) saline+RT, 3) TER-MD, 4) TER-MD+RT, 5) L-MD, and 6) L-MD+RT. A radiation dose of 10 Gy was applied to the tumors 30 minutes post injections. (a) Tumor volume measured using a caliper over time at various times. (b) Percent of tumor weight change at Day 5 post treatment after the mice were sacrificed. i.t. injection of saline with or without RT was used as a control.

DETAILED DESCRIPTION

Figure 1A:
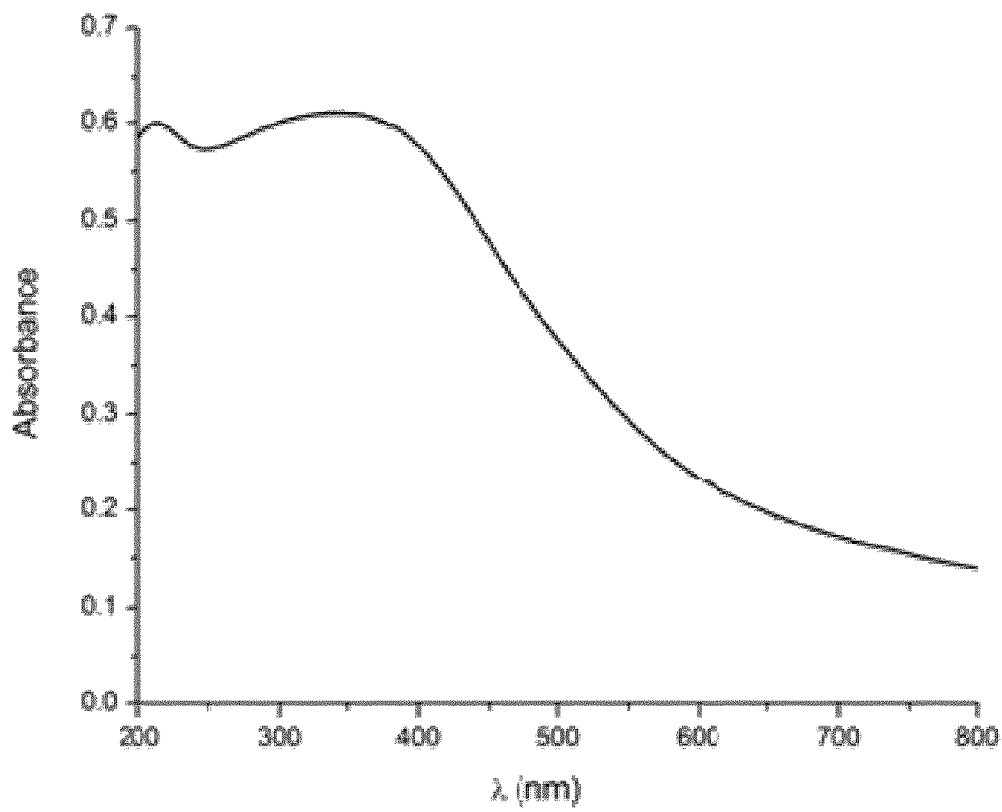
FIG. 1 shows characterization of bare $MnO_2$ (bMD) NPs. (a) UV-Vis spectrum; (b) size distribution; (c) TEM image; and (d) X-ray powder diffraction (XRD) of obtained bMD NPs.
Figure 1B:
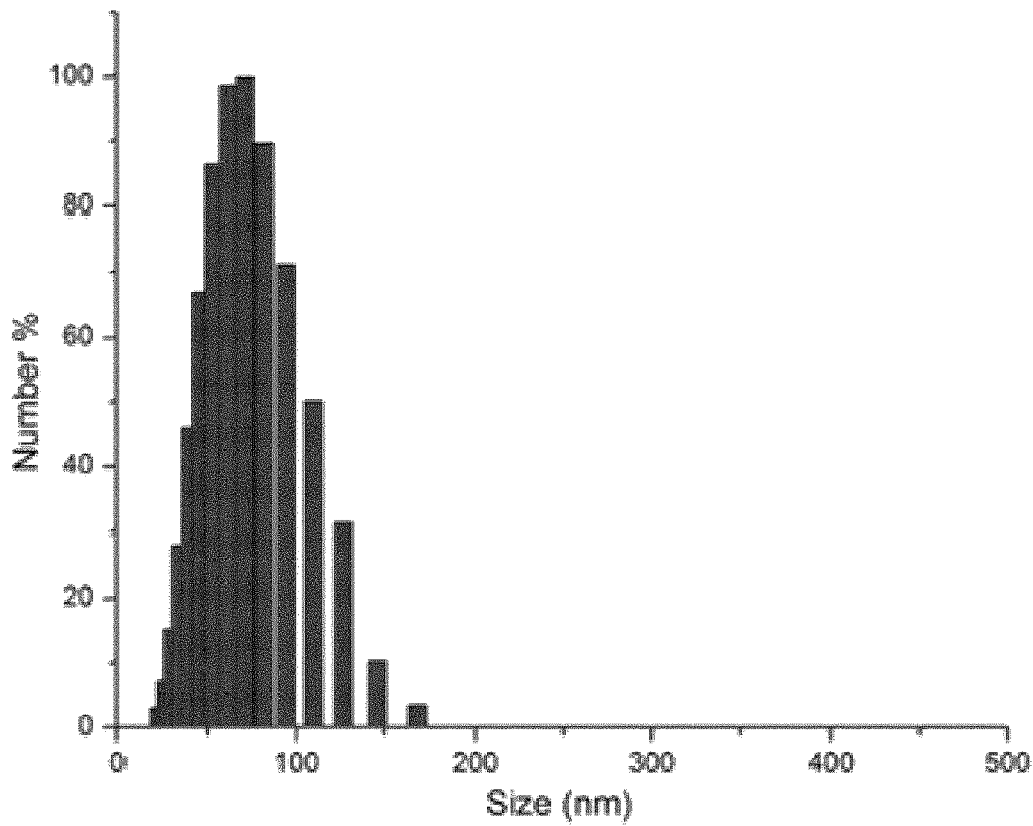
Figure 1C:
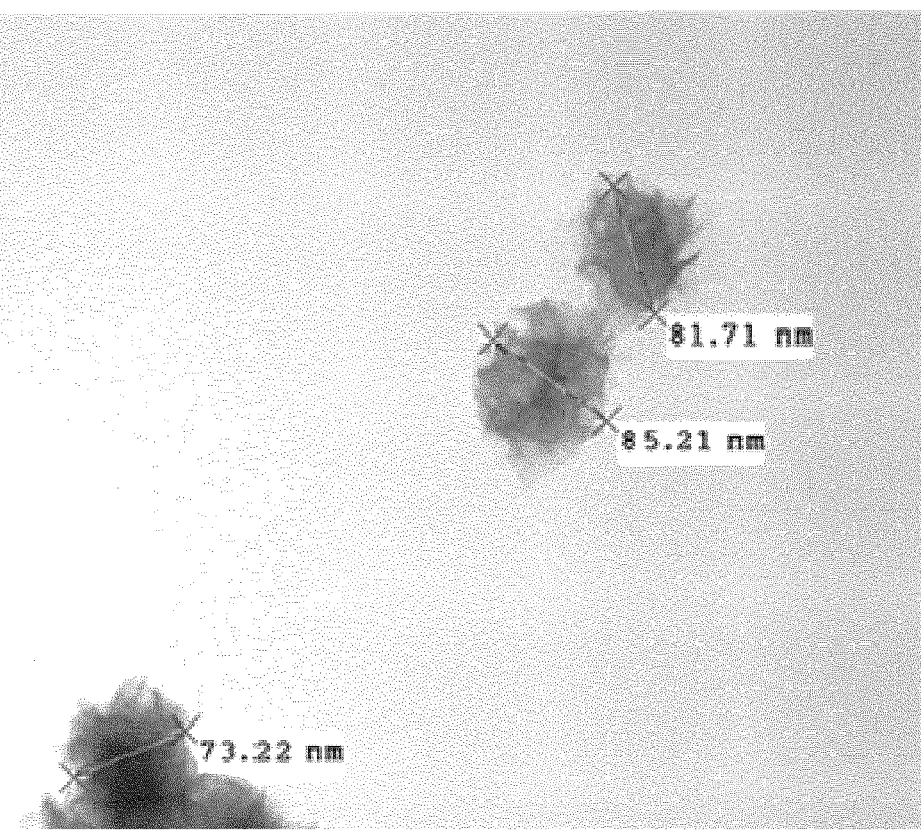

The present disclosure relates to multifunctional nanoparticle compositions and methods of using the compositions for the treatment of cancer by enhancing the anti-tumor effectiveness of ionizing radiation directed to a tissue or a cell of a subject.

The present disclosure provides engineered new multifunctional and colloidally stable bioinorganic nanoparticles composed of bioreactive $MnO_2$ nanoparticles (MD NPs) loaded into a biocompatible polymeric and/or lipidic matrix such as polyelectrolyte-albumin complex, graft terpolymer or poly(methacrylic acid)-polysorbate 80-starch (TER) crosslinked albumin, and amphiphilic polymer, and fatty acids. The reactivity of MD towards peroxides for regulation of the TME with simultaneous $H_2O_2$ quenching, oxygen generation and pH increase was utilized. In vitro studies showed that these NPs can generate oxygen by reacting with $H_2O_2$ produced by cancer cells under hypoxic conditions. In a murine orthotopic breast tumor model, albumin-based MD (A-MD) NPs increased tumor oxygenation by 45% by reacting with endogenous $H_2O_2$ produced within the tumor while increasing tumor pH from pH 6.7 to pH 7.2. Intratumoral treatment with A-MD NPs led to the downregulation of two major regulators in tumor progression and aggressiveness, i.e., hypoxia-inducible factor-1 alpha (HIF-1α) and vascular endothelial growth factor (VEGF) in the tumor. Combination treatment of the tumors with MD NPs and ionizing radiation significantly inhibited tumor growth, increased DNA double-strand breaks and cancer cell death as compared to radiation therapy (RT) alone. Combination of RT with terpolymer cross-linked denatured albumin-based MD (TER-MD) NPs or lipid-based (L-MD) NPs also caused more death of hypoxic prostate cancer cells and more tumor necrosis than radiation alone. These results suggest the usefulness of MD NPs for modulation of the TME and enhancement of radiation therapeutic response in the treatment of cancer.

The inventors unexpectedly discovered the high reactivity and specificity of metal oxide nanoparticles, particularly, manganese dioxide nanoparticles (MD NPs), towards tumor $H_2O_2$ to modulate the tumor microenvironment (TME) by the simultaneous and sustained production of $O_2$ and regulation of pH[25, 26]. Unlike other experimental and clinical strategies to increase tumor oxygenation, which are mostly achieved by the delivery of molecular oxygen by nanoparticles with limited $O_2$ loading capacity or hyperbaric treatment strategies,2 MD NPs are able to generate $O_2$ in situ for a prolonged time by reacting with undesirable and abundantly available tumor metabolites ($H_2O_2$ and H+).

The inventors also found that MD NPs have dual functions as both catalyst and reactant in vivo. In the latter case, MD NPs are decomposed to harmless, water-soluble $Mn^{2+}$ ions,[26] avoiding the in vivo accumulation of the metal oxide commonly observed for other metal-based nanoparticle (NP) systems.[27] So far, the reactivity of MD NPs towards tumor $H_2O_2$ has not been studied for in vivo ROS reduction, $O_2$ production or for the regulation of pH in biological systems.

Thus, for the first time, the inventors developed compositions based on multifunctional metal oxide nanoparticles, particularly manganese dioxide nanoparticles (MD NPs) and use them for the modulation of hypoxia of the TME, and for enhancement of radiation-induced tumor cell cytotoxicity in a murine breast tumor animal model. As the majority of cancer treatment and therapy focus on developing new drugs and modalities against tumor cells, the inventors envision that this technology can solve a bottleneck challenge in tumor response to radiation therapy and can be used as a platform technology to enhance the effectiveness of radiation treatment and associated therapies.

In its first aspect, the present disclosure provides multifunctional nanoparticle compositions for the treatment of cancer by enhancing the anti-tumor effectiveness of radiation directed to a tissue, cell or a tumor. Specifically, the multifunctional nanoparticle composition can include a coated nanoparticle embedded in a matrix. The coated nanoparticle can include a metal oxide nanoparticle and a functional coating on the surface of the metal oxide nanoparticle.

The term "metal oxide nanoparticle" as used herein refers to a particle comprising a solid core of an inorganic metal oxide material comprising at least partially ordered three dimensional array of metallic cations and oxide anions. The nanoparticle size desired by this disclosure can vary widely, and essentially any particle size in the nanoparticle size range (e.g., below 1,000 nm) can be used. The shape of the nanoparticles may be regular (column, cube, cylinder, pillar, pyramid, rod, sphere, tube, wire, flake, disk, etc.) or irregular/random, which for example can be controlled by adjusting the reaction dynamics and aging/ripening time.

There are no limitations on the base metal of the metal oxide nanoparticles for this disclosure. For example, the base metal may be one or more selected from Cu, Sn, Ti, V, Cr, Mn, Co, Fe, Ni, Zn, Al, Y, Zr, Mo, In, Mg, La, Ce, Nd, Sm, Eu, Gd, Si, Ge, Pb, Ag, Tl, Cs, Hf, and Bi. In certain applications, the base metal may be one or more selected from V, Cr, Mn, Co, Y, Zr, Mo, In, Mg, La, Ce, Nd, Sm, Eu, Gd, Ge, and Bi. In certain applications, the base metal may be one or more selected from V, Cr, Mn, Mo, and Co. In certain applications, the base metal may be one or more selected from V, Cr, Mn, Fe, and Co. In certain applications, the base metal may be one or more selected from Ti, Ag, and Mn. In a specific embodiment of the present disclosure, the base metal is Mn.

There are no limitations on the chemical composition of the metal oxide nanoparticles for this disclosure as well. For example, some suitable metal oxide nanoparticles have a well defined chemical composition (e.g., stoichiometric metal oxides having a well defined composition, such as $MnO_2$), while some "non-stoichiometric" metallic oxides have variable proportions of mixtures of the metal cations, such as for example $BaTi_{0.8}Zr_{0.2}O_3$ or those with metal and/or oxygen ion vacancies. In certain applications, the metal oxide nanoparticle may be one or more selected from $Al_2O_3$, $TiO_2$, $ZrO_2$, MgO, $NiO_2$, $Co_3O_4$, AgO, CuO, BiO, $Rb_2O$, $In_2O_3$, $Tl_2O_3$, $Cs_2O$, and $HfO_2$. In certain applications, the metal oxide nanoparticle may be one or more selected from $MnO_2$, $Mn_2O_3$, $Mn_2O_7$, MnOOH, $Mn_3O_4$, and $Mn(C_2O_4)$. In a specific embodiment of the present disclosure, the metal oxide nanoparticle is $MnO_2$ (MD NP).

To make metal oxide nanoparticles suitable for clinic use, the inventors designed and formulated the nanoparticles under the following consideration: (1) reducing toxicity; (2) improving colloidal stability under physiological conditions; (3) improving blood circulation and half-life of the nanoparticles; (4) increasing tumor uptake and retention; (5) modulating the kinetics of the nanoparticle reaction towards $H_2O_2$ and the rates of oxygen generation and pH changes. The inventors have found that these criteria can be achieved by modifying the coating material, the size, the morphology, the structure, the surface, the charge, the hydrophobicity and the chemistry of the nanoparticles.

In some embodiments, the surface of the metal oxide nanoparticle disclosed in the present application is modified with a functional coating, including, but is not limited to, a biocompatibility coating, a colloidal coating, an organic coating, an inorganic coating, a hydrophilic coating, or the mixture thereof. These functional coatings are used to increase the stability, biocompatibility and other functionality of the metal oxide nanoparticles. The coating strategies and processes are well known in the art.

For example, biocompatible coating materials include, but are not limited to, synthetic and biological polymers, copolymers and polymer blends, and inorganic materials. Polymer materials may include various combinations of polymers of acrylates, siloxanes, styrenes, acetates, esters, alkylene glycols, alkylenes, alkylene oxides, parylenes, lactic acid, and glycolic acid. Further suitable coating materials include a hydrogel polymer, a histidine-containing polymer, and a combination of a hydrogel polymer and a histidine-containing polymer. Coating materials may also include combinations of biological materials such as a polysaccharide, a polyaminoacid, a protein, a lipid, a nucleic acid, a glycerol, and a fatty acid. Other biological materials for use as a coating material may be a heparin, heparin sulfate, chondroitin sulfate, chitin, chitosan, cellulose, dextran, alginate, starch, carbohydrate, and glycosaminoglycan. Proteins may include an extracellular matrix protein, proteoglycan, glycoprotein, albumin, peptide, and gelatin. These materials may also be used in combination with any suitable synthetic polymer material.

Inorganic coating materials may include any combination of a metal, a metal alloy, and a ceramic. Examples of ceramic materials may include a hydroxyapatite, silicon carbide, carboxylate, sulfonate, phosphate, ferrite, phosphonate, and oxides of Group IV elements of the Periodic Table of Elements. These materials may form a composite coating that also contains any biological or synthetic polymer. Where the magnetic particle is formed from a magnetic material that is biocompatible, the surface of the particle itself operates as the biocompatible coating.

Organic coatings or organic phases introduce substantially of carbon to the nanoparticles by attaching a monolayer or multilayers of organic compounds to the surface of the nanoparticles. Organic compounds can be organic groups, small molecules, monomers, oligomers or polymers.

Hydrophilic coatings on the nanoparticles can be made as well. For example, hydrophobic nanoparticles can be made suspendable in aqueous solutions by introducing ionic or polar groups on the nanoparticle surface. Depending on the starting surface properties of the particles, this can be accomplished, for example, by linking molecules to the nanoparticle surface through chemisorption, to reactive groups on the particle surface that may have been introduced in the synthesis process through covalent bonds, through coordination bonds, ionic bonds, pi-bonds, or hydrophobic interactions.

The coating material may also serve to facilitate transport of the nanoparticle into a cell, a process known as transfection. Such art-known coating materials, known as transfection agents, include vectors, prions, polyaminoacids, cationic liposomes, amphiphiles, and non-liposomal lipids or any combination thereof. A suitable vector may be a plasmid, a virus, a phage, a virion, and a viral coat. The nanoparticle coating may be a composite of any combination of transfection agent with organic and inorganic materials, such that the particular combination may be tailored for a particular type of a healthy or diseased cell and a specific location in a tissue or organ.

The metal oxide nanoparticles can be multi-functionalized. For example, the nanoparticles can be modified with one portion of the molecule exhibiting affinity to the particle or particle surface groups and another portion of the molecule having characteristics that would make the conjugate hydrophilic. The portion of the molecule or another portion could also render the conjugate biocompatible, a typical example would be a molecule terminated with a polyethylene glycol (PEG) chain. This same portion of the molecule or another portion could also introduce additional functionality on the conjugate surface for conjugating additional materials onto the nanoparticle. For example, the functional coating can further comprise a targeting ligand, wherein the targeting ligand targets the cell or tissue of interest. The functional coating can comprise a material that promotes nanoparticle aggregation within the cell or tissue of interest.

In some embodiments, the functional coating according to the present disclosure comprises a first layer or stabilizer. The first layer and the stabilizer may further be linked to an oleic acid (o) introduced by covalent bond or physical attachment.

In some embodiments, the functionally coated nanoparticles are further embedded into a matrix.

As used herein, "matrix" refers to an essentially two and/or three-dimensional environment capable of immobilizing, by embedding, entrapping or encapsulating at least one nanoparticle for the purpose of supporting the functionality of the nanoparticle. The relationship between the constituents of the matrix and the nanoparticle include, but is not limited to, covalent, ionic, and van der Waals interactions and combinations thereof.

Various materials can be used for forming a matrix, for example, without limitations, organic groups, organic compounds, inorganic compounds, polymers, organometallic compounds, surfactants, biological organic material (such as amino acids, proteins, lipids, DNA, enzymes, etc.), and the mixtures thereof. The matrix may also comprise hydrogel polymers, such as polysaccharides including agarose, dextran, carrageenan, alginic acid, starch, cellulose, or derivatives thereof.

The matrix can provide a structure to retain the nanoparticulate in a desired distribution without interfering with proper functioning of the nanoparticles in the application. Alternatively, the matrix may itself also provide some function for the application. The matrix may, for example, have a function that is different than that of the nanoparticles, have a function that compliments that of the nanoparticles, or have a function that is the same as that of the nanoparticles. As yet another example, the matrix may be selected for its surface modifying properties to beneficially modify the nanoparticles in a way that is useful in some subsequent processing or use of the nanoparticles.

The coated nanoparticles embedded in a matrix can be in the form of nanoparticles having a diameter ranging from 10 nm to 1000 nm, including but not limited to, a size ranging from 15 nm to 500 nm, from 20 nm to 200 nm, from 50 nm to 250 nm, from 100 nm to 150 nm, or any combination of the lower and upper bounds of these ranges not explicitly set forth herein. As used herein, nanoparticle diameter refers to the mean diameter as measured by a dynamic light scattering system, such as the Zetasizer Nano range, available commercially from Malvern Instruments, Ltd., Worcestershire, UK, or by using transmission electron microscope, such as Hitachi H7000, available commercially from Hitachi, Tokyo, Japan.

The nanoparticles may also be prepared in a form suitable for clinic use. Thus, in some embodiments, the compositions of the present disclosure further comprise a pharmaceutically acceptable vehicle in which the nanoparticles are mixed or dispersed.

A "pharmaceutically acceptable vehicle" used herein includes, but is not limited to, any and all solvents, dispersion media, substrates, coatings, isotonic and absorption agents, buffering agents, and the like, compatible with a desired administrations. Particularly useful examples of such vehicles include, but are not limited to, water, saline, buffers, surfactants, dispersing agents and dextrose solution. The volume of the pharmaceutical vehicle may vary according to the specific tissue-stabilizing agents and therapeutic agents selected and their respective solubilities with the vehicle. Moreover, other products may be added to the vehicle as well, if desired, for example, to maximize tissue-stabilization time, drug-delivery, preservation of life, or to optimize a particular method of delivery.

The coated nanoparticles embedded in a matrix may further link to a functional moiety. For example, the nanoparticle can comprise a detectable moiety for the tracking of the nanoparticles homing towards a tissue or tumor. The term "detectable moiety" as used herein refers to a label molecule (isotopic or non-isotopic) which is incorporated indirectly or directly into nanoparticles of the present disclosure, wherein the label molecule facilitates the detection of the nanoparticle in which it is incorporated. Thus, "detectable moiety" is used synonymously with "label molecule". Label molecules, known to those skilled in the art as being useful for detection, include without limitation, chemiluminescent and/or fluorescent molecules, electrochemiluminescence, Raman, colorimetric, hybridization protection assay, mass spectrometry, photoacoustic, magnetic, and radionuclides.

A detectable moiety also includes an imaging agent. Any suitable detectable agent can be used to be incorporated with the nanoparticles to detect the nanoparticles contained within a tissue or tumor. For example, an imaging agent may be a contrast agent, which means an agent that when delivered to an animal or human subject can improve the image obtained by a method such as magnetic resonance imaging (MRI). Such agents may include, but are not limited to gadolinium, iron oxide, manganese and magnesium salts, and the like that may be formulated into pharmaceutically acceptable compositions for administering in vivo with limited and acceptable degrees of undesirable side effects. Chelating agents containing paramagnetic metals for use in magnetic resonance imaging can also be employed as agents. Typically, a chelating agent containing a paramagnetic metal is associated with a coating on the nanoparticles. The chelating agent can be coupled directly to one or more of components of the nanoparticle such as functional amino groups. Suitable chelating agents include, but are not limited to, a variety of multi-dentate compounds including EDTA, DPTA, DOTA, and the like.

An imaging agent may also include a labeling moiety that is useful for providing an indication of the position of the label and adherents thereto, in a cell or tissue of an animal or human subject, or a cell or tissue under in vitro conditions. Such agents may include those that provide detectable signals such as fluorescence, luminescence, radioactivity, or can be detected by such methods as MRI imaging, PET imaging and the like.

The functional moiety may also be a targeting moiety. The term "targeting moiety" can refer to a molecule or molecules that are able to bind to and complex with a biomarker. The term can also refer to a functional group that serves to target or direct an imaging probe to a particular location, cell type, healthy or diseased tissue, or association. In general, a "targeting moiety" can be directed against a biomarker.

In preferred embodiments, the compositions described herein are formulated to be compatible with the intended route of administration, such as intratumoral, peritumoral, or intravenous applications. The composition may also be made in a form suitable for implant within the solid tumor using any suitable method known to those skilled in the art of penetrating tumor tissue. Such techniques may include creating an opening into the tumor and positioning the composition in the tumor. For example, suspensions, dispersions, or emulsions may be used in a pharmaceutically acceptable vehicle for such administrations and may include a sterile diluent, such as water for injection, saline solution, polyethylene glycols, glycerine, propylene glycol or other synthetic solvents; anti-bacterial agents such as benzyl alcohol or methylparabens; antioxidants such as ascorbic acid or sodium bisulfite; buffers such as acetates, citrates or phosphates, and agents for the adjustment of tonicity such as sodium chloride or dextrose. The pH may be adjusted with acids or bases, such as hydrochloric acid or sodium hydroxide. Preparations may be enclosed in ampules, disposable syringes or multiple dose vials made of glass or plastic.

The compositions can be included in a kit, container, pack or dispenser, together with medical devices suitable for delivering the compositions intratumorally, peritumorally, or intravenously. The compositions included in kits may be supplied in containers of any sort such that the life of the different components may be preserved and may not be adsorbed or altered by the materials of the container.

In its second aspect, the present disclosure provides methods of preparing a multifunctional nanoparticle composition for the treatment of cancer by enhancing the anti-tumor effectiveness of radiation directed to a tissue or a tumor, the method comprising the steps of (1) preparing a metal oxide nanoparticle core; treating the metal oxide nanoparticle core of step (1) with a first functional layer to form a single-coated functional metal oxide nanoparticle; and (3) loading single-coated functional nanoparticles of step (2) in a matrix to form a bigger particle loaded with one or several functional metal oxide nanoparticles. The method may further comprise a step of treating the bigger particle loaded with coated functional metal oxide nanoparticle of step (3) with a matrix to form a functional metal oxide nanoparticle. These preparations are well-known in the art.

The compositions of the five formulations useful in certain disease treatment applications and the methods of making them are described below.

Formulation #1: A-MD NPs.

The formulation #1 comprises a MD NPs stabilized with poly(allylamine hydrochloride) (PAH) and is further crosskinked with bovine serum albumin (BSA).

The formulation #1 can be prepared by any method known in the art. For example, aliquot MD NPs stabilized with PAH is directly mixed with BSA in aqueous medium. Thus, the MD NPs are entrapped in a polyelectrolyte/BSA complex due to strong electrostatic interaction between the protein and the polymer. The formulation #1 (A-MD NPs) have a diameter of about 20 nm to about 200 nm. Preferably, the nanoparticles of the formulation #1 have a diameter of about 50 nm, with a negative charge of about −30 mV.

Formulation #2—TER-MD NPs.

The formulation #2 comprises a MD NPs stabilized with poly(allylamine hydrochloride) (PAH) and loaded in a denatured protein matrix crosslinked with a graft terpolymer, such as poly(methacrylic acid)-polysorbate 80-starch (TER).

The formulation #2 can be prepared by any method known in the art the MD NPs stabilized with PAH are loaded into a matrix composed of denatured BSA crosslinked with a graft poly(methacrylic acid)-polysorbate 80-starch (TER). BSA is denatured by heating and ultrasonication (100 Hz) at 80° C. in the presence of the A-MD NPs followed by addition of activated TER polymer to crosslink the protein matrix through the covalent conjugation of the carboxylic groups of the TER polymer with amine groups of the BSA using EDC/NHS chemistry. The nanoparticles of the formulation #2 have about 50-250 nm in diameter and negative charge (~35 mV).

There are several advantages of the formulation #2. For example, the formulation #2 has the ideal size and charge for in vivo applications (100-150 nm and −35 mV); popcorn-like shape allows for better tumor penetration; can be dissociated in vivo forming smaller particles; can be further functionalized with different molecules via the —OH or —COOH groups on the terpolymer, e.g. tumor targeting peptide/antibody, fluorescent and near infrared dyes etc.; has high colloidal stability under physiological conditions; is highly reactive towards endogenous hydrogen peroxide; produces fast and high oxygen generation; has no cytotoxicity (100% cancer cell viability); has no acute or chronic toxicity to mice (via intravenous injection); intratumoral or intravenous use; and has a potential to enter brain tumor through the PS 80 in the terpolymer.

Formulation #3—PEG-TER-MD NPs:

The formulation #3 comprises a MD nanoparticle stabilized with PAH and loaded in a denatured protein matrix crosslinked with TER and a third layer of a melted lipid-PEG (polyoxyethylene stearate) coated on the crosslinked denatured TER-protein matrix.

One example of making the formulation #3 includes adding a melted lipid-PEG (polyoxyethylene stearate) during the nanoparticle preparation described above prior to adding the crosslinker (TER). In some embodiments, PEG has chain of about 2 kDa to about 10 kDa. The lipid-PEG forms a hydrophilic-like brush layer on the surface of the nanoparticle to improve the circulation time and accumulation in the tumor via intravenous injection. The nanoparticles of the formulation #3 are about 50 nm to 250 nm in diameter, and preferably about 180 nm in diameter and with a negative charge of about −32 mV. Like the formulation #2, the formulation #3 also can increase blood circulation time and generate better tumor accumulation.

Formulation #4—L-MD NPs:

The formulation #4 comprises a MD nanoparticle stabilized with PAH, a second layer of a hydrophobic molecule oleic acid covalently attached to the PAH, and a carrier of a solid lipid nanoparticle (L).

As an example of making the nanoparticles of the formulation #4, the aqueous MD NPs stabilized with PAH (pMD) are transferred to an organic phase attaching hydrophobic oleic acid (amine groups of polyelectrolyte present on the surface of pMD NPs covalently attached with carboxylic group of oleic acid using DDC chemistry). Hydrophobic nanoparticles are then loaded into a solid lipid nanoparticle (L) composed of myristic acid and PEG-lipid (polyoxyethylene stearate). This formulation consists of nanoparticles about 50-250 nm in diameter. Preferably, the nanoparticles are 180 nm in diameter and negatively charged (about −25 mV).

There are several advantages of formulation #4. For example, the formulation is comprised of endogenous lipids and a pharmaceutical excipient as the building material and as such, is anticipated to be in a good position to quickly obtain regulatory approval; preparation is simple; it is of a suitable size and charge for in vivo applications (e.g. 150 nm and −30 mV); it results in NPs that are spherical; it has high colloidal stability under physiological conditions; it can be further functionalized with different molecules (polyethylene glycol (PEG), tumor targeting peptide, fluorescent and near infrared dyes etc.); it has been shown to produce slow, continuous oxygen generation for prolonged modulation of the tumor microenvironment; it has no cytotoxicity (100% cancer cell viability); it has no acute or chronic toxicity to mice (via intravenous injection); intratumoral or intravenous use; and it has prolonged blood circulation and fast and high tumor accumulation (1-4 h post intravenous injection).

Formulation #5—PMA-MD NPs:

The formulation #5 comprises a MD nanoparticle stabilized with PAH (pMD), a second layer of oleic acid through covalent linkage with PHA, and a carrier of a grafted amphiphilic polymer (PMA)

As an example of making the nanoparticles of the formulation #5, the aqueous pMD transferred to an organic phase as described in Formulation #4. The hydrophobic nanoparticles are then emulsified with a grafted amphiphilic polymer (PMA), such as poly(isobutylene-alt-maleic anhydride)-hexadecylamine. After these steps, the nanoparticles of the formulation #5 are formed with a diameter of about 50 nm to 250 nm. Preferably, the nanoparticles are 130 nm in diameter and negative charge of about −30 mV.

There are several advantages of the advantages of the formulation #5. For example, this formulation can be simply prepared with suitable size and charge for in vivo applications (e.g. 150 nm and −30 mV); it is spherical; has high colloidal stability under physiological conditions; can be further functionalized with different molecules (polyethylene glycol (PEG), tumor targeting peptide, fluorescent and near infrared dyes etc.); generates slow, continuous oxygen generation for prolonged modulation of the tumor microenvironment; has no cytotoxicity (100% cancer cell viability); has no acute or chronic toxicity to mice (via intravenous injection); has intratumoral or intravenous use; and has prolonged blood circulation and fast and high tumor accumulation (1-4 h post intravenous injection).

In sum, while all five formulations have been found to be useful to treat cancer by enhancing the anti-tumor effectiveness of radiation therapy for cancer, they may have different chemical, physical or therapeutic properties. For example, although the size and surface chemistry of the nanoparticles can be tailored for intratumoral (i.t.) or intravenous (i.v.) injections, the inventors further found that the formulations #2 to #5 are highly stable in normal saline and medium (for example, in 10-50% FBS) and therefore are particularly suitable for both intratumoral and intravenous applications. Also, although all formulations #1 to #5 are able to generate oxygen by reaction with endogenous levels of hydrogen peroxide, higher oxygen generation rates are obtained with hydrophilic formulations, #1, #2, and #3. Moreover, compared with other formulations, formulations #4 and #5 show better tumor accumulation. Thus, one skilled in the art can determine and choose the most suitable formulation depending on the need in a specific case.

In an aspect, the present disclosure provides methods of treating cancer disease in a subject by administering an effective amount of a multifunctional nanoparticle composition described above.

The methods are based on the inventors' discovery that the compositions themselves have exhibited tumor inhibitory effect and antiangiogenic effect. Specifically, when administered to a tumor, the compositions disclosed herein can reduce hypoxia and acidosis of the tumor tissue microenvironment. The compositions can also down-regulate the expression of the master regulators of tumor progression and aggressiveness including hypoxia-inducible factor-1 alpha (HIF-1α) and vascular endothelial growth factor (VEGF) in the tumor tissue.

A "subject" used herein refers to a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Preferably, the subject is a mammal. The mammal can be a human, non-human primate, mouse, rat, dog, cat, horse, or cow, but are not limited to these examples. A subject can be male or female.

"Treatment of cancer" or "treating cancer" used herein refers to an activity that prevents, alleviates, maintains or ameliorates any of the primary phenomena (initiation, progression, metastasis) or secondary symptoms associated with the disease. For example, the treatment may (1) kill cancer cells or reduce the size of the tumor, (2) inhibit tumor growth or metastasis, (3) decrease tumor growth rate or metastasis rate, or (4) control the size of the tumor or the development of metastasis. Preferably, the treatment can alleviate or lessen the cancer.

What amount of the composition is effective depends on various factors and is readily determinable within the skill of the art, such as by the attending physician based on cancer type, subject data, observations and other clinical factors, including for example the subject's size, body surface area, age, sex, the particular parvovirus to be administered, the time and route of administration, the tumor type and characteristics, general health of the subject, and other surgical and/or drug therapies to which the subject is being subjected for the disease.

Administration of the composition may be effected in different ways by, including, but not limited to, intravenous, intraperitoneal, subcutaneous, intramuscular, topical or intradermal administration. The route of administration in a specific case, of course, depends on various factors, such as the kind of therapy, the kind of tumor or disease, and the kind of nanoparticles contained in the composition. In certain aspects, the tumors described herein can be benign or malignant, and the treatments described herein can be for both types of abnormal tissues.

In some embodiments, the administration can introduce the compositions into target cells, tissues or organs of interest. This introduction can be achieved by using art-known methods and commercially available injection or administration systems. For example, the nanoparticles can be administered intravenously, intra-arterially, or locally to achieve specific loading in and around the target tissue. A preferred route of administration is intravenous or intratumoral administration.

The composition can be administered alone or in a combination therapy. For example, the composition can combined with treatments such as surgery, chemotherapy or other adjuvant treatment modalities. Particularly, the inventors found that a combination of the composition with ionizing radiation therapy has shown a significant decrease in tumor growth rates, an increase in DNA double-strand breaks (DSBs) and tumor cell death compared with ionizing radiation treatment alone. Thus, adding the composition(s) to radiation therapy can be used to enhance the anti-tumor effectiveness of the ionizing radiation and while modulating the tumor microenvironment as a result of the addition of the composition(s). Accordingly, the method may further comprise an additional step of applying ionizing radiation to the subject. Thus, the composition(s) enhancing a radiation treatment or exposure directed to a tissue, cell or a tumor in a subject may act synergistically with the radiation to cause apoptosis and necrosis of cancer cells. Radiation therapy can be delivered with spatial accuracy using methods such as intensity-modulated radiation therapy or stereotactic radiation therapy, which delivers the ionizing radiation mostly to the tumor volume, which allows for localized treatment while sparing surrounding healthy tissues. Radiation therapy can be delivered as single- and/or multi-fraction, and at all clinically acceptable and practiced dose ranges. Radiation therapy can include conventional x-ray irradiation and radioactive sources used clinically, including brachytherapy or other forms of localized ionizing radiation treatment.

When used in a combination with radiation therapy, the composition(s) can be administered simultaneously or non-simultaneously with radiation. Simultaneous administration means that the composition(s) and the radiation are administered at the same time or within a certain, short intervening period of time, such as within 1, 5 or 10 minutes. Non-simultaneous administration means that the administration of the composition is at various times relative to the application of radiation therapy. Preferably, the composition is administered prior to the application of radiation. This time period between the administration of the composition and the delivery of the radiation can vary from about 10 minutes to 7 days.

In some preferred embodiments, the composition is intravenously injected to the subject about 30 minutes to 24 hours prior to the radiation to allow the nanoparticles accumulation in the tumor. In other preferred embodiments, the composition is intratumorally injected to the subject about 5 minutes to about 3 hours, preferably about 30 minutes, prior to the radiation.

In a further aspect, the present disclosure provides a use of a multifunctional nanoparticle composition disclosed herein for the manufacture of a medicament for the treatment of cancer by enhancing the effectiveness of radiation directed to a tissue or a tumor in a subject.

The following examples are offered for illustrative purposes only, and are not intended to limit the scope of the present disclosure in any way. Indeed, various modifications of the disclosure in addition to those shown and described herein will become apparent to those skilled in the art from the foregoing description and the following examples and fall within the scope of the appended claims.

EXAMPLES

Abbreviations

Figure 1D:
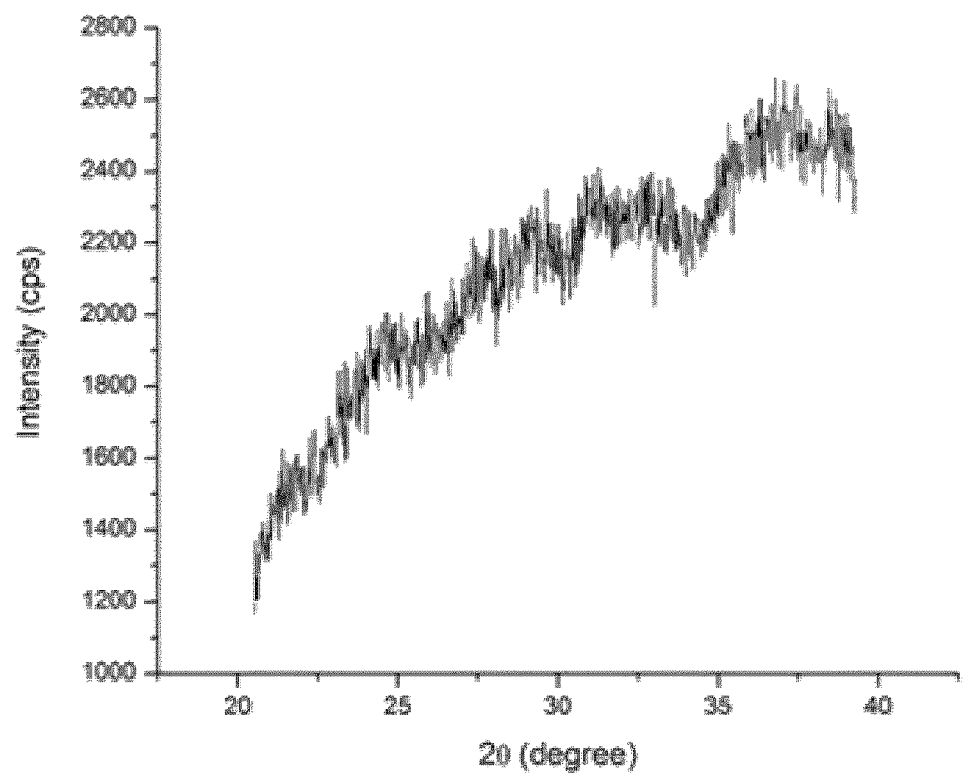
Figure 2A:
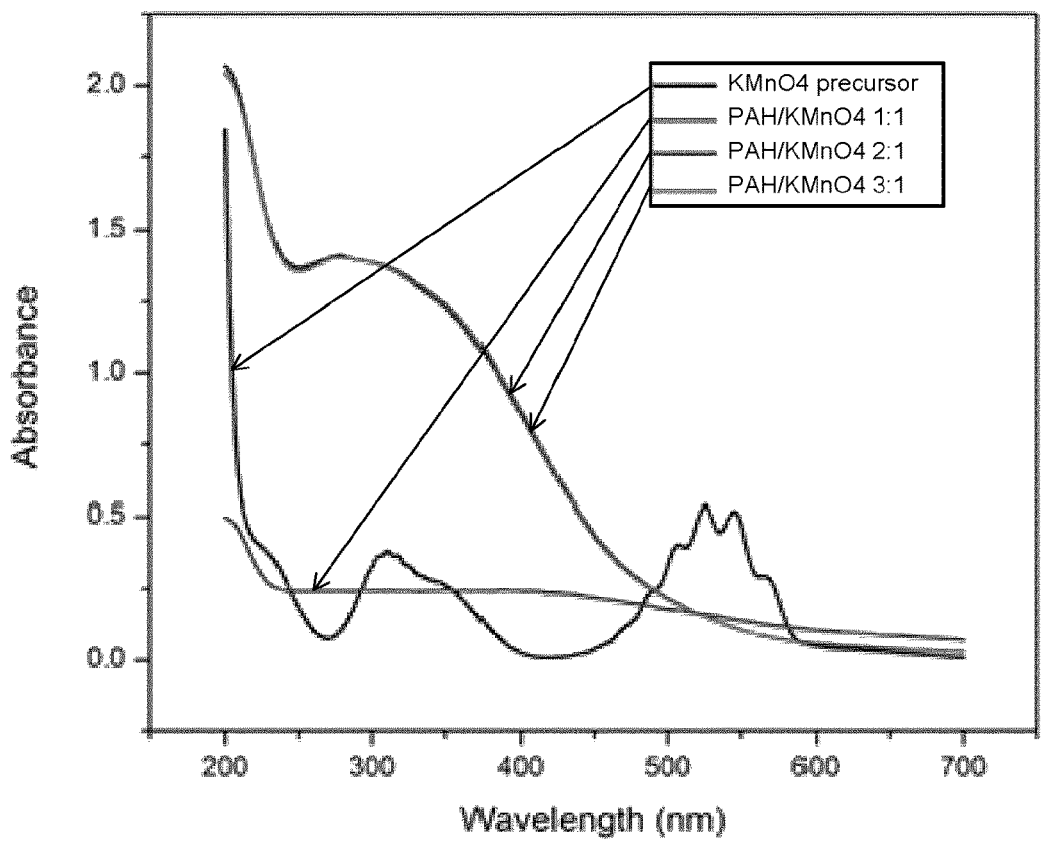
FIG. 2 shows characterization of polyelectrolyte-coated MnO$_2$ (pMD p=PAH or PARG) NPs and BSA-complexed A-MD NPs (a) UV-Vis absorption spectra of KMnO$_4$ solution and MD NPs prepared at various molar ratios between PAH and MD. (b) Effect of coating of pMD NPs with BSA on zeta potential for various BSA/NPs ratios. By adding BSA to a pMD NP aqueous suspension, the zeta potential of the NPs decreased from +30 mV to −25 mV. (c) and (d) Size distribution of pMD NPs before and after complexation with BSA.
Figure 2B:
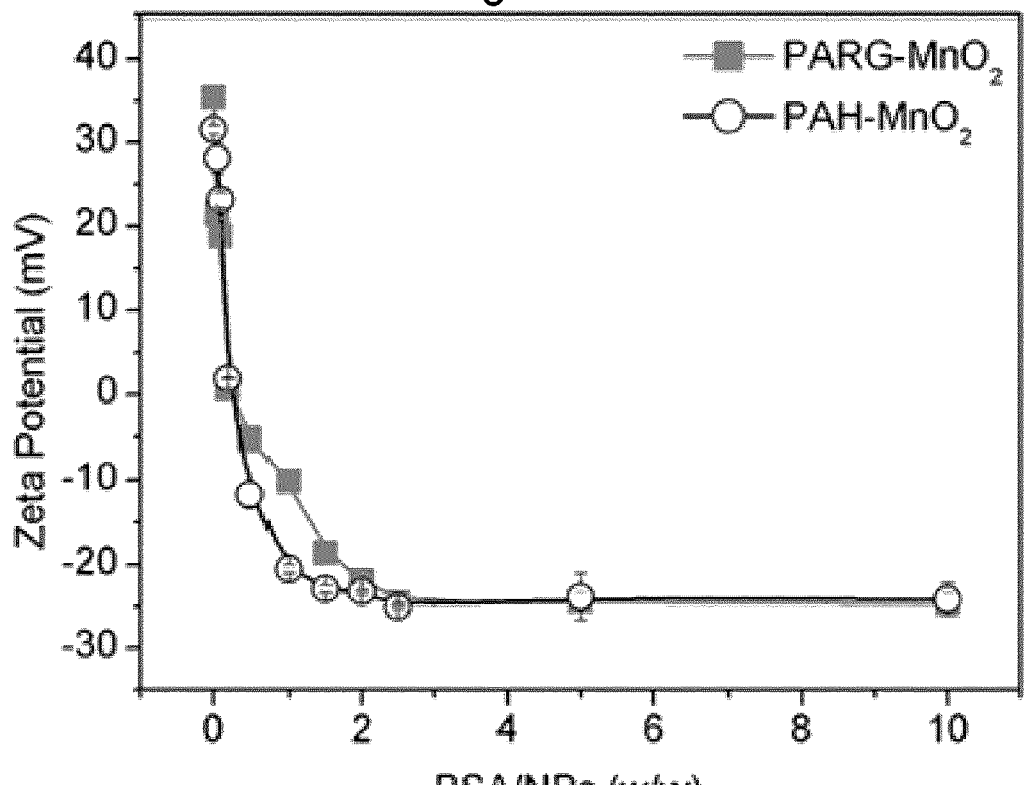
Figure 2C:
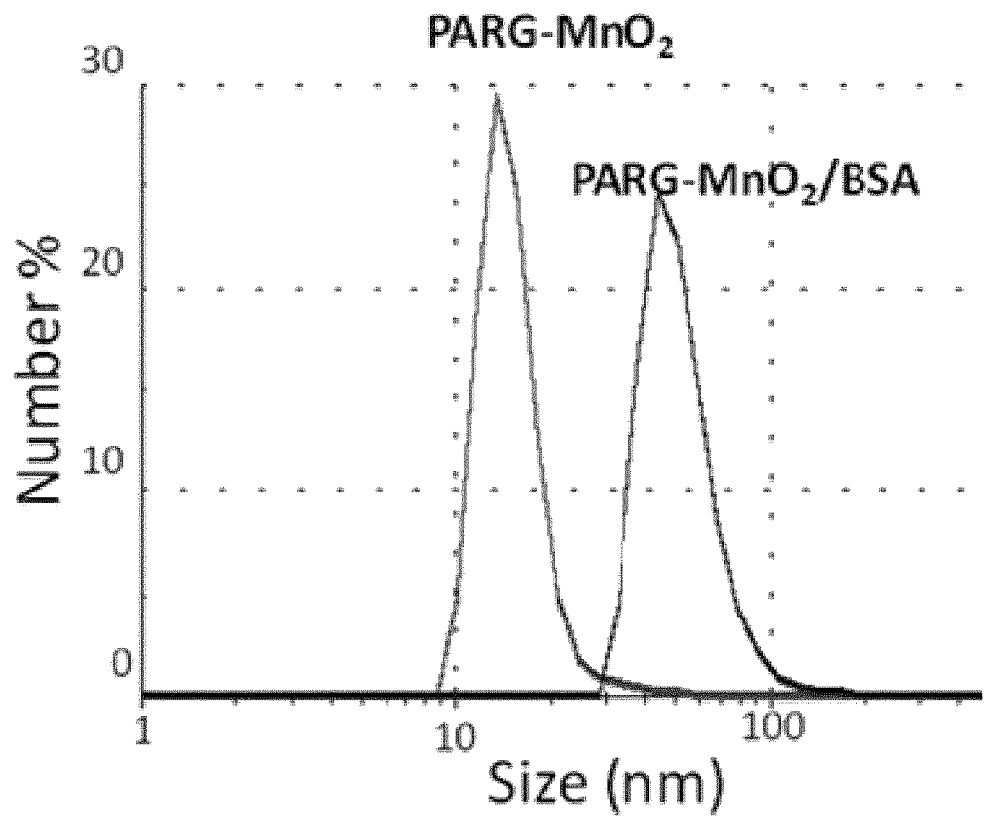
Figure 2D:
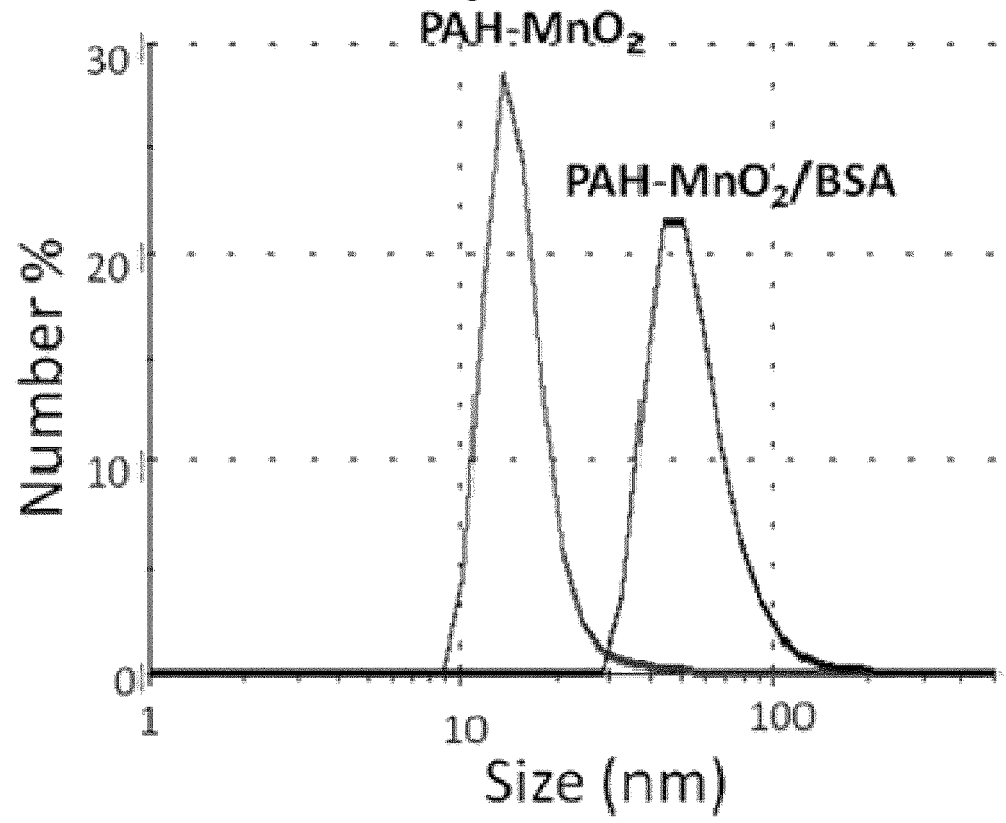

A-MD Albumin-based MD NPs prepared by complexation of pMD NPs with bovine serum albumin (BSA) or other proteins
ANOVA Analysis of variance
bMD Bare $MnO_2$ NPs
A-MD Albumin-based MD NPs prepared by complexation of pMD NPs with bovine serum albumin (BSA) or other proteins
BSA Bovine serum albumin
CT Chemotherapy
DSB Double strand break
DSWC Dorsal window chamber
FBS Fetal bovine serum
H&E Haematoxylin and eosin
HIF Hypoxia-inducible-factor
ICP Inductively coupled plasma
i.t. Intratumoral i.v. Intravenous
L-MD oMD NPs are loaded in lipid (i.e., myristic acid) and PEG based NPs
MD Manganese dioxide ($MnO_2$)
MSFI Multi spectral fluorescence imaging
MEM Minimal essential medium
MTT 3-(4,5-dimethylthiazol-2-yl)-2,5-diphenyltetrazolium bromide
NPs Nanoparticles
oMD pMD NPs are covalently conjugated with oleic acid
PA Photoacoustic
PAH Poly(allylamine hydrochloride)
PDT Photodynamic therapy
PMA Amphiphilic polymer (poly isobutylene alt maleic anhydride-Hexadecylamine)
PMA-MD oMD NPs are loaded in amphiphilic polymer PMA and PEG based NPs.
pMD $MnO_2$ NPs stabilized with a positively charged polyelectrolyte
ROS Reactive oxygen species
RT Radiotherapy
$sO_2$ Vascular saturated oxygen
TEM Transmission electron microscopy
TER-MD Terpolymer (TER) cross-linked denatured A-MD NPs with or without a polyethylene glycol (PEG)-like brush on the surface of the NPs.
TME Tumor microenvironment
TUNEL Terminal deoxynucleotidyltransferased UTP nick end labelling
VEGF Vascular endothelial growth factor
$H_2O_2$ Hydrogen peroxide
$MnO_2$ Manganese dioxide Example 1: Synthesis and Characterization of Bare $MnO_2$ (bMD) NPs A modified sonochemical reduction of permanganate with manganese ions was used to prepare bare MD NPs (bMD). A potassium permanganate aqueous solution (0.078 g in 10 mL of DDI water) containing a non-ionic surfactant Pluronic® F-68 (50 uL of 100 mg/mL solution) was kept under ultrasonic field for 30 s by using an ultrasonic processor probe operating at approximately 50 Hz (Heischer UP100H, Germany). Manganese acetate aqueous solution (0.18 g in 1 mL) was added and the dark brown dispersion obtained was sonicated for additional 30 s. Solid NPs were isolated by centrifugation (5,000 rpm for 10 min) and thoroughly washed with DDI water. The pallet was dispersed with 10 mL of DDI water and an aliquot of Pluronic® F-68 solution was added to the dispersion (50 uL, 100 mg/mL). Characterization of bMD NPs is shown in FIG. 1. The UV-Vis spectrum of the golden brown colloidal dispersion obtained showed a broad peak at 360 nm, a characteristic of colloidal MD NPs, indication of the formation of bMD NPs (FIG. 1a). Size distribution (FIG. 1b) and zeta potential measurements revealed NPs at about 80-100 nm and negatively charged (−18 mV). TEM images (FIG. 1c) revealed small like-flakes NPs with size distribution about 80 nm. X-ray powder diffraction (XRD) analysis of the particles revealed an amorphous structure of the bMD NPs (FIG. 1d).

Example 2: Synthesis and Characterization of Polyelectrolyte-Stabilized $MnO_2$ NPs (pMD)

pMD NPs were prepared following a one-step polyelectrolyte-based route by directly mixing potassium permanganate with a cationic polyelectrolyte aqueous solution such as poly(allylamine hydrochloride) (PAH) or polyarginine (PARG). In brief: In a small glass vial 18 mL $KMnO_4$ solution (3.5 mg/mL) was mixed with 2 mL of a polyelectrolyte solution in DDI water (37.4 mg/mL for PAH and 18 mg/mL for PARG, with a molar ratio 2:1 of polyelectrolyte's repeating unit). The mixture was left for 15 min at room temperature until all permanganate was converted to MD, determined by absorbance measurements. NPs were washed three times with doubly distilled (DDI) water using ultracentrifugation (50 k rpm for 1 hr). This step led to small (10-15 nm) pMD NPs stabilized with the polyelectrolyte. The absolute concentration of MD molecules in the NPs solution was quantified by inductively coupled plasma (ICP) analysis to determine the concentration of $Mn^{2+}$ ions, and thereby the concentration of pMD in the emulsion. A typical preparation produced a solution containing ~25 mM pMD. This synthesis procedure is rapid, reproducible and gives stable pMD colloidal dispersions. Characterization of the pMD NPs is shown in FIG. 2. The UV-Vis spectra of the $KMnO_4$ precursor solution and pMD NPs prepared at various molar ratios between PAH and MD are compared in FIG. 2a. After the reaction with PAH at ratios 2:1 and 3:1, the $KMnO_4$ peaks (315, 525 and 545 nm) disappeared, and a new broad peak around 300 nm was originated for these samples, an indicative of the formation of pMD NPs. The new peak around 300 nm is attributed to the surface plasmon band of pMD NPs. Zeta potential analysis (FIG. 2b) and size distribution measurements (FIGS. 2c-d) revealed NPs positively charged (+45 mV) at about 10-15 nm. The polyelectrolyte used served not only as a reducing reagent to reduce permanganate to MD, but also as a protective layer to stabilize as-formed NPs due to electrostatic repulsion.

Example 3: Preparation and Characterization of $MnO_2$ NPs Loaded into a Protein/Polyelectrolyte Matrix (A-MD)

Preparation of A-$MnO_2$ NPs

Figure 3A:
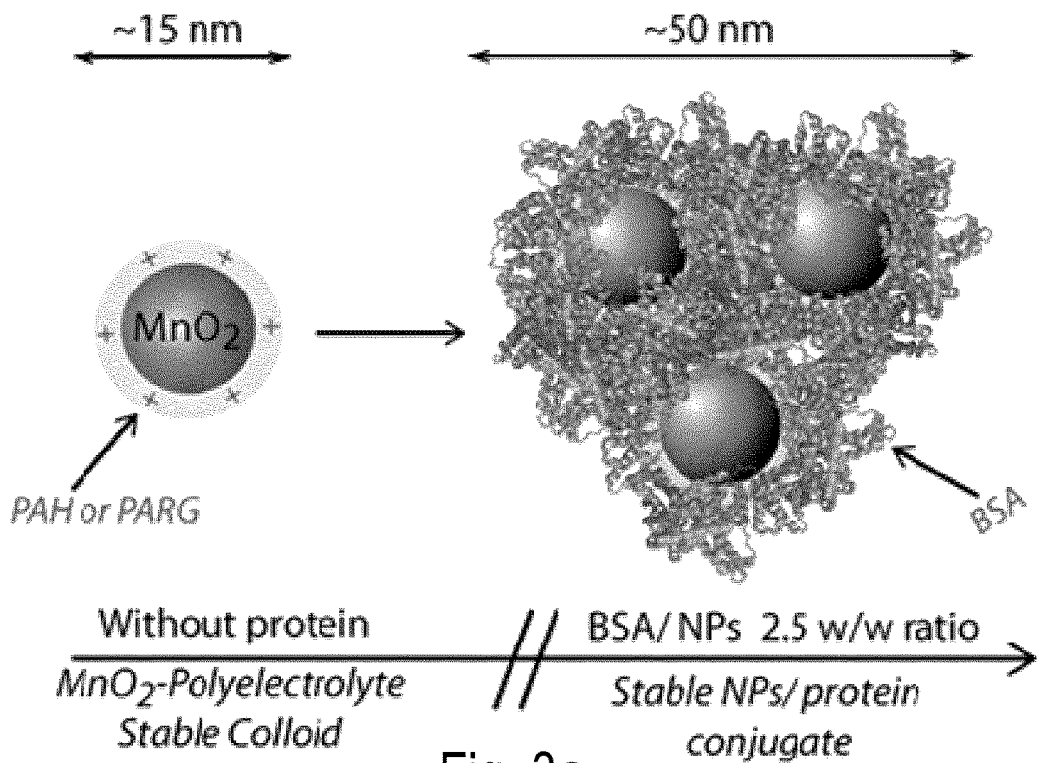
FIG. 3 shows (a) diagram and (b) TEM images of polyelectrolyte-coated MnO$_2$ (pMD) NPs and BSA-complexed A-MD NPs. MD NPs (~15 nm) are stabilized by positively charged polyelectrolyte (PAH or PARG). In A-MD (~50 nm), several MD particles are entrapped in a PAH/BSA or PARG/BSA complex due to strong electrostatic interaction between the protein and the polymer. The scale bars in the TEM pictures correspond to 100 nm.
Figure 3B:
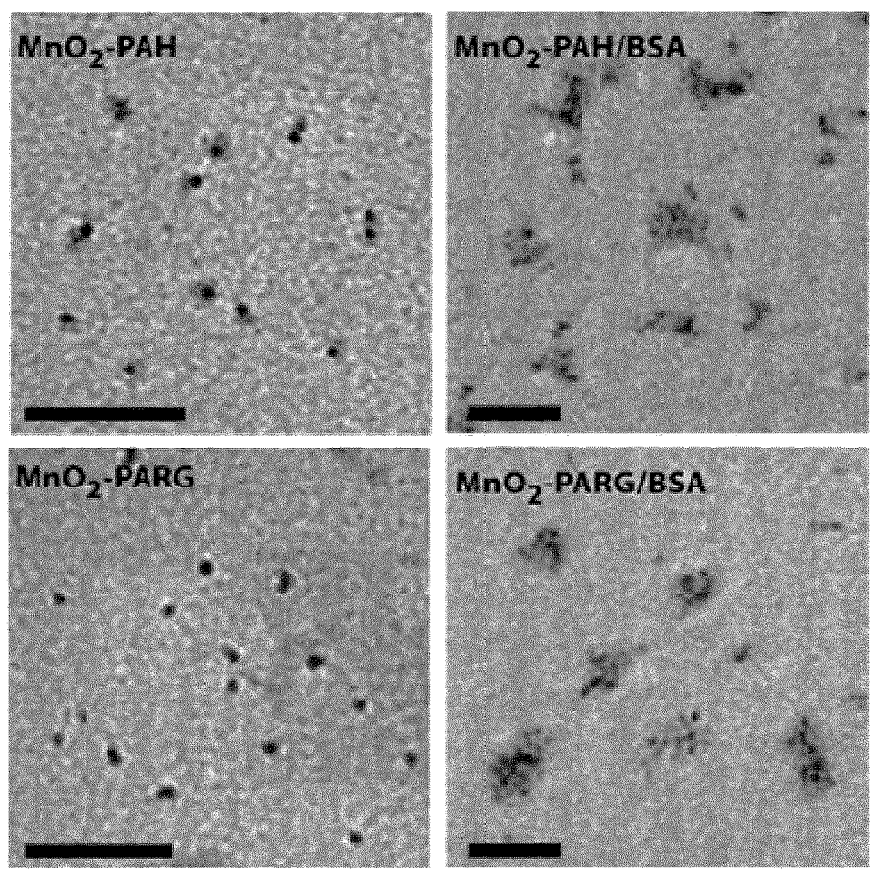
Figure 4A:
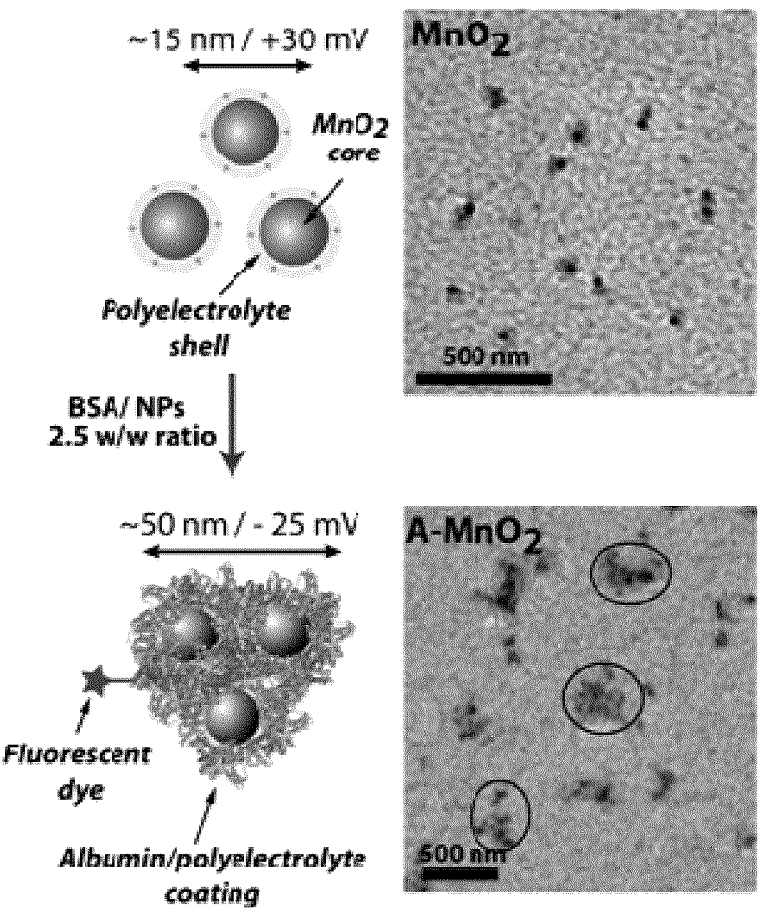
FIGS. 4a-d show the characterization of A-MD NPs: (a) Diagram & TEM images of MD and A-MD NPs. Precursor pMD NPs (~15 nm) are stabilized by positively charged PAH. In A-MD (~50 nm) several MD particles are entrapped in a PHA/BSA complex due to strong electrostatic interaction between the protein and the polymer. (b) Size distribution of NPs. (c) Effect of coating of pMD NPs with BSA on zeta potential for various BSA/NPs ratios. By adding BSA to a pMD NP aqueous suspension, the zeta potential of the NPs decreased from +30 mV to −25 mV. (d) Picture of pMD NPs (left) and A-MD NPs (right) (1 mM) in various aqueous media: DDI water, normal saline (0.9% NaCl) and αMEM cell medium containing 10% fetal bovine serum (FBS). pMD NPs undergo aggregation in saline or cell culture medium, while A-MD NPs are stable in these media. The red color observed in the vials comes from the pH indicator in the αMEM medium.
Figure 4B:
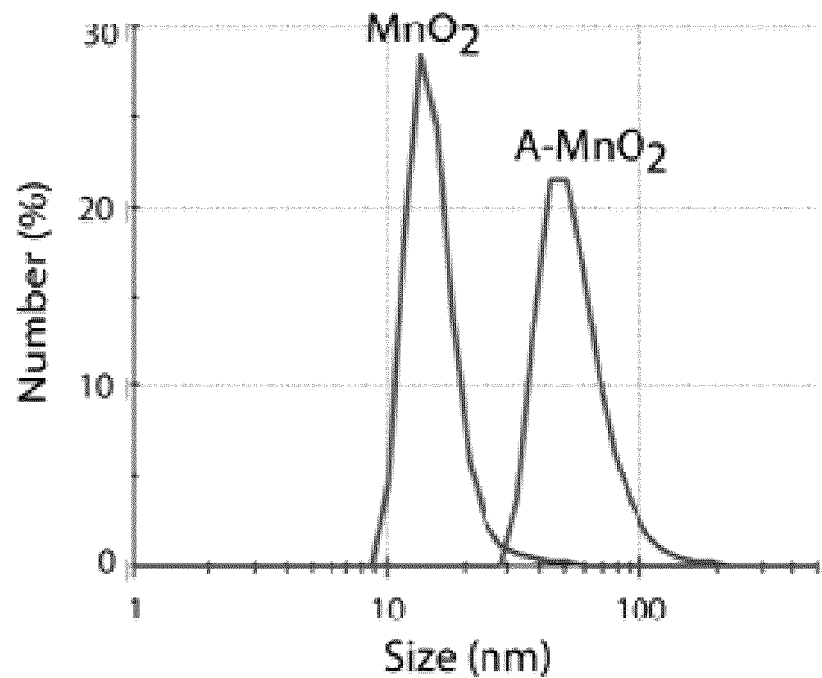
Figure 4C:
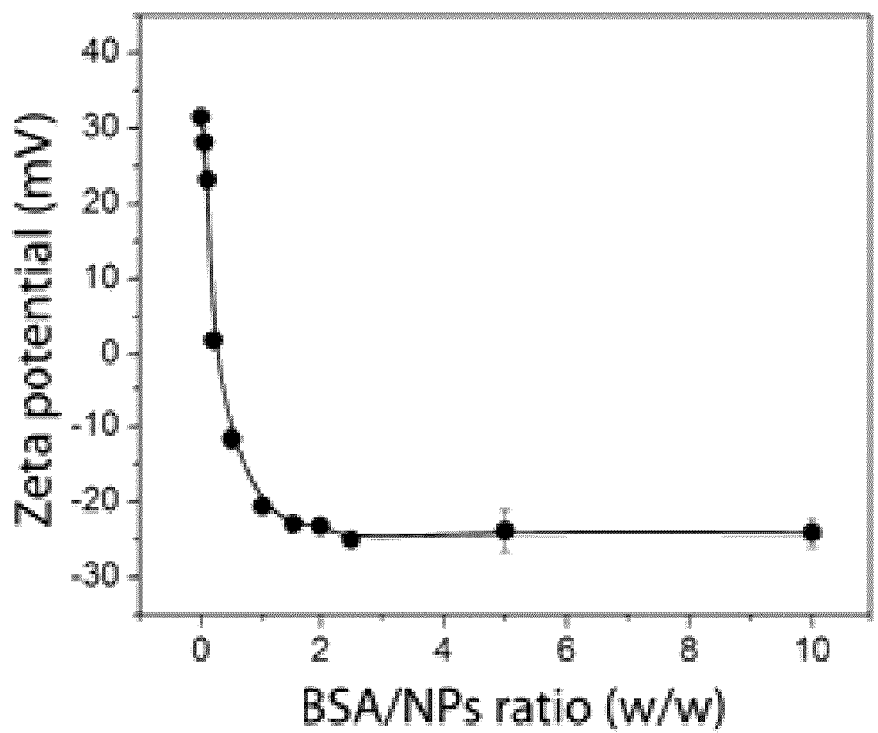

For the synthesis of NPs, the inventors employed a one-step method to reduce manganese permanganate ($KMnO_4$) to MD NPs with cationic polyelectrolyte poly(allylamine hydrochloride) (PAH). This synthesis procedure is rapid, reproducible and gives stable MD colloidal dispersions with an average NP size distribution of 15 nm (FIG. 4a-b). In the present synthesis method, the inventors were able to decrease by 50% the amount of PAH normally used in polyelectrolyte-based NPs synthesis.[21] The decrease in the amount of PAH utilized in the NP formulation is very important for in vivo applications, since cationic polyelectrolytes can show pronounced concentration-dependent cytotoxicity. The polyelectrolyte used here served not only as a reducing reagent to reduce $KMnO_4$ to MD, but also as a protective layer to stabilize as-formed NPs due to electrostatic repulsion (zeta potential +30 mV, FIG. 4c). In this formulation, pMD NPs were complexed with bovine serum albumin (BSA). BSA-$MnO_2$ (A-MD) NPs were prepared by directly mixing BSA with pMD NPs in aqueous medium. In brief, in a vial 4 mL of pMD NPs stock solution (25 mM) was diluted with 6 mL of normal saline solution (0.9% NaCl in DDI water). This diluted pMD solution (10 mM) was mixed with 1.2 mL of BSA solution in normal saline (10 mg/mL). This step led to the formation of A-MD NPs (~50 nm), with several pMD NPs entrapped in a polyelectrolyte/BSA complex due to strong electrostatic interaction between the protein and the polymer. A-MD NPs were further diluted with cell medium or sterile saline for in vitro and in vivo studies, respectively. Protein labelling kits AnaTag™ HiLyte Fluor™ 594 (Texas Red) and AnaTag™ 750 (AnaspecInc, USA) were used to label albumin for the preparation of red fluorescent and near-infrared NPs, respectively. It was estimated 100% loading of the pMD NPs in the polyelectrolyte/BSA complex. UV-Vis spectrophotometry analysis of the supernatant indicated the absence of free pMDNPs in the supernatant after ultracentrifugation (10 k rpm, 10 min) of the NP emulsion. The A-MD NPs prepared were negatively charged (−25 mV) (FIG. 2b) and approximately 50 nm in size (FIG. 2c-d), and stable in alpha minimal essential medium (αMEM) cell medium and saline. TEM pictures (FIG. 3b) show several small pMD NPs within the protein/polymer complex.

Figure 4D:
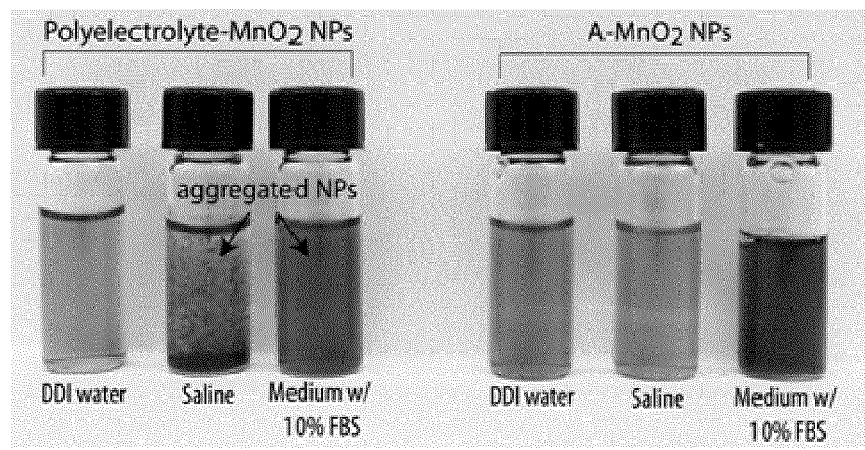

To formulate MD NPs for biomedical in vivo applications the inventors took into account the issues of nanoparticle stability, size control and toxicity. For biological applications, NPs must be stable in cell culture medium or normal saline required for in vitro and in vivo studies, respectively. Polyelectrolyte-coated $MnO_2$ (pMD) nanoparticles are too small and positively charged, which can cause high instability in cell medium or saline and result in toxicity. To solve these problems, the inventors have conjugated small polyelectrolyte-coated $MnO_2$ nanoparticles with bovine serum albumin (BSA) and obtained particles of suitable size, charge, colloidal stability and biocompatibility for in vitro and in vivo applications, while maintaining the MD reactivity towards $H_2O_2$ for the production of oxygen and increase in pH. BSA can form stable non-covalent complexes with cationic polyelectrolytes,[31] leading to lower NP toxicity.[32] The prepared A-MD NPs were approximately 50 nm in size (FIG. 4b), negatively charged (−25 mV) (FIG. 4c) and stable in alpha minimal essential medium (αMEM) cell medium and saline (FIG. 4d), making them suitable for in vivo applications. The albumin coating also provided the NPs with different surface charge and chemistry allowing the inventors to further functionalize the NP surface with protein-reactive fluorescent dyes such as Texas Red™ (excite 596/emit 617 nm) and amine-reactive near infrared dye (excite 754/emit 778 nm). These fluorescence-labelled NPs were utilized in our subsequent in vitro and in vivo studies.

Multifunctionality of A-MD NPs in Culture Medium

Figure 5A:
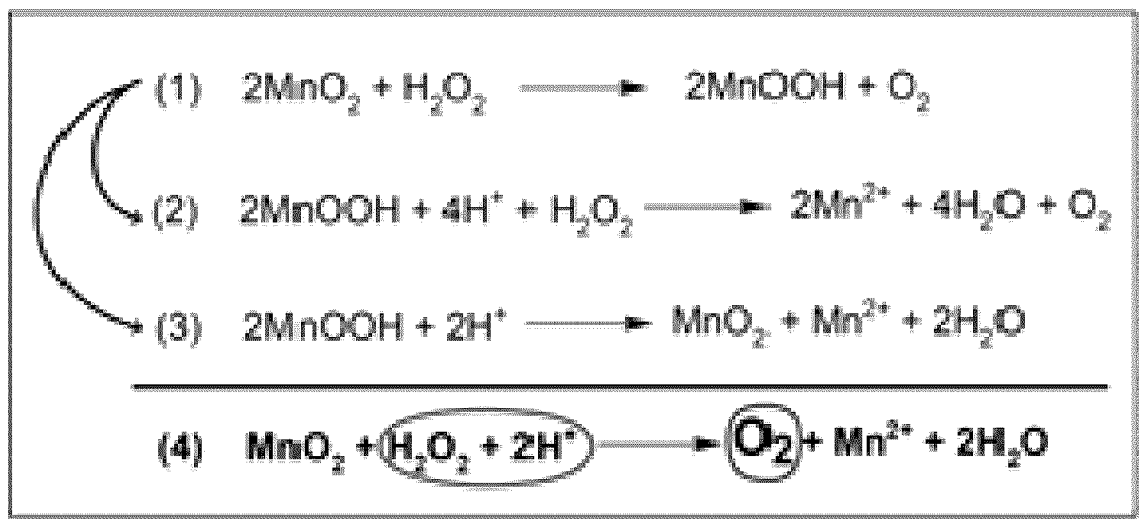
FIGS. 5a-e show the in vitro reactivity of A-MD NPs towards hydrogen peroxide. (a) Reaction scheme showing the reactivity of MD towards H$_2$O$_2$ for the production of O$_2$ and removal of protons. (b) Quenching of endogenous level H$_2$O$_2$ (1 mM) by A-MD NPs (45 μM). (c) Oxygen generation at various A-MD NP contents (numbers indicate MD in μM). (d) Simultaneous O$_2$ generation and pH increase vs. time by the A-MD NPs. (e) O$_2$ generation by addition of H$_2$O$_2$ to an A-MD NP suspension. All experiments were performed (n=3) in cell culture medium containing 10% FBS at 37° C. Error bars are standard error of the mean.
Figure 5B:
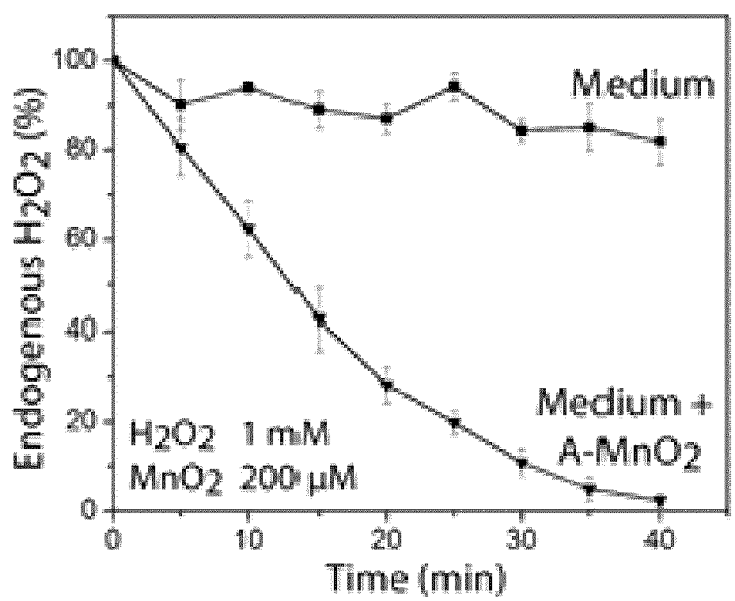
Figure 5D:
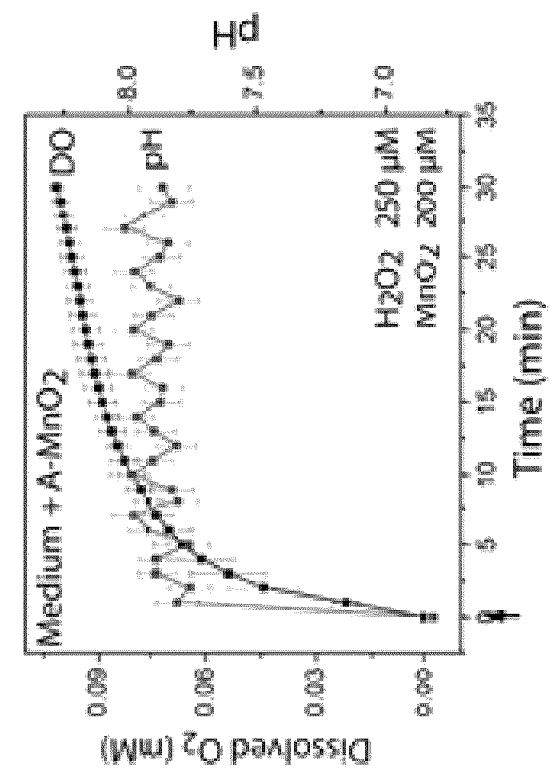
Figure 5C:
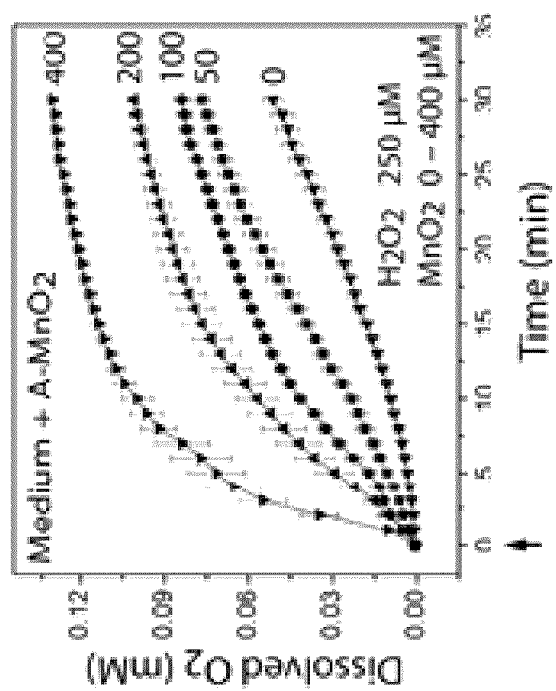
Figure 5E:
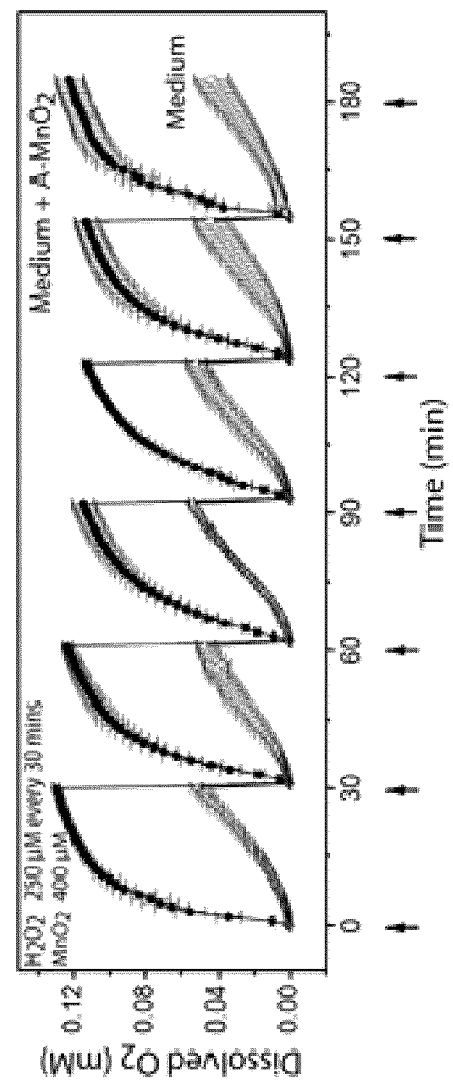

The inventors first investigated the multifunctionality of the A-MD NPs to generate $O_2$ and to increase the medium pH in vitro upon reaction with $H_2O_2$ at endogenous levels. The reaction between MD and $H_2O_2$ is a complex reaction leading to the decomposition of $H_2O_2$ and the production $O_2$ as summarized in FIG. 5a. Besides the production of $O_2$, the reaction causes an increase in the local pH by the consumption of $H^+$ ions and the production of an intermediate Mn-oxo-hydroxide (MnOOH).[26] This phenomenon can be particularly useful for the regulation of local pH in cancer cells and tumour tissue. Hence the inventors studied if A-MD NPs would generate measurable amounts of oxygen and increase pH at low concentrations of $H_2O_2$ found in the human body (i.e., 100 µM and up to 1 mM).[33] The inventors found that at a very low concentration (~45 µM of MD), the NPs were able to completely quench 1 mM $H_2O_2$ in cell medium within 40 minutes (FIG. 5b). The inventors further investigated the $O_2$ generating properties of the NPs using an in-house-made hypoxia-maintaining chamber coupled with both a commercially available oxygen probe and a pH microelectrode. Significant amounts of $O_2$ were produced (FIG. 5c) accompanied by an increase in the pH of physiological buffer (phosphate/saline buffer) by one pH unit from pH 6.8 to pH 7.8 (FIG. 5d) by the reaction of 45 µM of MD with 250 µM $H_2O_2$. In an attempt to simulate in vivo conditions where $H_2O_2$ is continuously generated by tumor cells, the inventors measured the $O_2$ production by the NPs during the continuous addition of exogenous $H_2O_2$ (250 µM) into the chamber every 30 min. The inventors observed that a single dose of the NPs (90 µM MD) continuously generated $O_2$ for at least 6 cycles of 30 min each (FIG. 5e). These results demonstrated that $H_2O_2$ and protons can diffuse rapidly across the polyelectrolyte-albumin complex, access the reactive sites of the $MnO_2$ cores, produce $O_2$ and increase pH in a sustained manner under hypoxic conditions.

In Vitro Studies with Cells

The viability of human breast cancer MDA-MB 231 and murine breast cancer EMT6 exposed to various concentrations of MD NPs for 48 h was evaluated. In brief, platted cells (10 000 cells per well/96 well plate) were incubated with different NP formulations dispersed in α-medium at desired concentrations (i.e., for 50 and 100 uM MD). Cells were incubated with NPs for 48 h and assayed following a standard MTT colorimetric assay protocol.

Cellular Uptake of NPs:

Murine EMT6 breast tumor cells ($10^5$ cells) were incubated for 1 h with A-MD NPs (45 µM) at 37° C. before microscopic analysis. Cell uptake of NPs by transmission electron microscopy (TEM) was performed using a H7000 TEM microscope (Hitachi, Japan), following standard methods for sample preparation. An EVOS fluorescence microscope (AMG, USA) was used to image live cells following incubation with red fluorescent dye labelled A-MD NPs. Cell nuclei were stained blue with HOESCHT 33342 (Invitrogen Molecular Probes, USA). The cellular uptake of NPs at various time points was also evaluated. For this experiment, NPs were made fluorescent by loading of fluorescein isothiocynate (FITC) to the NPs as previously described. Platted cells (500,000 cells per well/6 well plate) were incubated with FITC labelled A-MD NPs dispersed in culture medium at the concentration 100 µM MD. Cells were incubated with NPs for several time points: 0.5, 1, 2, 4 and 24 h. After incubation time cells were washed twice with PBS, trypsinized and replated in 96-well plate (10,000 cells per plate). Fluorescence was measured with a microplate reader, ex: 485 nm and em: 520 nm.

These results are summarized in FIG. 6. Cell viability studies showed that all formulations (protein, lipid and polymer based) are not toxic to the cancer cells at MD concentrations used in vitro and in vivo (i.e., 100 µM MD) (FIG. 6a-c). It is known that the aberrant metabolism of cancer cells leads to significantly elevated cellular concentrations of $H_2O_2$. If the NPs could be taken up by cancer cells, they could react quickly with endogenous $H_2O_2$ produced by cancer cells under hypoxic stress, thus producing $O_2$ in situ. To test this hypothesis, the inventors first examined the cellular uptake of the NPs by incubating EMT6 murine breast cancer cells with fluorescence-labelled A-MD NPs, and observed significant cellular uptake of NPs within 60 min of incubation (FIG. 6d). This finding was confirmed by transmission electron microscopy (TEM). TEM images (FIG. 6e) showed EMT6 cells in vitro underwent membrane invagination and engulfment of the NPs and the NPs taken up by the cell were distributed within the cell cytoplasm and vesicles after 1 h incubation. Different formulations showed similar cellular uptake profile over the time for two different cancer cell lines (FIG. 6f-g). Cellular uptake of the NPs was observed within 60 min of incubation with EMT6 cells (FIG. 6f).

Oxygen Generation in the Presence of Hypoxic Cancer Cells

The inventors found that the NPs incubated with hypoxic breast cancer cells could react quickly with endogenous $H_2O_2$ produced by the cells under hypoxic stress, thus producing $O_2$ in situ (FIG. 6f). Significant amounts of $O_2$ (~6-fold increase of $O_2$ levels in the medium) were detected within 2 min by reacting with $H_2O_2$ released by the cancer cells (FIG. 6f). These results indicate that the endogenous levels of $H_2O_2$ released by hypoxic cancer cells in vitro is sufficient to react with the NPs and generate measurable $O_2$ without addition of exogenous $H_2O_2$ to the culture medium. Moreover, at the concentration used for in vitro $O_2$ generation (45 μM MD), A-MD NPs showed relatively low cytotoxicity to EMT6 cancer cells (~80% cell viability) (FIG. 6g). Based on these data, the inventors hypothesize that elevated levels of $H_2O_2$ in solid tumors could serve as a reactant for $O_2$ production in vivo.

Effect of A-MD NPs on Tumor Oxygenation

The effect of A-MD NPs on oxygen saturation within orthotopic murine EMT6 cell breast tumors was assessed with a small animal photoacoustic (PA) imaging system following intratumoral (i.t.) injection of 50 μL of A-MD NP suspension in saline. A Vevo LAZR Photoacoustic Imaging System (VisualSonics Inc., Canada) with a 21 MHz centre frequency transducer (LZ-550, VisualSonics Inc., Canada) was used to measure vascular oxygen saturation ($sO_2$) in situ over time before and after i.t. treatment with A-MD NPs. Ultrasound was utilized to guide NP injection in order to administer treatments to the tumor. Animals were maintained below 7% oxygen atmosphere during the experiment and $sO_2$ measurements were assessed using standard multi-spectral photoacoustic imaging in the tumors in vivo using two excitation wavelengths (750 nm and 850 nm) for deoxygenated and oxygenated hemoglobin, respectively.

Figure 7A:
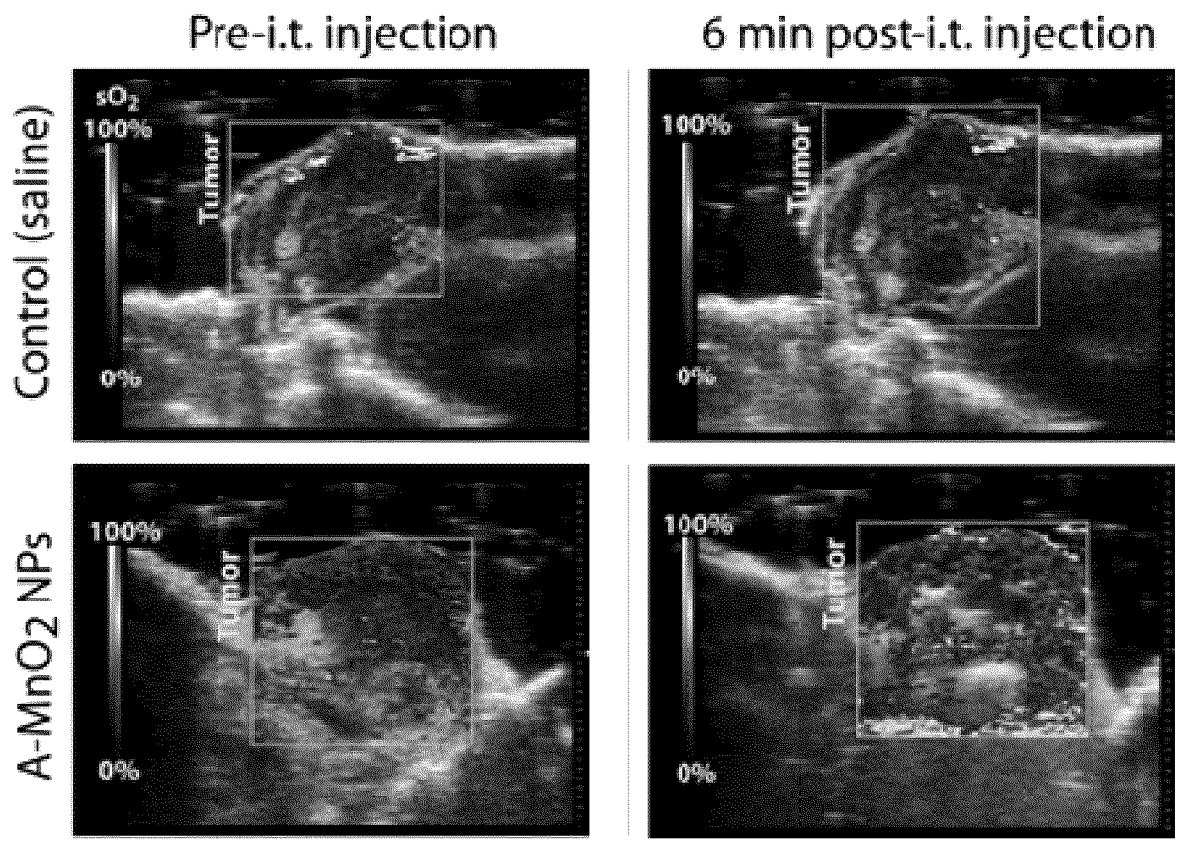
FIG. 7a-c show the effect of A-MD NPs on tumor oxygenation: (a) Representative 2D photoacoustic images of EMT6 solid tumors showing parametric map of estimated oxygen saturation (sO$_2$) pre- and post-i.t. injection of saline (control) or A-MD NPs. (b) Average total sO$_2$ in the tumor over time. (c) Comparison of average tumor sO$_2$ levels before and after treatments (n=3). Error bars represent standard errors of the mean. *=statistically significant increase (*p=1.8E-5) in sO$_2$ as compared to saline (control) treated group.
Figure 7B:
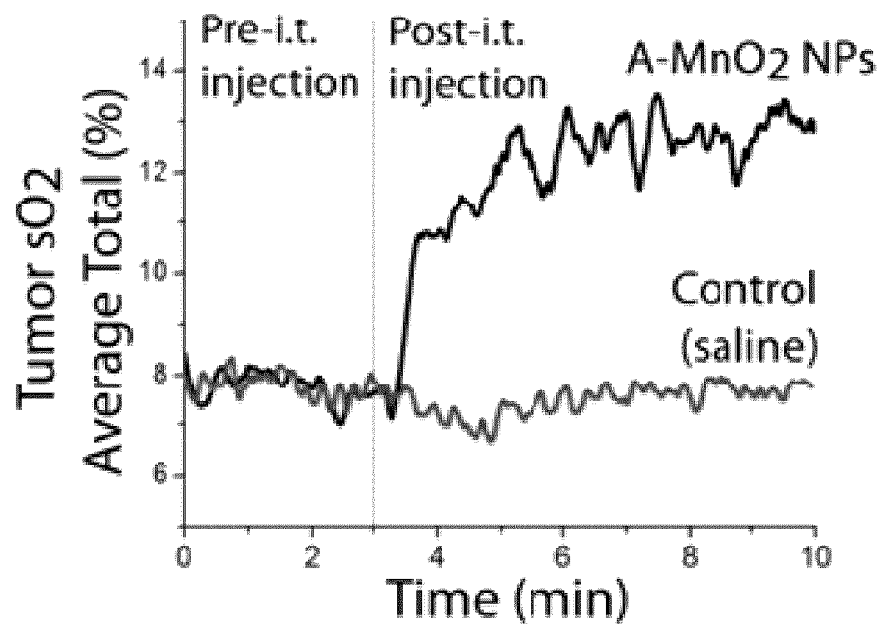
Figure 7C:
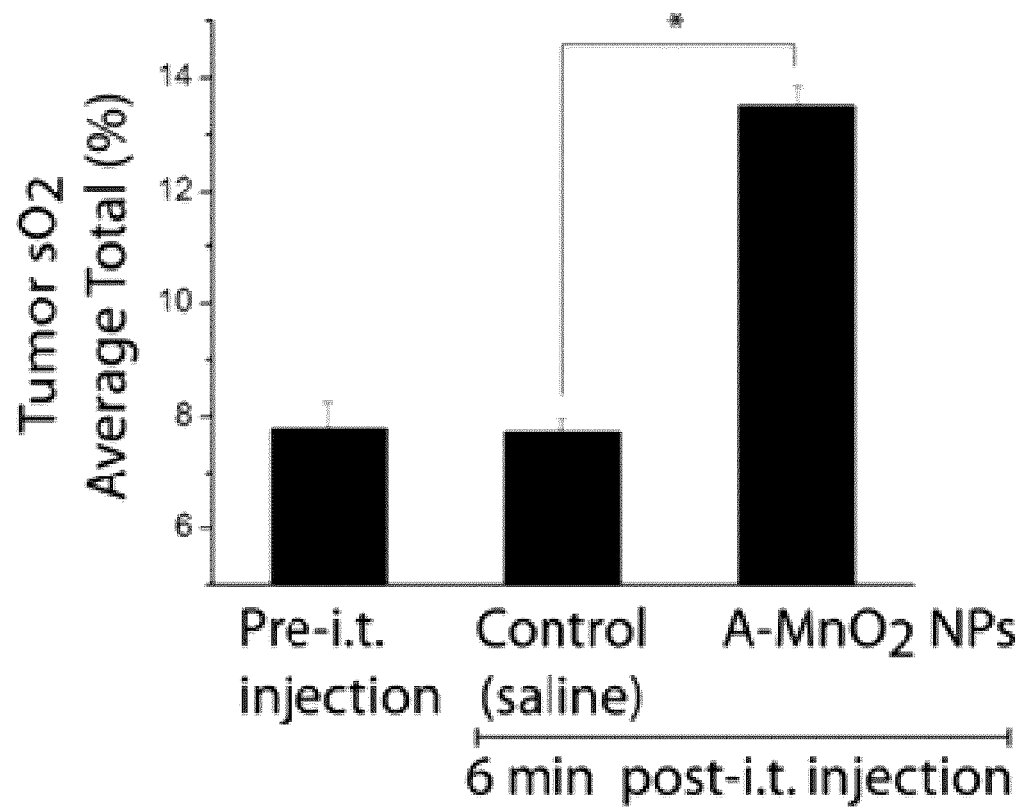

PA imaging measures vascular saturated $O_2$ ($sO_2$) by the differential optical absorption of oxygenated and deoxygenated hemoglobin at different wavelengths, which is directly correlated with changes in $O_2$ concentration in the blood[40]. To ensure similar localization of the NPs in each tumor we used ultrasound image-guidance to inject the NPs into the tumor in vivo. Since the blood vessels maintain a saturated level of oxygen under normoxic conditions, the mice were maintained under 7% $O_2$ during the experiments to visualize the enhancement of oxygen production by the A-MD NPs. Vascular $sO_2$ was measured before and after i.t. injections of A-MD NPs suspension or saline only (control) and found that $sO_2$ increased promptly by approximately 45% as compared with control tumors (FIG. 7 a-c). It is important to point out that PA imaging of $sO_2$ depends on the presence of blood flow, which is lacking in the necrotic and avascular tumor core. Thus, the PA images revealed $sO_2$ was mainly generated within the tumor periphery (FIG. 7a). However, this does not imply that the NPs are unable to produce $O_2$ in the hypoxic region close to the tumor core, as the $O_2$ generating capacity of the NPs is limited only by the presence of $H_2O_2$. Interestingly, the nearly immediate detection of $O_2$ at the tumor periphery suggests the rapid distribution of the NPs within the tumor mass from the injection site (i.e., tumor center) perhaps due to the interstitial pressure gradient with a higher pressure in the tumor core than within the peripheral region[41].

In this Example, the inventors used i.t. delivery of A-MD NPs for the assessment of the effect of the NPs on tumor oxygenation in vivo. The reason for using i.t. delivery is two-fold. Firstly, the local delivery method is better than systemic delivery (e.g. intravenous injection) in terms of uniformity of NP dose delivered to each tumor owing to a broad variation from tumor to tumor in morphology and NP penetration. Secondly, local intratumoral delivery of therapeutics has been emerging as an effective treatment of many types of localized operable and inoperable solid tumors (e.g. breast, colorectal, lung, prostate, skin, head and neck and brain tumors) due to its advantages over systemic methods, including dramatically higher local drug concentration, better therapeutic outcomes and minimal systemic toxic side-effects.[41, 42]

pKa Calibration for SNARF in Tissue Like Phantoms.

SNARF-4F 5-(and-6)-carboxylic acid (Life Technologies, USA, # S23920) is a dual imaging, pH-sensitive fluorophore that allows the measurement of pH values in solution as well as in biological tissue. The typical fluorescence emission spectra of SNARF shift from green-yellow to red when the pH changes from acidic to alkaline. The ratio between the two fluorescence intensities, typically at 580 nm and 640 nm, provides quantitative information about the pH values. For the quantitative measurement of pH using SNARF, calibration curves must be obtained under the similar conditions at which the pH values are to be determined as the pKa values of the dye are sensitive to the local environment. In the present studies, the calibration of SNARF was performed using tissue-like phantoms prepared in pH range 4-10, following an established protocol[55, 56].

In detail, buffers were prepared using the following buffering systems: potassium hydrogen phthalate/hydrochloric acid from pH 3-4, potassium hydrogen phthalate/sodium hydroxide from pH 4.5-6, potassium dihydrogen phosphate/sodium hydro oxide from pH 6-8 and disodium hydrogen phosphate/hydrochloric acid from pH 8-10. pH values for all buffers were measured using Acumet AB15 pH meter (Fisher Scientific, US).

Phantoms were prepared by heating 10% (wt/v) gelatin in deionised water at 50° C. Once gelatin melted, the temperature was reduced to 40° C. and haemoglobin (Sigma # H2625) and intra lipid (Sigma #1141) were added to give final concentration of 42.5 μM and 1% (wt/v), respectively. After few minutes of stirring, one part of gelatin solution was mixed with three parts of 1 mM SNARF solution prepared in different pH buffers (pH 4-10) with a pH increment of 0.5 unit. In a last step, 200 μL of the final mixture was transferred to a 96-well microplate and placed in fridge for solidification. Biological phantom were prepared in triplicate for each pH value. Fluorescence images of the microplates were recorded using a Xenogen microscope (Xenogen IVIS Spectrum, Caliper Life Sciences Inc., USA) with two different filter channels; the excitation wavelength for each channel was 535 nm whereas the emission intensities were recorded at 580 nm (green channel) and 640 nm (red channel).

Figure 8A:
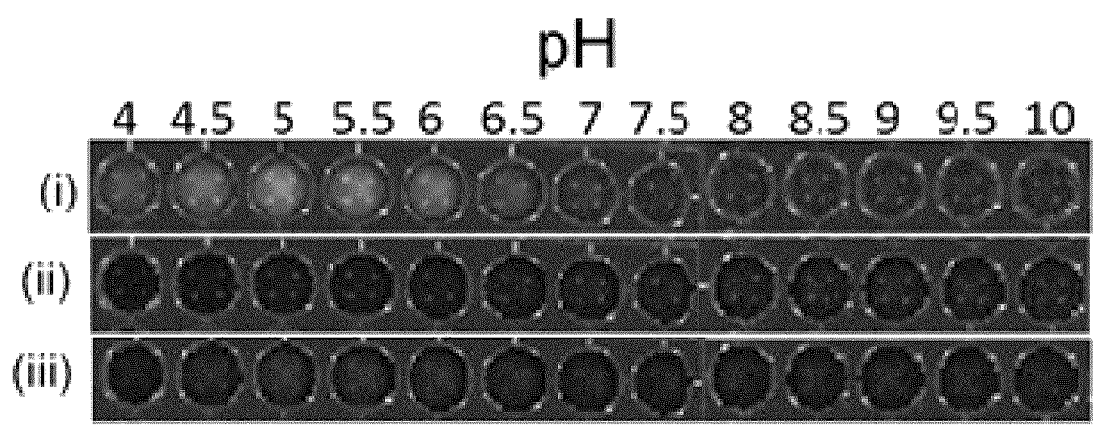
FIG. 8 graphically shows the calculation of pKa value for SNARF in biological phantoms. (a) Fluorescence images of SNARF-containing phantoms at different pH values, recorded using Xenogen microscope with a excitation wavelength of 535 nm (row (i) green channel, row (ii) red channel and row (iii) is overlay of the two channels). (b) Graphical representation of the ratios (R=I$_g$/I$_r$) versus pH where the ratio R was calculated from the values I$_g$ and I$_r$ which were obtained from fluorescent images in (a) using image-J program. (c) The Boltzmann fit of data points R using Eq. 1, where the values for fit parameter were R$_a$=1.47, R$_b$=0.60, pH$_{infl}$=6.25, and ΔpH=0.3. (d) Graphical representation of −log( . . . ) term versus pH, where the ratio R was obtained from the Boltzmann fit in (c) and I$_{a(\lambda 2)}$ and I$_{b(\lambda 2)}$ are fluorescence intensities at 640 nm (red channel) obtained from images provided in (a) at pH 4.5 and pH 8.5 using image-J program, I$_{a(\lambda 2)}$=41.92 and I$_{b(\lambda 2)}$=63.11. (d) Graphical representation of the intercept of linear fit of data points where pKa was calculated according to Eq. 2. The obtained pKa of SNARF was 6.39.
Figure 8B:
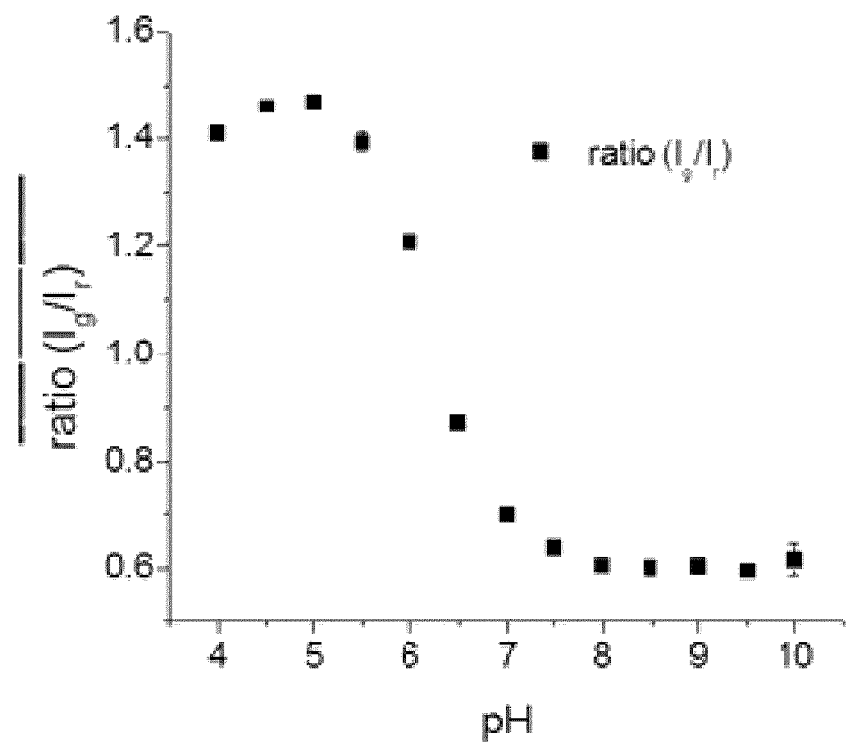
Figure 8C:
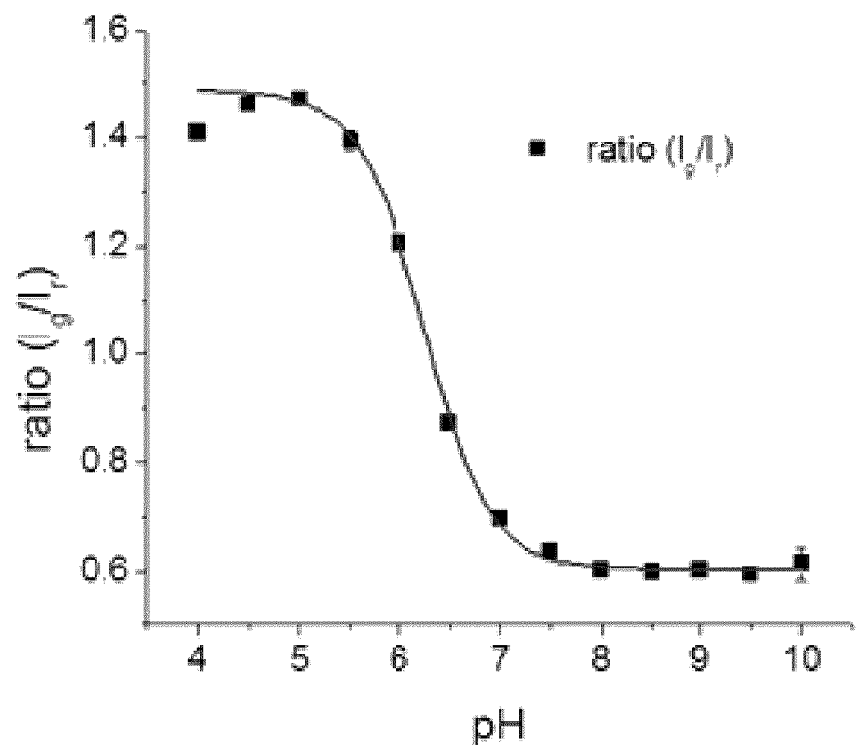
Figure 8D:
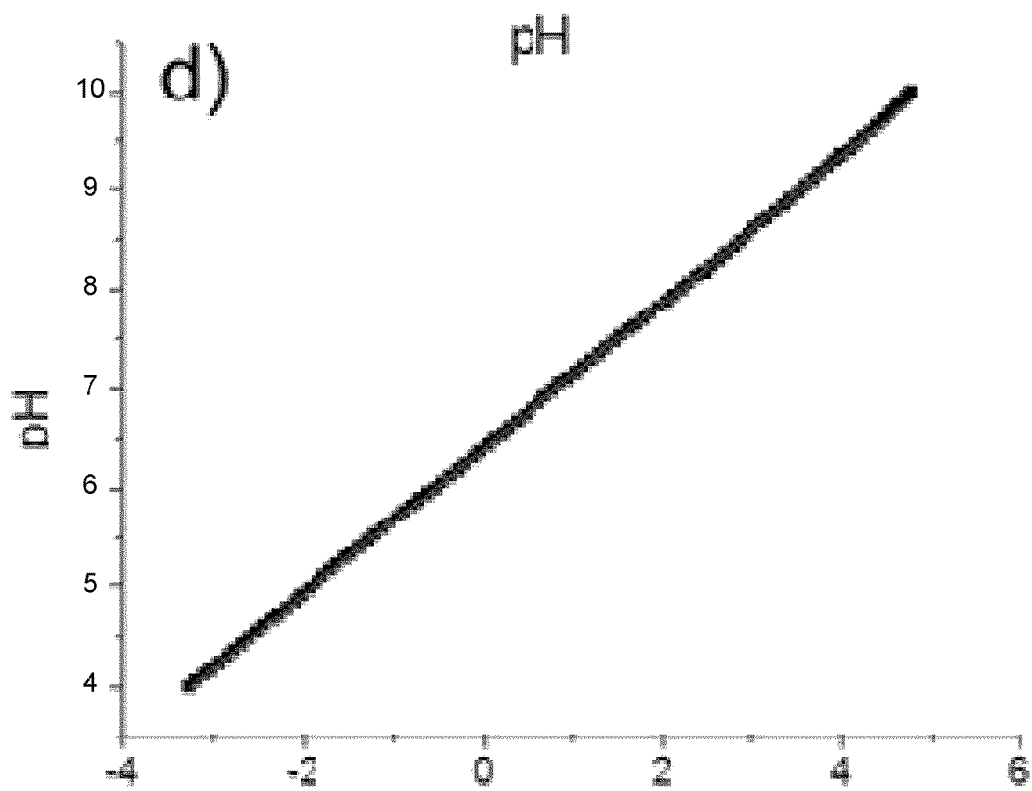

For the calculation of the pKa values, the fluorescence intensities $I_g$ (580 nm) and $I_r$ (640 nm) were measured using Image-J program by drawing the region of interest (ROI) on the obtained image for each pH value (FIG. 8a). The ratio (R) of the intensities $I_g/I_r$ was then calculated and plotted against the respective pH values (FIG. 8b), and the R curve was then fitted using the Boltzmann function (FIG. 8c). FIG. 8d shows the graph of −log( . . . ) term versus pH, the ratio R was obtained from the Boltzmann fit in (c) and $I_{a(\lambda 2)}$ and $I_{b(\lambda 2)}$ are fluorescence intensities at 640 nm (red channel) obtained from image in (a) at pH 4.5 and pH 8.5 using image-J program, $I_{a(\lambda 2)}$=41.92 and $I_{b(\lambda 2)}$=63.11. The intercept of linear fit of data points in (d) is pKa according to Eq. 2. The obtained pKa of SNARF was 6.39.

In the following equation (Eq. 1):

$$pH = pK_a - \log\left(\frac{R - R_b}{R_a - R} \times \frac{I_{b(\lambda_2)}}{I_{a\lambda_{(2)}}}\right)$$

R is the measured ratio of fluorescence intensities at each pH value, $R_a$ is the value of the R curve at acidic pH which is considered as the acidic titration endpoint, and $R_b$ is the value of the R curve at alkaline pH which is considered as the basic titration endpoint. The parameter $pH_{infl}$ is the point of inflection of the R curve, i.e. the pH value at which the slope of the curve is maximum, $\Delta pH$ is an indicator for the slope at the point of inflection. From the fitting of the R curve the fit parameters $R_a$, $R_b$, $pH_{infl}$ and $\Delta pH$ were determined.

In the next step pKa value of SNARF was calculated using the following equation (Eq. 2), $$pH = pK_a - \log\left(\frac{R - R_b}{R_a - R} \times \frac{I_{b(\lambda_2)}}{I_{a\lambda_{(2)}}}\right) \quad \text{Eq. 2}$$

The −log( . . . ) term in equation 2 was calculated for all pH values from pH4-10, the value R in −log( . . . ) term correspond to each point in Boltzmann fitting curve, whereas parameter $R_a$ and $R_b$ were obtained from fitting of equation 1. The two other parameters $I_{a(\lambda 2)}$ and $I_{b(\lambda 2)}$ in −log( . . . ) term correspond to the fluorescence intensities of SNARF obtained from images using image-J program at 640 nm (red channel) at acidic and alkaline region respectively for the fitted R curve (in the present study we took intensities at pH4.5 and pH 8.5). At the end, graph was plotted for −log ( . . . ) versus pH that would give a straight line (see Eq. 1) and intercept of linear fit is pKa. The calculated pKa value was 6.39.

Effect of A-MD NPs on Tumor pH

Figure 9B:
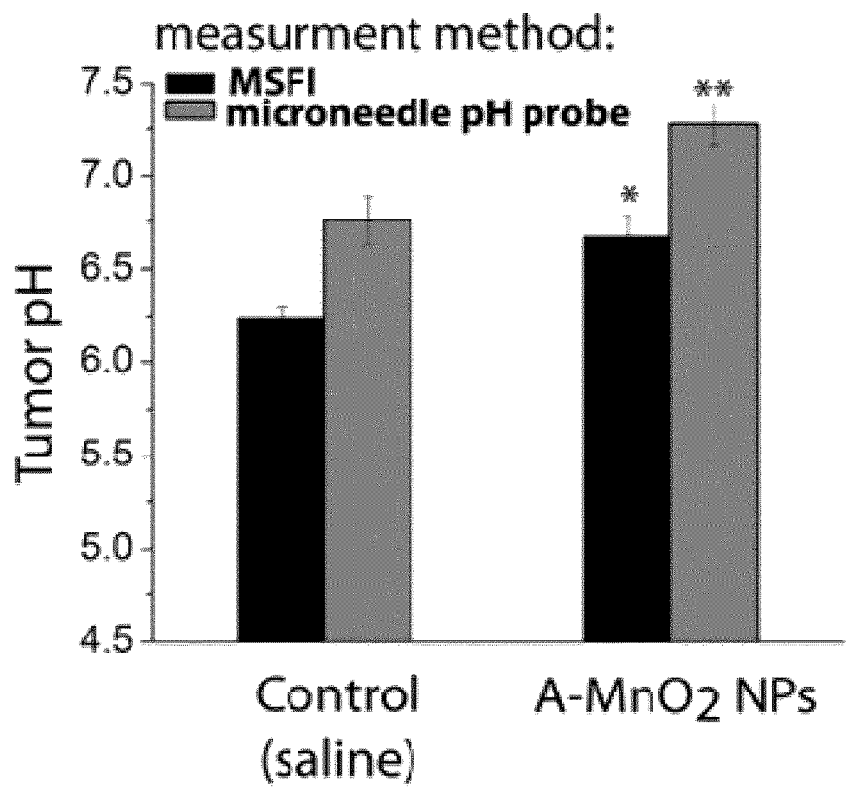
FIGS. 9a-b show the effect of A-MD NPs on tumor pH: (a) Ex vivo pH imaging of solid tumors treated with i.t. injection of A-MD NPs or saline (control). The tumors were cut in the central line and intratumoral pH was determined with multispectral fluorescence imaging (MSFI) using a pH-sensitive fluorescent dye (SNARF-4F) and the calibration curve. The bottom insert shows the pH scale obtained using the dye in biological phantoms of various pH values. (b) Tumor pH after treatment with A-MD NPs or saline (control) (n=3) determined ex vivo by MSFI (black bars) or with a microneedle pH probe (gray bars). Error bars represent standard errors of the mean. *statistically significant increase (*p=0.004, **p=0.007) in pH as compared to saline (control) treated group.
Figure 9A:
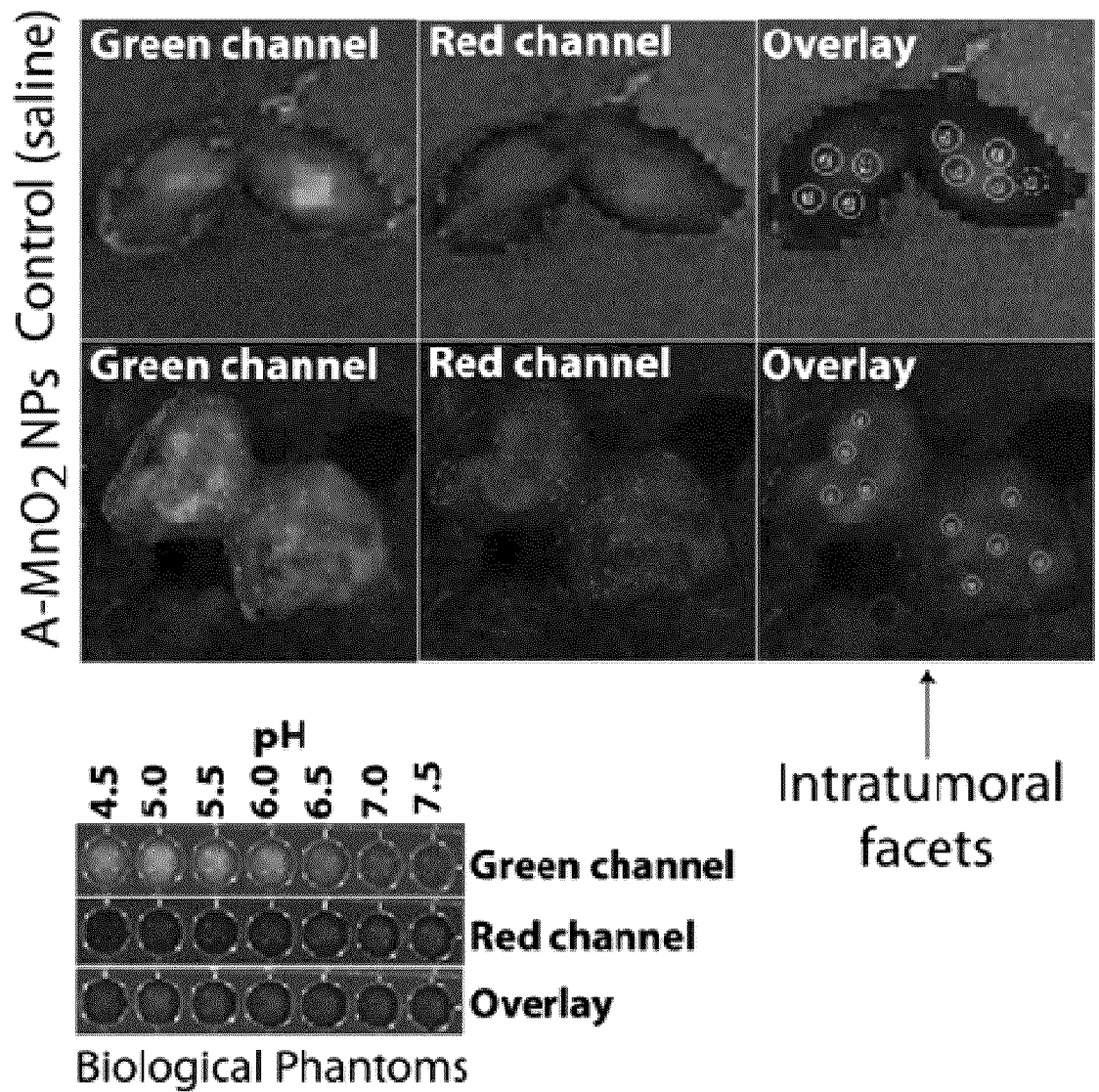

To measure intratumoral pH, the inventors employed complementary fluorescence imaging[43] and microneedle[44] methods. The inventors applied an established ex vivo tissue protocol for mapping tumor tissue pH which utilizes multispectral fluorescence imaging (MSFI) in conjunction with a pH-sensitive fluorescent dye (SNARF-4F) injected in vivo prior to animal sacrifice.[43] In this study, EMT6 tumor bearing animals were first injected i.t. with A-MDNPs, followed by intravenous injection of the SNARF-4F dye to stain for tumor pH. MSFI images of the intratumoral facets of dye-perfused tumors were then acquired ex vivo in tissue sections and correlated to local pH from the calibration curves obtained earlier with biological tissue-like phantoms. The tumor pH was also accessed ex vivo with a pH microneedle probe[43] immediately after the MSFI procedure. The inventors found that intratumoral injection of A-MDin orthotopic solid tumors led to higher intratumoral pH (FIG. 9). After a single i.t. injection of A-MDNPs, the tumor pH increased, after only 20 min, from 6.2 to 6.7 (as determined by MSFI) and from 6.7 to 7.3 (as determined by microneedle probe) (FIG. 9). The difference in pH values obtained with the two different methods can be attributed to interferences such as tissue autofluorescence and/or dye bleaching for MSFI images. Nonetheless, both methods revealed tumor pH values consistent with pH ranges reported in literature (e.g. pH 6.3-6.9, depending on the tumor model, cell line and measurement method).[45] The ex vivo tumor tissue pH measurements (FIG. 9b) revealed that A-MDNPs can quickly decrease tumor acidosis (i.e., within 30 min), most probably by quenching excessive protons produced by cancer cell glycolysis.

Figure 10:
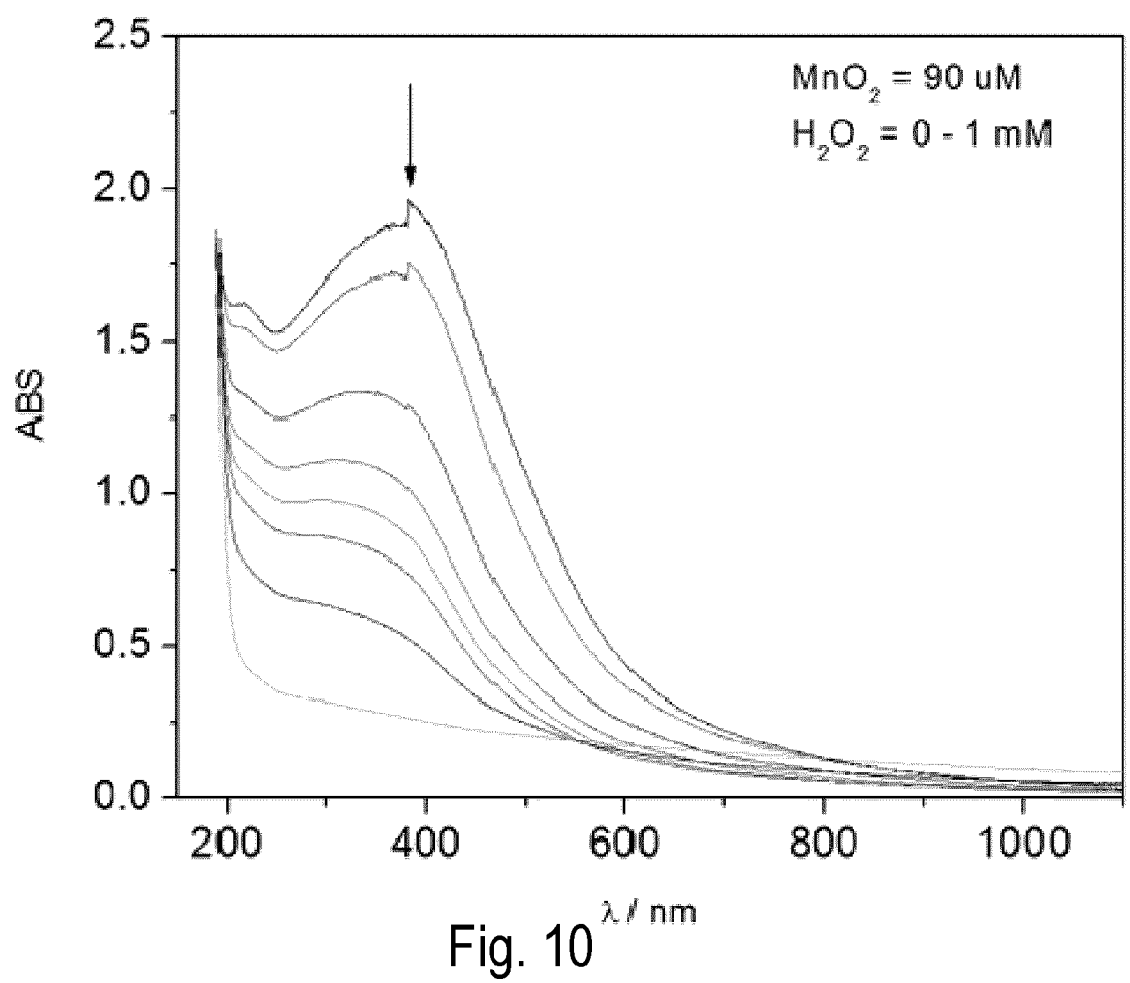
FIG. 10 shows consumption of A-MnO$_2$ nanoparticles by H$_2$O$_2$. Upon reaction with hydrogen peroxide for the production of molecular oxygen, MnO$_2$ nanoparticles are consumed. Consumption of the MnO$_2$ NPs (90 μM) by various endogenous concentrations of H$_2$O$_2$ (up to 1 mM) is shown. For the experiment, H$_2$O$_2$ was added to A-MnO$_2$ (A-MD) in saline, incubated for 5 min at room temperature and the absorbance of the MnO$_2$ was measured at 360 nm.
Figure 11A:
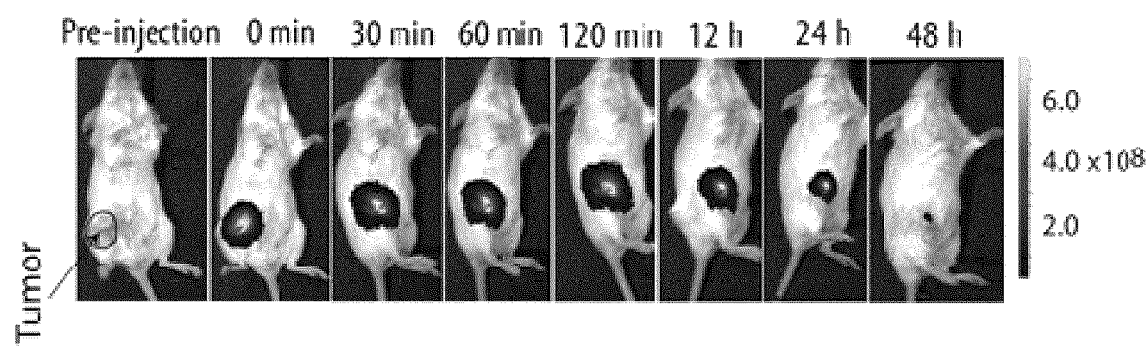
FIGS. 11a-e show the tumor retention of A-MD NPs and effect on tumor hypoxia, HIF-1α and VEGF. (a) Representative optical images of EMT6 tumor-bearing mouse with i.t. injected near infrared-labeled A-MD NPs at various times. (b) Representative immunohistochemistry in continuous sections from EMT6 tumors treated i.t. with saline (control) or A-MD NPs for 30 min, 60 min and 24 h. Tumor hypoxia was determined by pimonidazole binding HIF-1α and VEGF antibody. Scale bars correspond to 85 μm. (c-e) Quantification of tumor hypoxia, HIF-1 and VEGF after treatments, determined from classified images (not shown). (n=3). Error bars represent standard errors of the mean. *=statistically significant difference (*p=6.9E-5, p=0.003, *p=4.5E-4) as compared to saline (control) treated group.

Prolonged Regulation of Tumor Hypoxia, HIF-1α and VEGF is Related to Extended Tumor Retention of A-MD NPs The inventors injected near-infrared dye-labelled NPs into orthotopic EMT6 breast tumors. The A-MD NPs are expected to be cleared as MD NPs can be completely consumed by $H_2O_2$ (FIG. 10) and thereafter the remaining BSA/PAH complex is expected to undergo enzymatic degradation by specific proteases, via an already established mechanism for the fate of polyelectrolyte complexes taken by cells.[46, 47] In vivo fluorescence imaging data (FIG. 11a) showed substantial diffusion of NPs within the tumor tissue almost immediately after the injection and prolonged retention of NPs within the tumors for at least 24 h, followed by gradual clearance from the tumors over 24-48 h.

Figure 11B:
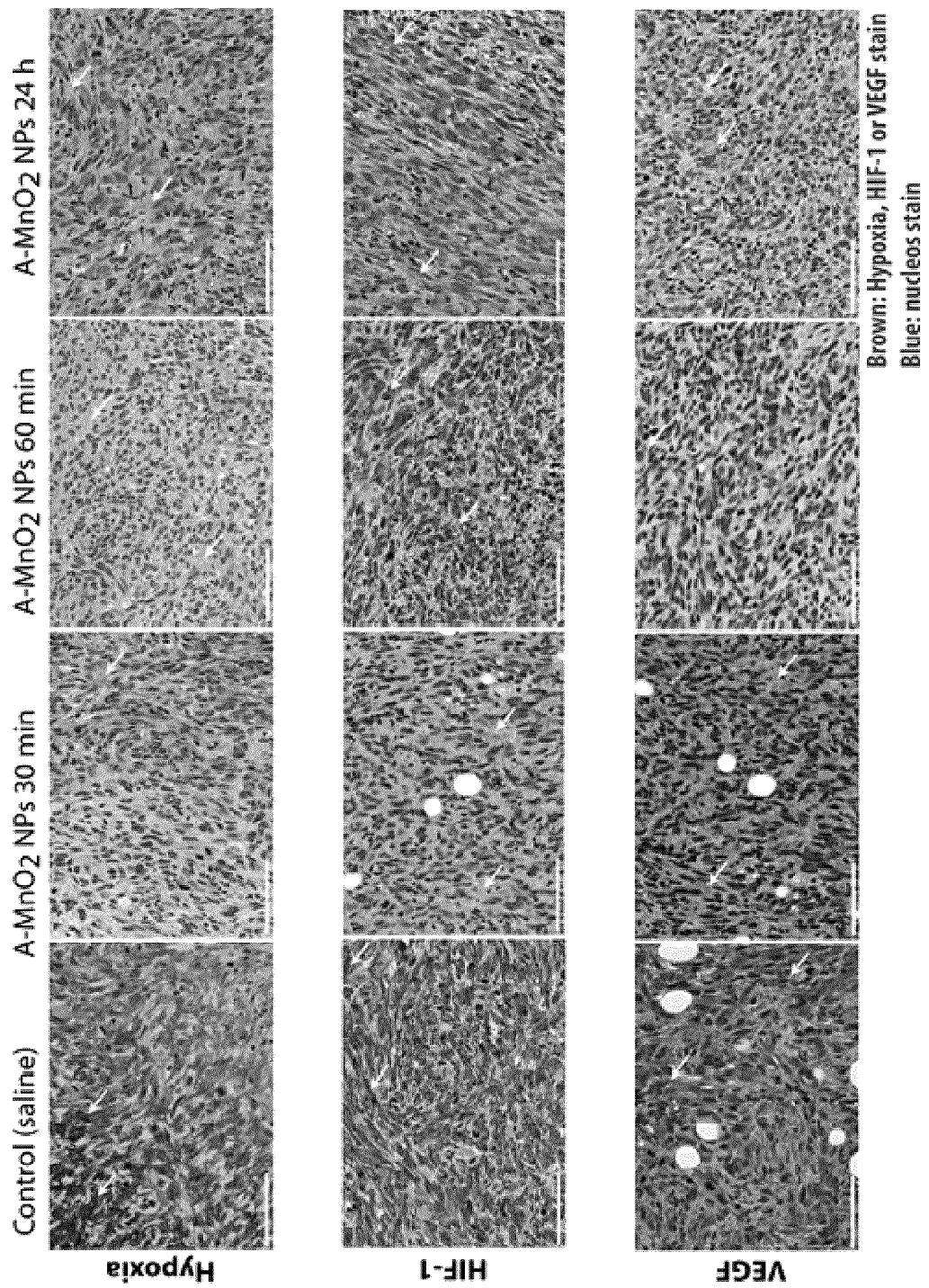
Figure 11E:
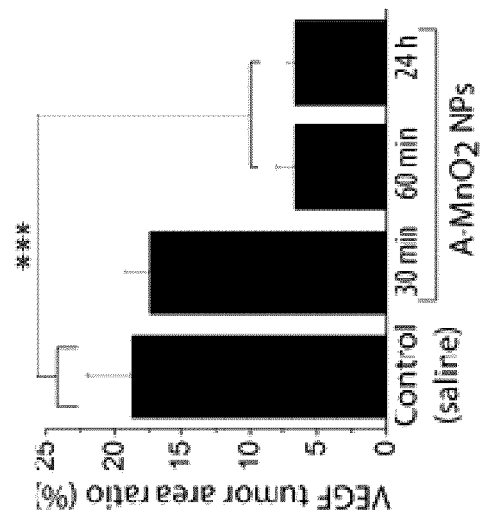
Figure 11D:
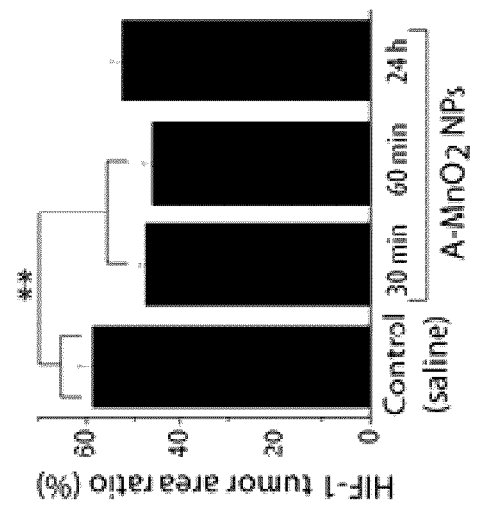
Figure 11C:
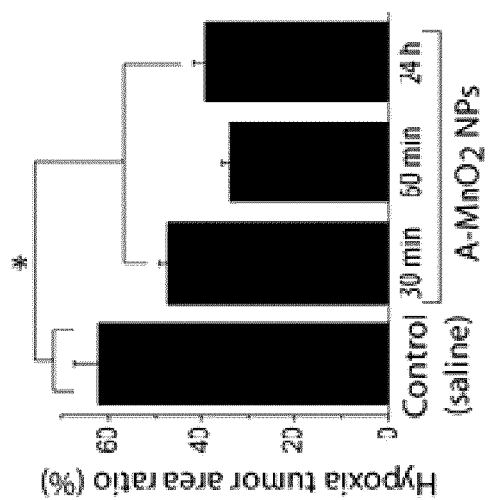

The inventors then investigated the effect of A-MD NPs on tumor hypoxia in vivo within the 24 h period post NP-injection by immunohistochemistry to directly measure tissue hypoxia using a pimonidazole marker[48] and the expression of HIF-1α and VEGF (FIG. 11b) using antibodies on ex vivo tissues. Unlike the in vivo PA experiments that measure hemoglobin-related vascular $sO_2$, immunohistochemistry of ex vivo tissues from animals injected with pimonidazole prior to sacrifice directly detects the presence of hypoxic tumor cells. The inventors found that tumors treated with A-MD NPs for 30 min, 60 min or 24 h showed 24, 45 and 37% less tissue hypoxia, respectively, as compared with the saline control (FIG. 11c), suggesting a time-dependent and sustained effect of NPs on tumor hypoxia. The same tumors also showed a 19, 21 and 10% decrease in the expression of HIF-1α (FIG. 11d), and 7, 65 and 65% decrease in the expression of VEGF (FIG. 11e), after 30 min, 60 min and 24 h treatment with A-$MnO_2$ NPs, respectively. HIF-1α is a master regulator of the transcriptional response to acute and chronic hypoxia,[48, 49] while VEGF is involved in cancer cell metabolism, angiogenesis, invasion, metastasis and apoptosis.[50] Over-expression of VEGF is a hallmark of tumor angiogenesis.[50] Based on the impact of angiogenesis on cancer progression and treatment, several anti-angiogenic agents including anti-VEGF molecules are now in clinical trials as a sole treatment or in combination with conventional cancer chemotherapy.[49] Thus downregulation of HIF-1α and VEGF expression would be expected to improve tumor prognosis. The results presented above show that the effectiveness of A-MD NPs on the regulation of the TME is not limited to the transient increase of tumor oxygenation and pH; they also have an effect on the down-regulation of hypoxia-responsive protein expression that plays an important role in biological behavior and therapeutic response of many types of cancers. 7' 8 Because the expression of HIF-1α is transient depending on the relative rate of synthesis (via an $O_2$-independent pathway) and degradation (via an $O_2$-dependent pathway),[51] the sustained in situ production of $O_2$ by A-MD NPs is beneficial to prolonged regulation of TME especially impacting on the expression of downstream proteins, such as VEGF-4.

Figure 11F:
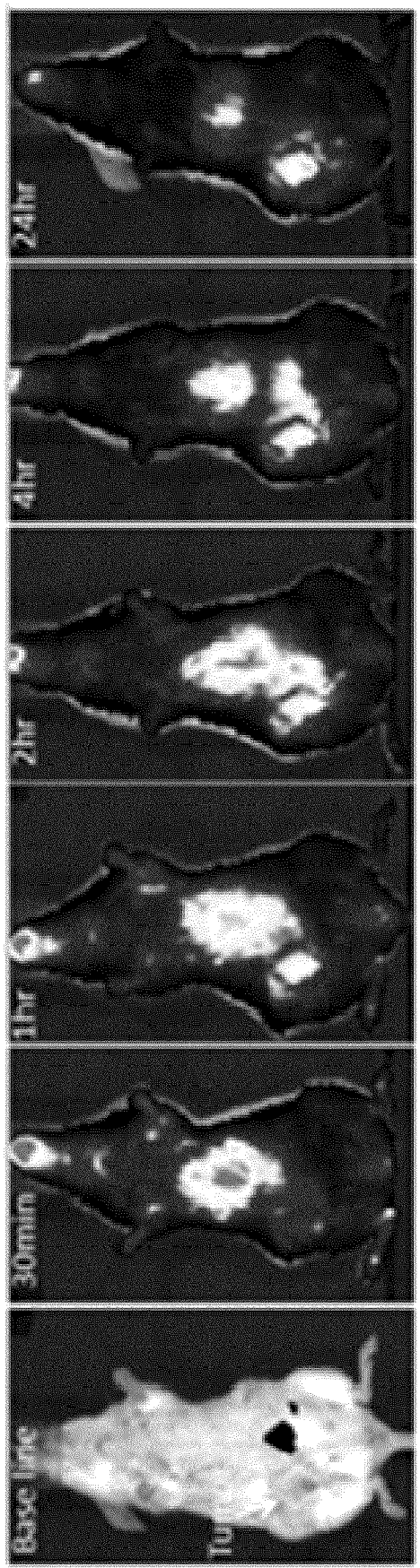
FIGS. 11f-g show in vivo biodistribution, tumor accumulation and tumor retention of NIR fluorophore-labelled formulations (f) L-MD NPs and (g) PMA-MD NPs injected i.v. in Balb/c mice bearing orthotopically implanted EMT6 murine breast tumor cells. Fluorescence was determined prior to intravenous injection (base line), and at different time points post-injection up to 24 hours. Tumor is indicated with the arrow. Bottom rows showing ex vivo fluorescence images of different organs: liver, tumor, lungs, heart, kidneys, spleen, intestine and blood. Tissues were excised from the tumor-bearing mice at 4 and 24 hours post-NP injection.
Figure 11F:
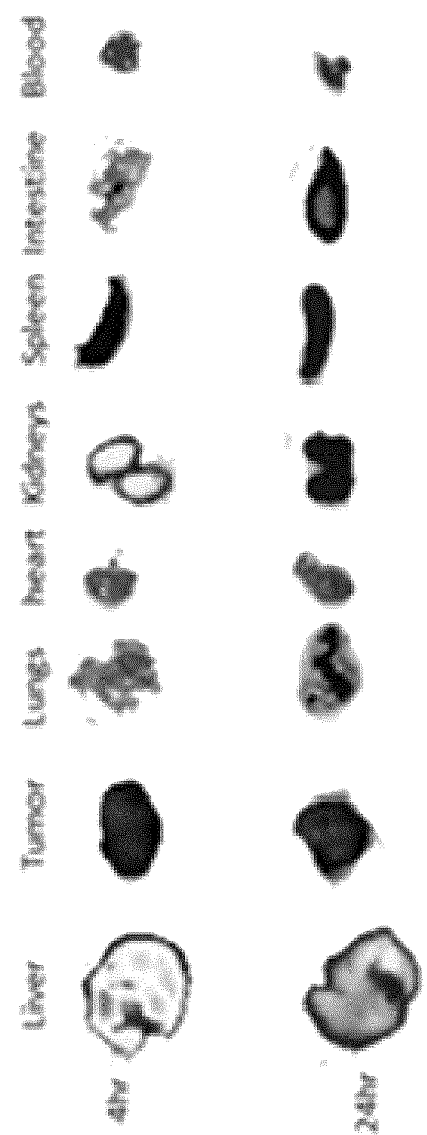
Figure 11G:
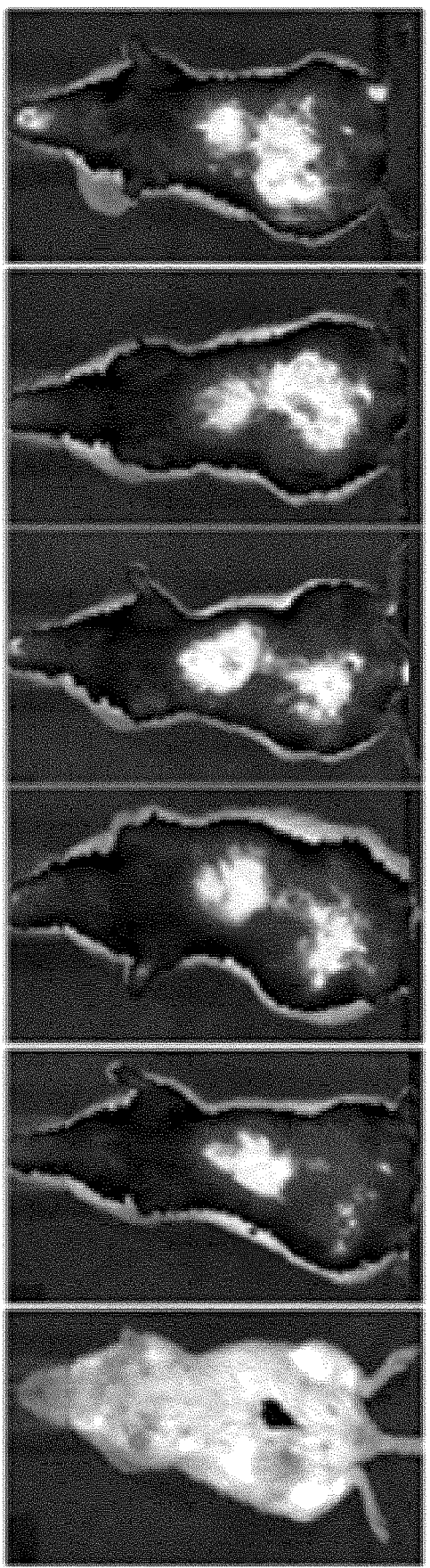
Figure 11G:
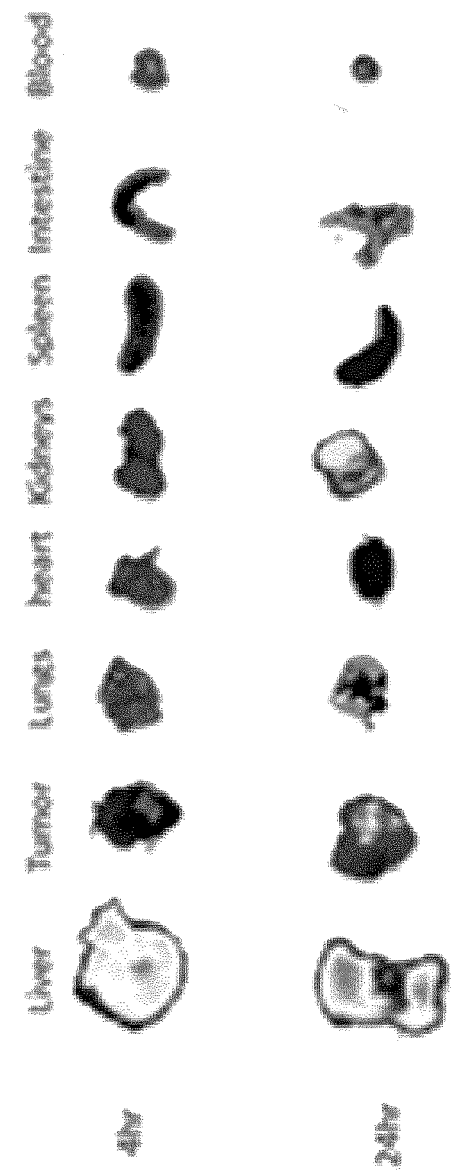

The biodistribution and ex vivo images of the resected organs (FIGS. 11f-g, where lighter shade indicates higher fluorescence emission) showed that NPs (lipid and polymer-based) reached and accumulated in the tumor site within 1 h post i.v. injection and remained in the tumor during 24 h duration of the experiment.

A-MD NPs Enhanced Anti-Tumor Effect of Radiation

Various studies have shown that hypoxic cells in solid tumors are two-to-three times more resistant to a single dose of ionizing radiation than those with normal levels of oxygen.[3, 4] To explore whether in situ oxygen production by A-MD NPs can enhance RT, the inventors conducted preliminary studies in an in vivo orthotopic murine breast tumor model. EMT6 tumors were treated with A-MD NPs or saline 30 min prior to irradiation. A significant tumor growth delay was observed in mice treated with the combination of A-MD NPs and RT (FIG. 12a) compared to the control groups. The average tumor volume in the A-MD NPs+RT group at day 5 remained at ≈78 mm³ while the RT alone group (treated with saline+RT) reached an average tumor volume of ≈231 mm³ at the end of day 5 after treatment. Tumor weight was also significantly lower in the A-MD NPs+RT group (FIG. 12b). Interestingly, a decreased tumor growth was observed in the A-MD NP alone treated group compared to the saline group (non-irradiated controls) (FIG. 12a). This moderate antitumor effect may be attributable to the manipulation of the TME by the A-MD NP formulation which reduces VEGF levels by 65%. A more in-depth study will be conducted in the future to further investigate this observation.

Figure 12F:
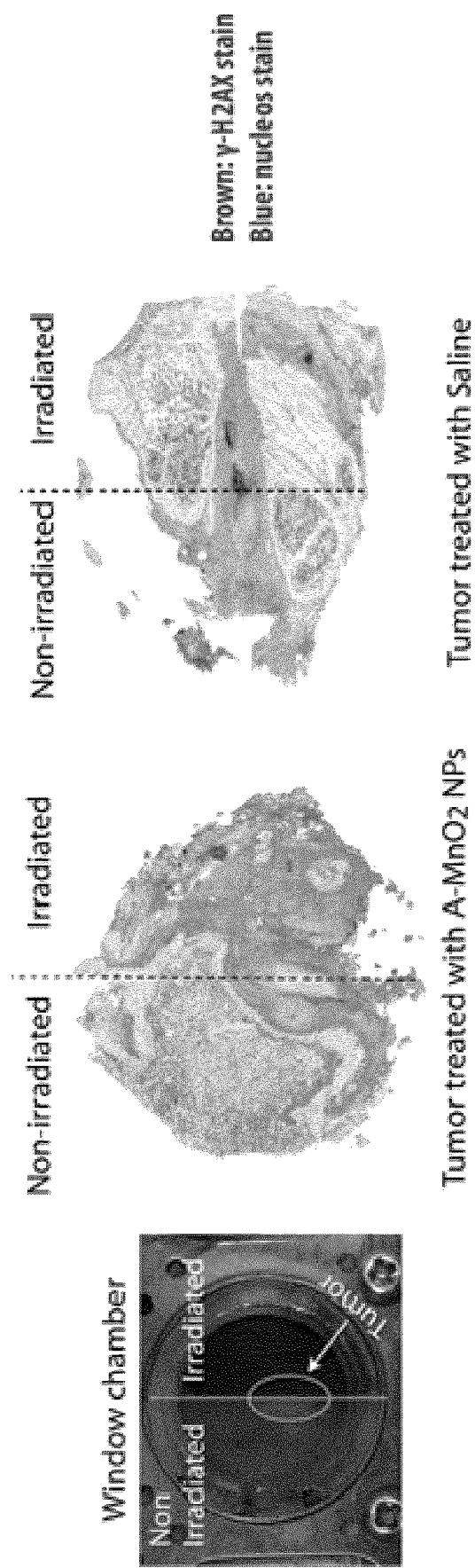

To confirm that the effect of A-MD NP on the enhancement of radiation response was due to tumor cell cytotoxicity, the percentage of tumor apoptotic and necrotic areas was determined. Tumors treated with A-MD NP+RT showed a significantly higher tumor cell death (71%) compared to the saline+RT treated group (40%) (FIG. 12c). The inventors further evaluated radiation-induced DNA double strand breaks (DNA DSBs) in tumor tissues by using gamma H2AX staining to stain for DNA DSBs. The DNA DSB is considered the most lethal type of damage induced by ionizing radiation and is a major indicator of the efficacy of treatment.[52] Combined treatment with A-MD NPs and irradiation resulted in increased DNA damage (71%) compared to the saline control with irradiation (28%) in the EMT6 solid tumor (FIG. 12d). A window chamber mouse model bearing tumor[44] was employed to determine the induction of DNA DSB after treatment with radiation combined with A-MD NPs or saline (FIGS. 12e-f). Spatially localized focal x-ray irradiation was performed on half of the tissue in the transparent window chamber allowing the inventors to determine the relative effect of treatment in the same mouse. Increased DNA DSBs were observed when the tumor was treated with both A-MD NP and RT versus radiation alone. Oxygen close to DNA is known to react with radiation produced radicals in DNA "fixing" them in a state that is difficult for the intrinsic cellular DNA repair mechanisms to deal with.6 Therefore, it is likely that oxygen generated by reaction of A-MD NP with $H_2O_2$ in tumor tissue facilitated the oxygenation effect causing more tumor cell death upon radiation thereby leading to an enhanced delay in tumor growth.

The inventors have demonstrated a completely new and innovative application of A-MD NPs for the modulation of the TME. The intratumoral treatment of murine breast tumors with A-MD NPs resulted in simultaneous attenuation of hypoxia and acidosis in solid tumors in vivo. Moreover, for the first time a bioinorganic nanoparticle system has been demonstrated to promote down-regulation of crucial tumor progression-related factors, i.e., HIF-1α and VEGF. In addition the inventors have demonstrated the application of A-MD NPs for enhancement of radiation induced tumor growth delay and cancer cell death. This work suggests a potential of the A-MD NP system to regulate multiple biological attributes of the TME simultaneously and to improve cancer response to radiation treatment. The in vivo results obtained in the present work encourage continuing efforts for the optimization and application of MD NPs in combination with other cancer treatments such as chemotherapy and photodynamic therapy (PDT).

Methods

Nanoparticle Synthesis:

MD NPs were prepared by directly mixing the aqueous solutions of $KMnO_4$ and poly(allylamine hydrochloride) (PAH, 15 kDa). Briefly, 18 mL of $KMnO_4$ solution (3.5 mg mL⁻¹) was mixed with 2 mL of PAH solution (37.4 mg mL⁻¹), the mixture was left for 15 min at room temperature until all permanganate was converted to $MnO_2$. NP formation was confirmed by recording UV-Vis absorption spectrum. NPs were washed three times with doubly distilled (DDI) water using ultracentrifugation (50 k rpm for 1 hr). This step led to small (~15 nm) MD NPs stabilized with PAH. At the final step, BSA was added to the MD NP solution at a BSA/NP ratio 2.5% (wt/wt), and NaCl was added to make the solution normal saline (0.9% NaCl). This step led to the formation of A-MD NPs (~50 nm), with several MD NPs entrapped in a PHA/BSA complex due to strong electrostatic interaction between the protein and the polymer. A typical preparation led to a ≈0.7% A-MD NPs solution, corresponding to ≈1.1 mM MD as determined by inductively coupled plasma (ICP) analysis. A-MD NPs were further diluted with cell medium or sterile saline for in vitro and in vivo studies, respectively. Protein labelling kits AnaTag™ HiLyte Fluor™ 594 (Texas Red) and AnaTag™ 750 (AnaspecInc, USA) were used to label albumin for the preparation of red fluorescent and near-infrared NPs, respectively.

Cell Lines, Tumor Models and Treatments:

In vitro: A murine EMT6 breast cancer cell line was utilized and cultured following standard cell culture procedures.[45] For all in vitro experiments, cells in αMEM medium (10⁵ cells per mL) were treated with A-MDNPs for 1 h. Cell viability was measured using a standard MTT colorimetric assay protocol.[45] In vivo: All procedures strictly complied with the ethical and legal requirements under Ontario's Animals for Research Act and the Federal Canadian Council on Animal Care guidelines for the care and use of laboratory animals and were approved by the University Animal Care Committee of the University of Toronto. Solid tumors of EMT6 breast cancer cells (10⁶) were grown orthotopically in Balb/c mice and animals were randomly allocated for all treatments (n=3/group). For in vivo experiments, tumors were injected with 50 μL of A-MD NPs solution in saline (0.2 mM MD), which made the MD concentration ≈45 μM in a ≈200 mm³ tumor. Controls were injected with equivalent volume of sterile saline.

Quenching of $H_2O_2$ by Nanoparticles:

For the quenching experiments, A-MD NPs (90 μM) in cell medium containing 10% FBS at 37° C. and $H_2O_2$ (1 mM) was added to initiate the reaction. The residual concentration of $H_2O_2$ was determined over time using a PeroXOquant assay kit (Pierce, USA), at 37° C. Cell medium with 10% FBS was used as a vehicle control.

In Vitro Oxygen and pH Measurements:

$O_2$ generated by A-MD NPs and pH changes were measured in a semi-sealed chamber coupled with a MI-730 micro-oxygen electrode and a MI-407 pH+MI 402 reference microelectrodes (Microelectrodes Inc, USA), at 37° C. A-MD NPs were dispersed in αMEM cell medium containing 10% FBS to give various MD concentrations (10-90 μM). The system was made hypoxic by bubbling with 2 $N_2$. Endogenous level of $H_2O_2$ (250 μM) was injected into the chamber to initiate $O_2$ generation. For experiments with hypoxic cells: Murine breast cancer EMT6 cells (10⁵ cells per mL) were suspended and stirred in αMEM medium in glass vials plugged with rubber stoppers and pierced with two hypodermic needles for gassing. The cell suspension was made hypoxic by introducing a mixture of 95% $N_2$ and 5% $CO_2$ for 20 min at 37° C. A-MD NPs (45 μM) were then injected and the oxygen levels monitored over time. For all experiments: pH or $O_2$ were monitored every 60 s using an Oakton pH 1100 (Termo Fisher Scientific Inc, USA) coupled with $O_2$-ADPT Oxygen Adapter (Microelectrodes Inc, USA) for $O_2$ measurements. All electrodes were calibrated according to manufacturer's instructions. αMEM medium with 10% FBS, with or without cells was used as control.

Cellular Uptake of NPs:

Murine EMT6 breast tumor cells ($10^5$ cells) were incubated for 1 h with A-MD NPs (45 μM) at 37° C. before microscopic analysis. Cell uptake of NPs by transmission electron microscopy (TEM) was performed using a H7000 TEM microscope (Hitachi, Japan), following standard methods for sample preparation.[45] An EVOS fluorescence microscope (AMG, USA) was used to image live cells following incubation with red fluorescent dye labelled A-MD NPs. Cell nuclei were stained blue with HOESCHT 33342 (Invitrogen Molecular Probes, USA).

Tumor Retention of NPs:

A Xenogen IVIS Spectrum Imaging System (Caliper Life Sciences Inc., USA) was used to image tumor bearing animals over time following i.t. treatment with near-infrared labelled A-MD NPs. At each time point, a bright field image was acquired and fluorescence-labelled A-MD NPs were imaged at 754 nm excitation and 778 nm emission. Image fluorescence was quantified by equalizing the fluorescence intensity range across all images.

Tumor pH Measurements:

A pH-sensitive fluorophore SNARF-4F (Life technologies S23920, NY USA) was used for ex vivo tumor pH imaging following an established protocol.[34] Tumor bearing mice were injected i.t. with NPs in saline followed by i.v. injection of the dye (1 nmol of SNARF-4F in 200 μL of sterile saline). Animals were sacrificed 20 min following injections, tumor tissue was immediately harvested, cut in half and imaged with Xenogen IVIS Spectrum (Caliper Life Sciences Inc., USA). For control experiment sterile saline was injected i.t. followed by intravenous (i.v.) injection of SNARF, tumors were imaged ex vivo using the same conditions. All the necessary calibration curves of dye were performed following published protocols[55, 56] and biological tissue-like phantoms were prepared following standard procedures[43]. Tumor pH was also measured using a MI-407 pH+MI 402 reference microelectrodes following a standard protocol[45] (Microelectrodes Inc, USA).

Tumor Oxygenation Measurements:

A Vevo LAZR Photoacoustic Imaging System (VisualSonics Inc., Canada) with a 21 MHz centre frequency transducer (LZ-550, VisualSonics Inc., Canada) was used to measure vascular oxygen saturation ($sO_2$) in situ over time before and after i.t. treatment with A-MD NPs. Ultrasound was utilized to guide NP injection in order to administer treatments to the tumor. Animals were maintained below 7% oxygen atmosphere during the experiment and $sO_2$ measurements were assessed using standard multispectral photoacoustic imaging in the tumors in vivo using two excitation wavelengths (750 nm and 850 nm) for deoxygenated and oxygenated hemoglobin, respectively.

Immunohistochemistry Detection of Tumor Hypoxia:

The hypoxia marker pimonidazole hydrochloride (Hypoxyprobe™-1 plus kit, Hypoxyprobe Inc, USA) was used for ex vivo tissue staining of hypoxia following the protocol provided with the kit. Rabbit polyclonal HIF-1α antibody (dilution 1:100, Novus Biologicals, Catalog number: NB100-134) and Rabbit anti-VEGF (dilution 1:100, Thermo Scientific, Catalog number: ab-222-P) were used for the staining of HIF-1α and VEGF, respectively. Briefly, tumor-bearing mice (n=3/group) were treated i.t. with A-MD NPs or saline (control). After pre-determined times animals were sacrificed and tumor tissues were harvested and fixed with 10% neutral buffered formalin solution (Sigma Aldrich, USA) for histological analysis. Tumor tissue preparation and analysis were performed by the CMHD Pathology Core laboratory at Mount Sinai Hospital, Toronto. Slides were scanned with a NanoZoomer 2.0 RS whole slide scanner (Hamamatsu, Japan) and images were analysed with Visiopharm 4.4.4.0 software.

In Vivo Ionizing Radiation Treatment:

Solid tumor of EMT6 murine breast cancer cells were grown orthotopically in Balb/c mice. Mice were divided into 4 groups (n=3/group): 1) Saline, 2) Saline+RT, 3) A-MD NP, 4) A-MD NP+RT. Treatments were initiated when the tumors reached an approximate volume of 100 mm$^3$. The mice were restrained in a specially designed acrylic box, and the tumors were irradiated locally with 10 Gy, 30 min after i.t administration of saline and A-MD NP. The tumor size was measured as a function of time with vernier calipers in two dimensions and tumor volumes were calculated by the formula $V=[(\text{length})\times(\text{width})^2]/2$. At the end of experiment, the animals were sacrificed and the tumor masses were excised and weighed. Tumor tissue was also formalin fixed and stained with terminal deoxynucleotidyltransferased UTP nick end labelling (TUNEL) and haematoxylin and eosin (H&E) to determine percent apoptosis and necrosis.

In another set of experiments, mice were sacrificed 24 hours after radiation treatment. Tumor tissue was excised, formalin fixed, sectioned and gamma H2AX measured to evaluate DNA DSBs. Slides were scanned with a NanoZoomer 2.0 RS whole slide scanner (Hamamatsu, Japan) and images were analysed with Visiopharm 4.4.4.0 software.

The enhancement of DNA DSBs due to the combination of RT+A-MD NP was also evaluated in a dorsal skin-fold window chamber (DSWC) EMT6 mouse model.[44] Treatments (Saline and A-MD NP) were injected i.t. and only half of the chamber was irradiated at 10 Gy. Irradiating only half of the chamber allowed the inventors to determine the effect of treatment alone in the same mice. 24 hours post irradiation tumor tissue was excised and stained with gamma H2AX staining to evaluate DNA DSBs. Slides were scanned and images were analysed with Visiopharm 4.4.4.0 software.

Statistical Analysis:

Data are presented as mean±standard error of the mean for results obtained from three independent trials unless otherwise indicated. Student's t-test or analysis of variance (ANOVA) followed by Tukey t-test (OriginPro8©) were utilized to determine statistical significance between two or more groups, respectively. p-values <0.05 were considered statistically significant.

Example 4: Preparation and Characterization Terpolymer Crosslinked Denatured Albumin-Complexed MD NPs with or without PEG (TER-MD)

Figure 13:
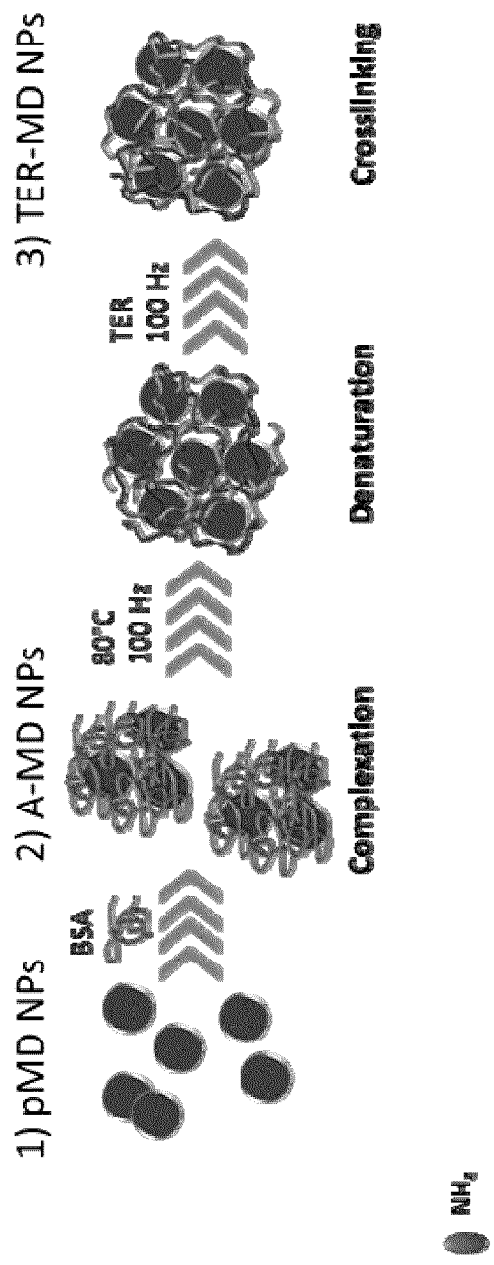
FIG. 13 is a schematic showing the steps for preparation of A-MD NPs, denatured A-MD NPs and terpolymer crosslinked denatured A-MD (TER-MD) NPs.
Figure 13:
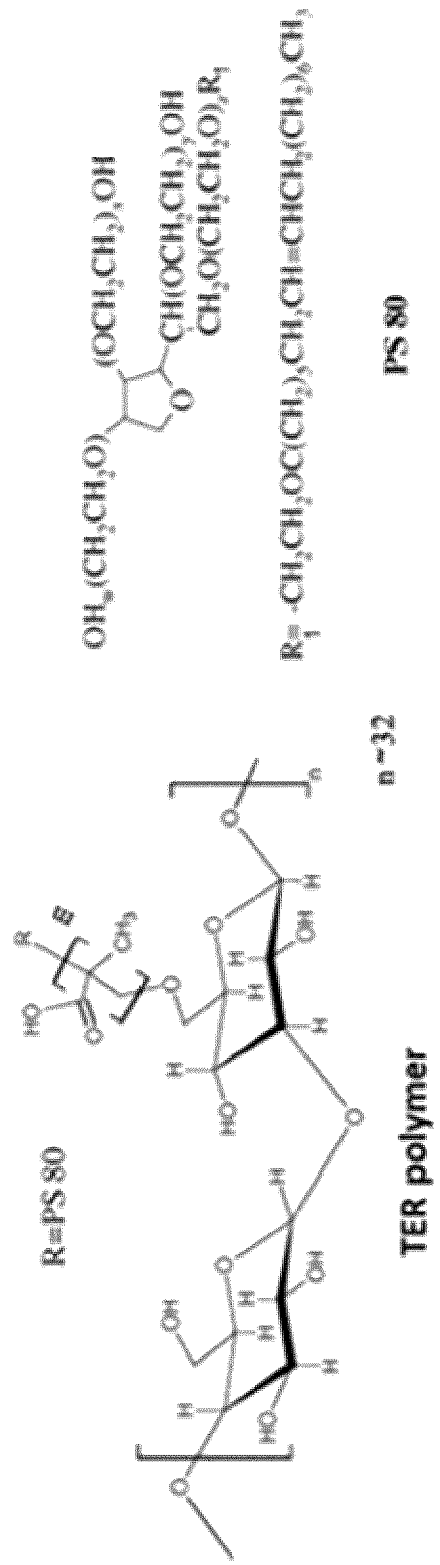

A-MD NPs were denatured and crosslinked with a terpolymer (TER) (poly(methacrylic acid)-polysorbate 80-g-starch), prepared as previously described[56]. BSA was denatured by heating and ultrasonication of A-MD NPs (80° C., 100 Hz), to which activated TER polymer was added to crosslink the protein matrix through covalent reaction of the carboxylic groups of the TER polymer with the amine groups of the protein. In brief, TER polymer (50 mg) was dissolved with 1 mL of DDI water and 15 mg of both N-(3-Dimethylaminopropyl)-N'-ethylcarbodiimide hydrochloride (EDC) and N-Hydroxysuccinimide (NHS) were added. The solution was stirred for 30 min at room temperature for activation of the carboxylic groups of the TER polymer. Meanwhile, in a 14 mL polypropylene tube (falcon tube) 10 mL of polyelectrolyte pMD NPs solution (10 mM) was mixed with 1.2 mL of BSA solution in normal saline (10 mg/mL) and 50 µL of Pluronic® F-68 solution (100 mM in DDI water). The solution in a falcon tube was transferred to a water bath at 80° C. and kept under stirring and sonicated for 60 sec by using an ultrasonic processor probe operating at 100 Hz (Heischer UP100H, Germany). The mixture was removed from the hot water, to which 500 µL of activated TER polymer solution was added and the dispersion was sonicated for another 5 min. To obtain TER-MD NPs with a PEG corona, a mixture of melted lipid-PEG (polyoxyethylene stearate) of two different chain lengths (e.g. 8 mg of 5 kDa and 4 mg of 2 kDa) was added prior to adding the crosslinker, i.e., activated terpolymer. The obtained brown dispersion was washed with DDI water using ultracentrifugation (14 k rpm for 20 min) for three times. The obtained pellets were then dispersed with 1 mL of normal saline solution by ultrasonication. About 85-90% of the pMD NPs was loaded in the TER crosslinked denatured BSA matrix, as determined by measuring remaining pMD in the supernatant after washing using UV-Vis spectrophotometry. A typical preparation resulted in a ≈7 mM TER-MD NP emulsion. The schematic summarizing the preparation of the TER-MD NPs is shown in FIG. 13. Obtained NPs were negatively charged (−35 mV) with average size around 150 nm (FIG. 14a). TEM pictures revealed particles with a popcorn-like shape, with several pMD-BSA complex nanoparticles entrapped in one TER-MD NP (FIG. 14b).

Example 5: Covalent Conjugation of Oleic Acid to the Surface of MD Nanoparticles (Transfer to Hydrophobic Phase oMD NPs)

Figure 15C:
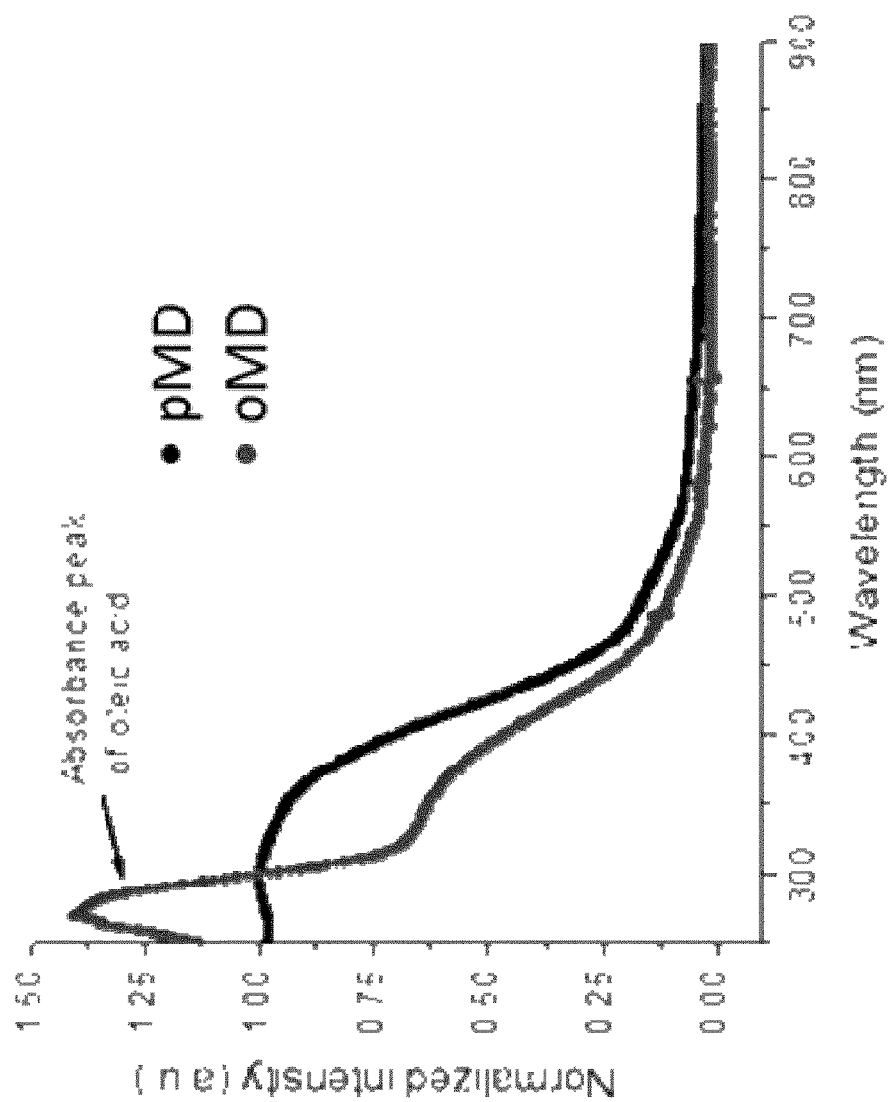
FIG. 15 shows phase transfer of pMD NPs from hydrophilic to hydrophobic phase through covalent conjugation of oleic acid on the surface of the NPs (oMD NPs) (left). (a) pMD NPs before phase transfer (in DDI water phase) and after phase transfer (in chloroform phase). (b) oMD NPs dispersion in DDI water (left) and in chloroform (right). Very stable particles were obtained after conjugation of oleic acid and no aggregation was observed. (c) UV-Vis spectrum of NPs before and after conjugation with oleic acid. The new sharp peak at around 280 nm corresponds to oleic acid conjugated to the NPs surface.
Figure 15A:
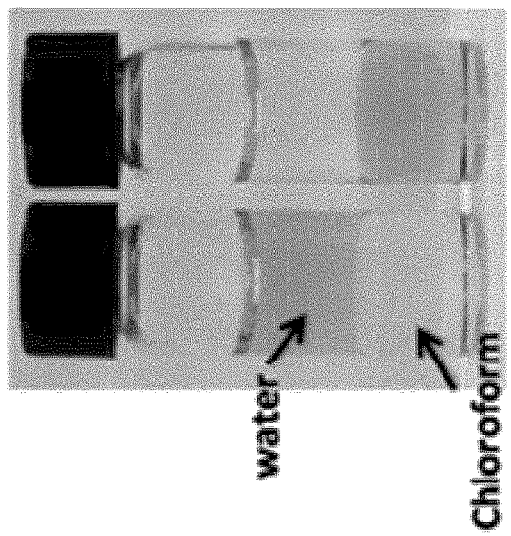
Figure 15B:
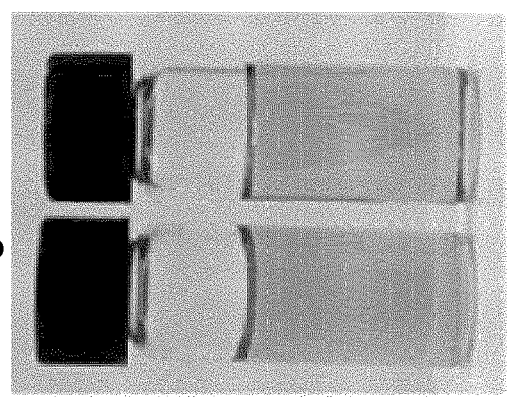

Hydrophilic, pMD NPs were transferred to a hydrophobic phase by covalently linking the hydrophobic molecule oleic acid to the surface of pMD NPs. For this purpose amine groups of poly(allylamine hydrochloride) (PAH) polyelectrolyte present on the surface of pMD NPs were covalently attached with carboxylic group of oleic acid using N,N'Dicyclohexylcarbodiimide (DCC) carbodiimide reagent chemistry for cross-linking. Briefly, 150 mg of oleic acid (0.5 mole) was dissolved in 5 mL of dimethylformamide (DMF) and in a separate vial 110 mg of DCC (0.5 mmole) was dissolved in 5 mL of DMF. Once DCC solution was cleared it was poured in oleic acid-DMF solution under stirring. The mixture was left under stirring for 15 minutes, after the required time, 500 µL of pMD NP aqueous solution (30 mM based on ICP analysis) was added slowly under vigorous stirring. After 5-10 minutes big aggregates were observed, at this stage 5 mL of chloroform was added and a clear dispersion of oMD NPs was obtained (FIG. 15a). The solution was left under stirring over night for complete reaction of oleic acid with pMDNPs. Next day, for oMD NPs separation, reaction solution was mixed with acetone in a volume ratio of 1:3 (reaction mixture: acetone), after addition of acetone big aggregates of oMD NPs were observed which were then separated by centrifugation at 4 k rpm. The precipitate was re-dissolved in chloroform and once again washed using the acetone to remove by products of reaction. Finally, precipitate was re-dissolved in chloroform and stored at 4° C. Oleic acid conjugate-pMDNPs (oMD) were stable and no aggregates were observed even after months (FIG. 15b). The obtained hydrophobic oMD NPs were characterized using the UV-absorbance spectrometer, an absorbance peak was observed with a sharp absorption maximum at 280 nm which corresponds to the oleic acid (FIG. 15c).

Figure 16:
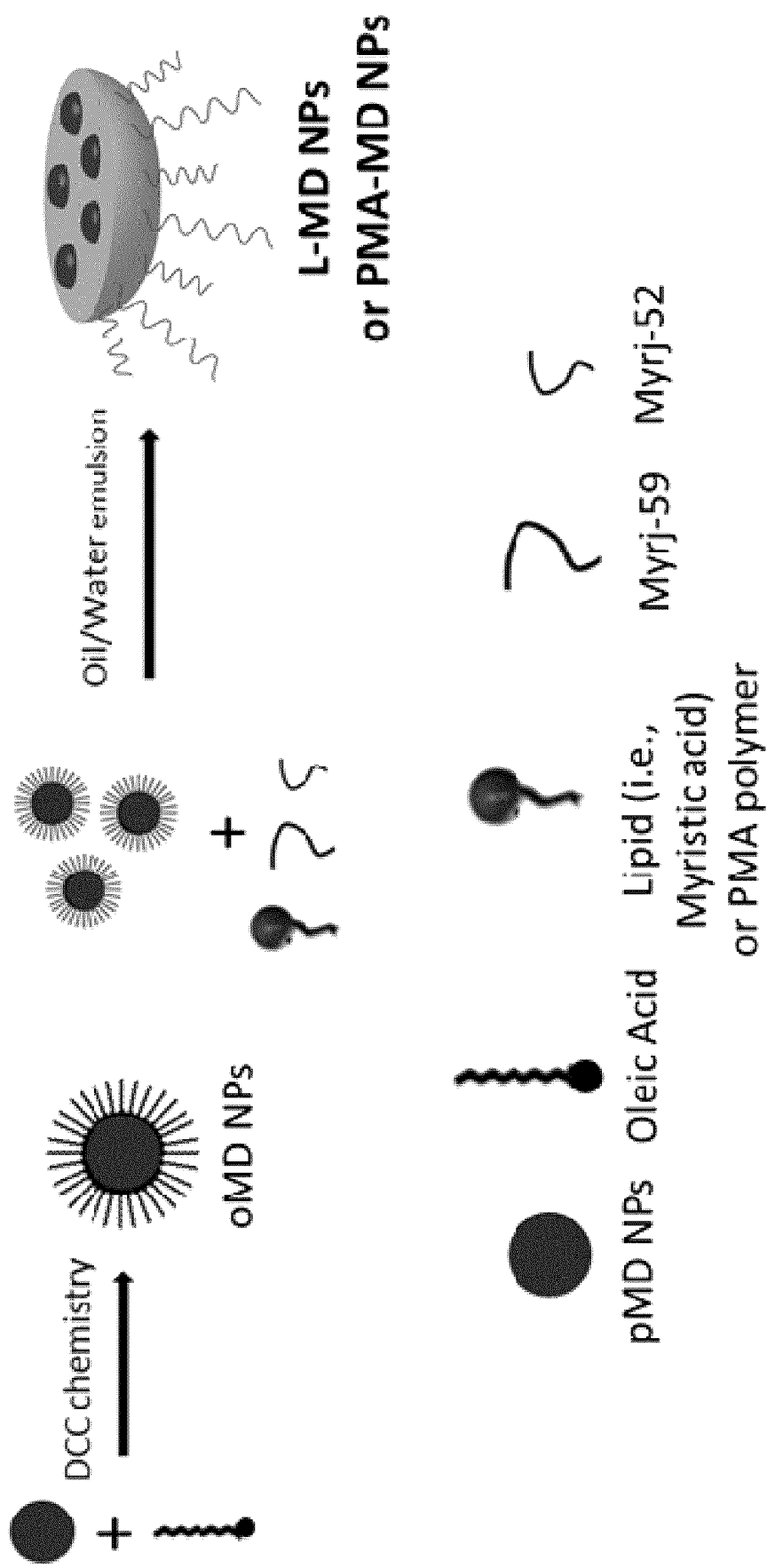
FIG. 16 is a schematic diagram illustrating the different steps during the preparation of oMD NPs L-MD NPs or PMA-MD NPs.

Example 6: Preparation and Characterization of PEG-Lipid Matrix (L-MD) Nanoparticles Loaded with oMD Nanoparticle The oMD NPs loaded lipid based nanoparticles were prepared using myristic acid, polyoxyethylene stearate and polyvinyl alcohol. A schematic diagram illustrating the L-MD formulation is shown in FIG. 16, which can be generalized as a two-step process as follows: step one—pMD NPs are transferred to an organic phase by covalent conjugation with oleic acid to make oMD NPs; and step two—oMD NPs are loaded into a lipid and PEG based matrix. Briefly, a mixture of 10 mg of myristic acid, 2 mg of polyoxyethylene(40) Stearate (Myrj 52) and 3 mg of polyoxyethylene (100) Stearate (Myrj 59) were dissolved in 50 µl chloroform, the solution was then poured into 100 µL of oMD NPs suspension (containing 15 mM MD based on ICP analysis). In a 15 mL conical tube 1 mL of 0.25 wt % polyvinyl alcohol (PVA) was heated at 55° C. using a water bath, after 5 min the mixture containing myristic acid, Myrj 59, Myrj 52 and oMD NPs was emulsified and sonicated for another 5 min at 100% peak amplitude and 5 mm probe depth using a Hielscher UP100H probe ultrasonicator (Hielscher USA, Inc., Ringwood, N.J., USA). After 5 mins., the suspension was immediately transferred to 0.5 mL of ice-cold 0.25 wt % polyvinyl alcohol solution under stirring and gently purged with $N_2$ for 30 min to remove chloroform. Finally, the emulsion was left under low vacuum to confirm the complete removal of organic solvent. To confirm the loading of oMD NPs, obtained L-MD NPs were centrifuged at 14000 rpm for 1 hour and trace of oMD nanoparticles in the supernatant was determined by UV-absorption spectrum. There was no absorbance peak detected, confirming-100% loading of oMD NPs into the lipid nanoparticles.

For in vitro studies, fluorescein amine labelled myristic acid was used for L-MD NPs preparation. For this purpose fluorescein amine dye was covalently linked with myristic acid using the N,N'Dicyclohexylcarbodiimide (DCC) carbodiimide reagent chemistry for cross-linking carboxylic acid of myristic acid with primary amine of fluorescein. The reaction was performed by mixing the myristic acid, fluoresceinamine and DCC at a molar ratio 1:0.5:1 (myristic acid:fluoresceinamine:DCC). Briefly, 100 mg of myristic acid dissolved in chloroform was mixed with 80 mg of DCC dissolved in chloroform under stirring, after 5 min 70 mg of fluoresceinamine dissolved in 1 mL of tetrahydrofuran (THF) was added and the solution was left under stirring overnight. The reaction mixture was protected from light to avoid bleaching of the fluorescent dye. The mixture was then washed with DDI water following the extraction technique; the organic phase containing the fluorescein-labelled myristic acid was separated from the aqueous phase using a separation funnel. The washing step was repeated until no trace of free fluorescein was seen and clear DDI water layer was observed. At the end of washing, the organic layer containing the dye-labeled myristic acid was collected and dried under vacuum for 24 hours. In the last step, the obtained powder was lyophilized over night to remove any traces of water.

For in vivo studies, hydrophobic near infra-red (NIR) dye Indocyanine green (ICG) was co-loaded with oMD NPs in the lipid matrix. 20 µL of 50 mM ICG in methanol was mixed with myristic acid, oMD NPs, Myrj 59 and Myrj52 and emulsified with 0.25 wt % PVA, the L-MD NPs were then prepared using the same method as described above.

Figure 17B:
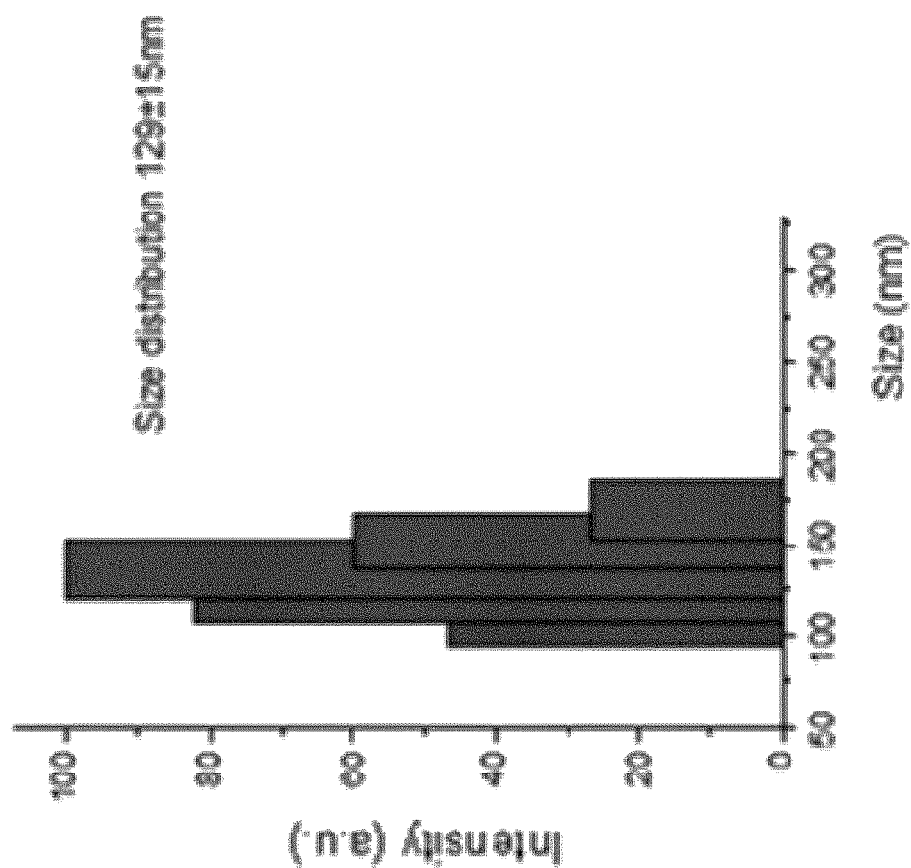
FIG. 17 shows (a) TEM image and (b) size distribution oMD NPs loaded in a PEG-lipid matrix (L-MD NPs). (c) Stability of L-MD NPs in α-medium with 10% FBS, medium with 50% FBS and in pH 7.4 weak buffer (PBS) in the presence of 250 μM $H_2O_2$.
Figure 17A:
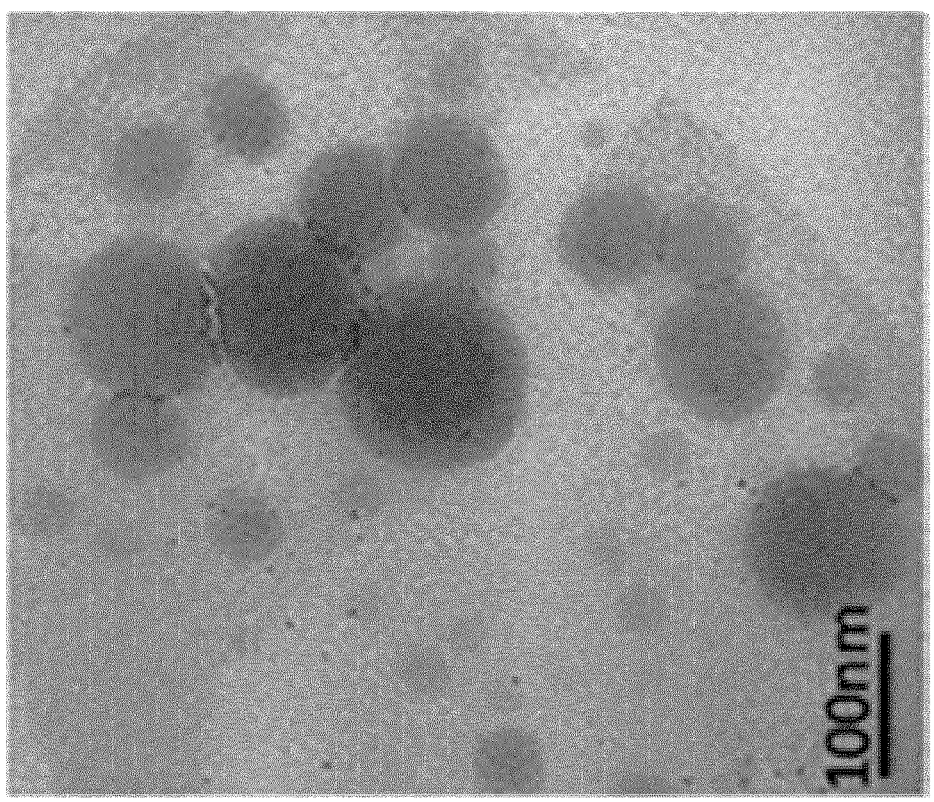
Figure 17C:
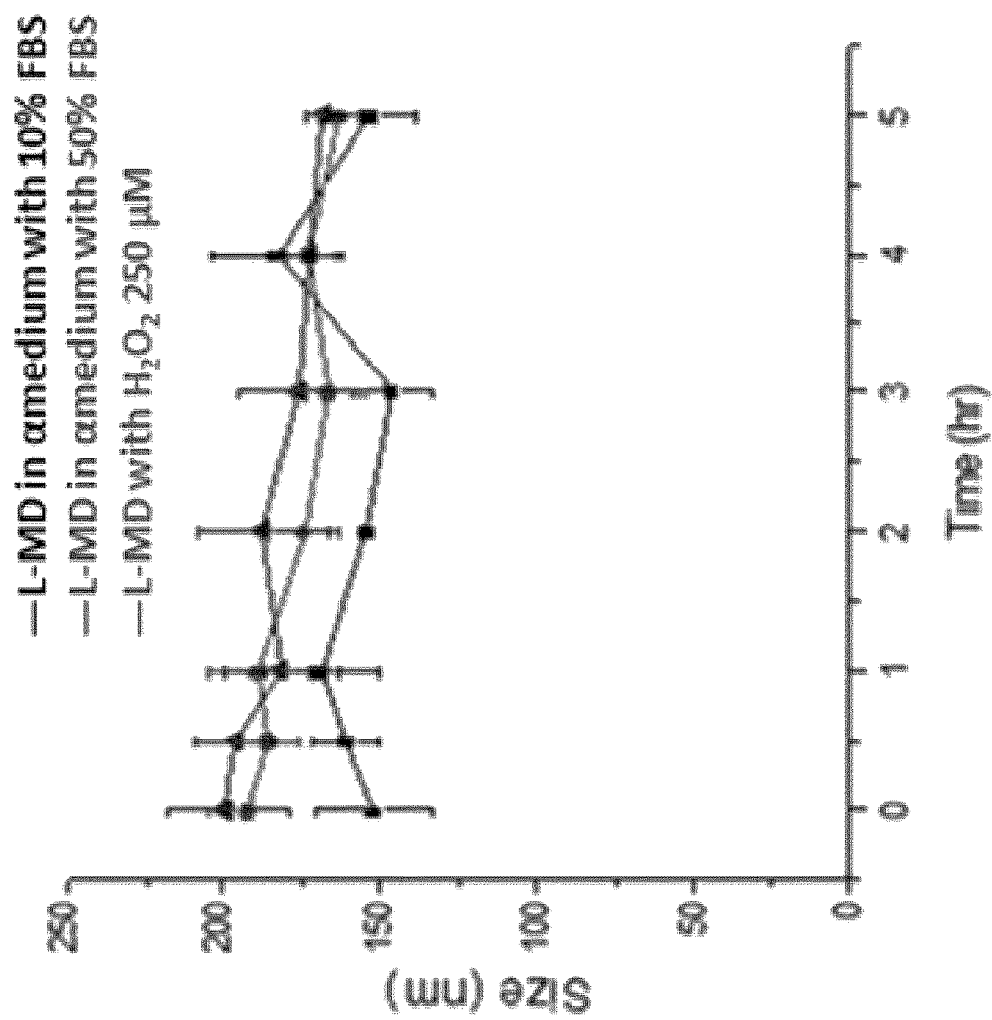

The obtained L-MD NPs were characterized using zeta sizer to confirm the size distribution and surface charge of nanoparticles (FIG. 17b). The results revealed a size distribution of 50-250 nm with negative surface charge of −26 mV. L-MD NPs were also analyzed using transmission electron microscope (TEM) to confirm the size distribution and morphology of particles (FIG. 17a). TEM analysis revealed particles with spherical shape with smooth surface morphology. Results obtained from TEM analysis were in well agreement with zeta size measurements. The stability of L-MD NPs was also examined in α-medium with different FBS concentration (10-50%) and in pH 7.4 weak buffer (i.e. PBS) in the presence of $H_2O_2$(FIG. 17c). These results showed the L-MD NPs were highly stable under physiological conditions.

Example 7: Preparation and Characterization of Amphiphilic Polymer Matrix Loaded with oMD NPs (PMA-MD NPs)

An amphiphilic polymer (PMA) with hydrophilic back bone and hydrophobic side chains was synthesized by reacting poly(isobutylene-alt-maleic anhydride) (~6,000 Da) with hexadecylamine. In a typical reaction, 75% of anhydride rings of the polymer were linked with hexadecylamine through amide linkage between anhydride and $NH_2$ groups of polymer and hexadecylamine respectively. As molecular weight of a single monomer of poly(isobutylene-alt-maleic anhydride) was 154.14 g/mole ($C_4H_2O_3.C_4H8$) the total number of monomer units for 6000 Da polymer molecule were 39. In general, 1.028 g of poly(isobutylene-alt-maleic anhydride) (0.17 mmol=6.6 mmol monomers) was placed in round flask, in a separate glass vial 1.21 g of hexadecylamine (5 mmol) was dissolved with 30 mL of anhydrous tetrahydrofurane at 50° C. and then quickly poured to and vigorously mixed with the polymer powder. The cloudy mixture was sonicated for several seconds (e.g. 30 s) and then kept at 60° C. under vigorous stirring. The initial cloudy solution turned clear after 10 minutes confirming the reaction of maleic anhydride rings with $NH_2$ groups. In order to increase the reaction efficiency between maleic anhydride and primary amine, after 1 hour, the reaction mixture was concentrated roughly up to one fifth of the original volume by evaporating the solvent using a rotavapor system. The concentrated solution was left stirring overnight at 50° C. The solvent was slowly evaporated until the polymer was completely dry (pale yellow solid). Finally, the resulting polymer was re-dissolved in anhydrous chloroform giving the final concentration of 200 mg/mL.

Hydrophobic oMD NPs were loaded in amphiphilic polymer PMA using oil in water emulsion method. A schematic diagram illustration the step for NPs formulation is shown in FIG. 7. Briefly, 50 µL of PMA (200 µg/mL), 50 µL of oMD NPs (30 mM MD based on ICP analysis) dissolved in chloroform, 3 mg of Myr59 and 1 mg of Myrj 52 dissolved in 50 µL of chloroform were mixed and emulsified in 1 mL of 0.25 wt % polyvinyl alcohol at 48° C. The emulsion was sonicated for 5 min using a probe sonicator at 100% peak amplitude and 5 mm probe depth using a Hielscher UP100H probe ultrasonicator (Hielscher USA, Inc., Ringwood, N.J., USA). After required time, the mixture was transferred to ice cold 0.25 wt % polyvinyl alcohol solution under stirring and gently purged with $N_2$ for 30 min to remove chloroform. Finally the PMA-MD NPs suspension was left under low vacuum to facilitate complete removal of organic solvent. To confirm the loading efficiency of oMDNPs, obtained PMA-MD particles were centrifuged at 14 k rpm for 1 hour and trace of nanoparticles in the supernatant was determined by UV-absorption spectrum. There was no absorbance peak detected, confirming ~100% loading of oMD NPs in the PMA-MD nanoparticles.

For in vitro studies, fluorescein amine modified PMA was used to synthesize PMA-MD NPs. For in vivo studies, hydrophobic near infra-red (NIR) dye Indocyanine green (ICG) was co-loaded along with oMDNPs in the core of PMA-MD NPs. For this purpose 20 µL of 50 mM ICG in methanol was mixed with oMD NPs, PMA, Myrj 59, Myrj52 and emulsified with 0.25 wt % PVA, the PMA-MD NPs were then obtained using the same protocol as described above.

Figure 18A:
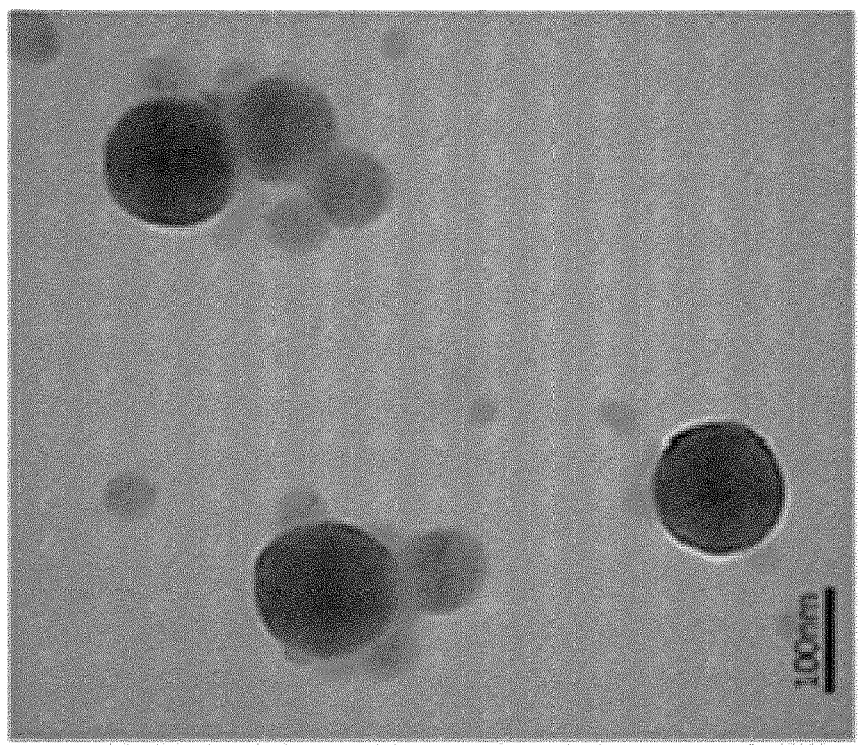
FIG. 18 shows (a) TEM image and (b) size distribution of oMD NPs loaded in an amphiphilic polymer matrix (PMA-MD NPs). (c) Stability of PMA-MD NPs in α-medium with 10% FBS, or 50% FBS and in pH 7.4 weak buffer (PBS) in the presence of 250 μM $H_2O_2$.
Figure 18C:
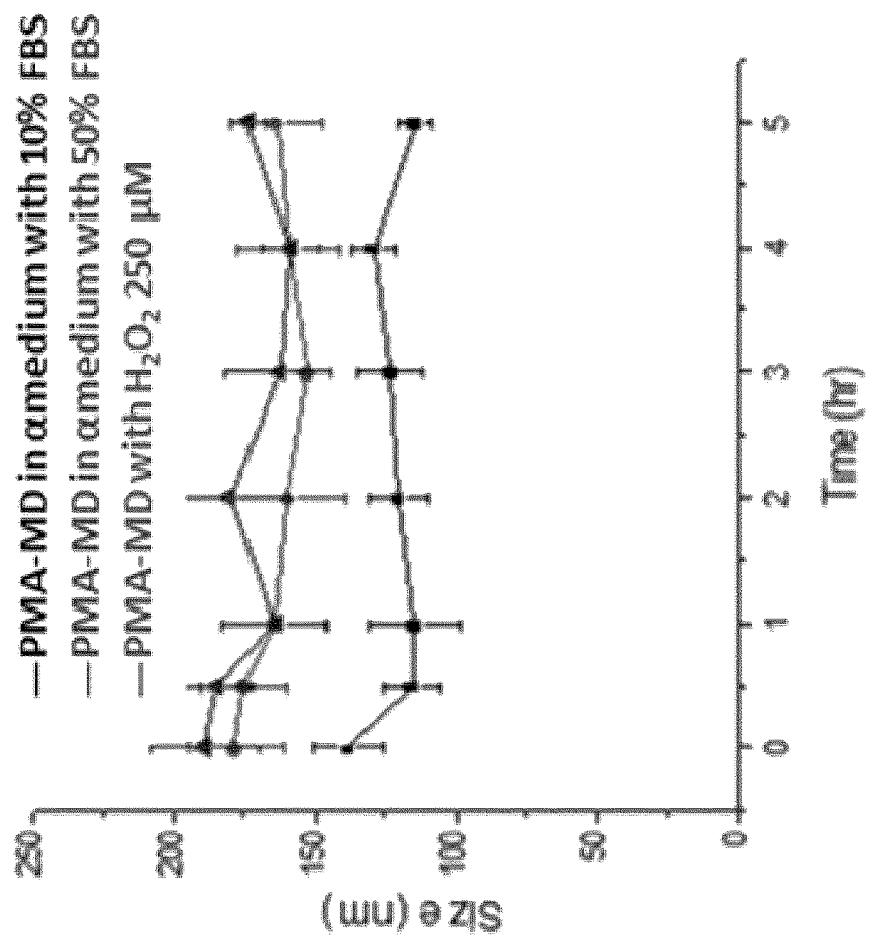
Figure 18B:
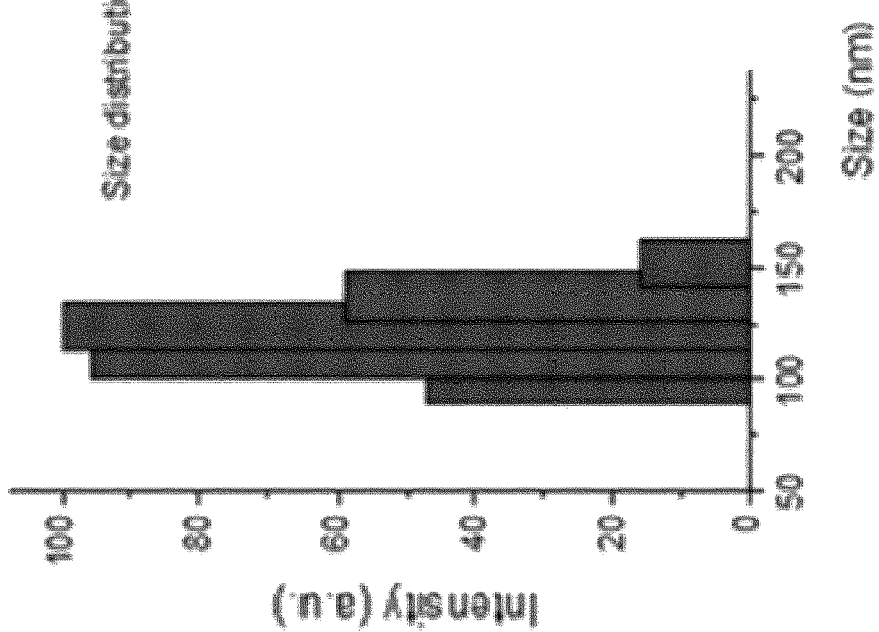

The obtained particles were characterized using zeta sizer to measure the particle size and surface charge. The results confirmed particle size of 50-250 nm with negative surface charge of −27 mV (FIG. 18a). The particles were also analyzed under transmission electron microscope (TEM), to examine the particle size and morphology of NPs (FIG. 18b). The TEM analysis revealed smooth and spherical morphology of the PMA-MD NPs. The colloidal stability of the PMA-MD NPs was examined in α-medium with different FBS concentration (10-50%) and in pH 7.4 weak buffer (i.e. PBS) in the presence of $H_2O_2$(FIG. 18c). The results showed that the PMA-MD NPs were highly stable under physiological conditions.

Example 8: In Vitro Oxygen Generation and pH Change Measurements without Cells

Figure 19:
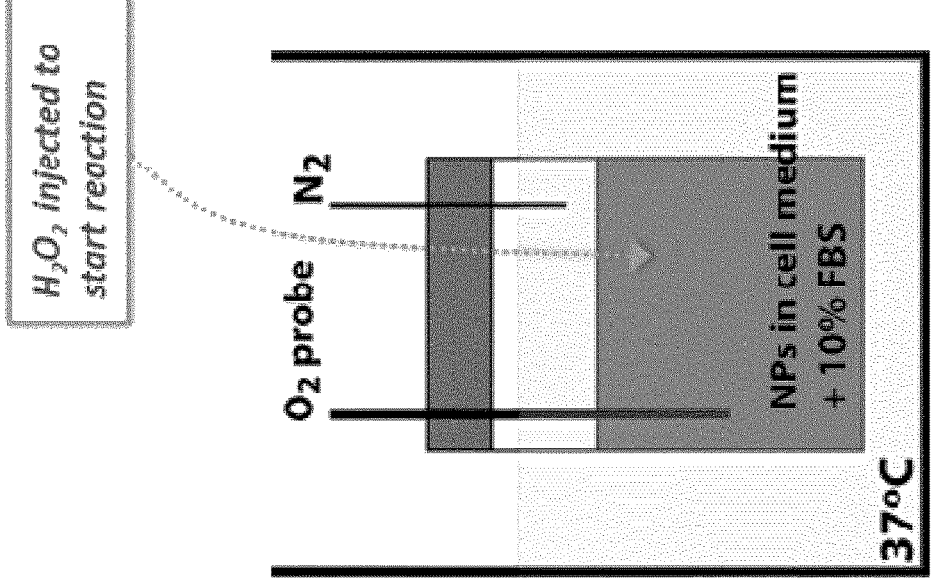
FIG. 19 shows a schematic of the apparatus for measurement of generated Oxygen.

Oxygen ($O_2$) generated by MD containing NPs and pH changes was measured in a semi-sealed chamber coupled with a MI-730 micro-oxygen electrode and a MI-407 pH+MI 402 reference microelectrodes (Microelectrodes Inc, USA), at 37° C. In brief, in a small glass vial a predetermined aliquot of NPs was added to 3 mL of saline or αMEM cell medium containing 10% FBS to give various MD concentrations (10-150 µM). The vial was sealed with parafilm and pierced with the probes and two hypodermic needles for gassing, as represented in the schematic in FIG. 19. The vial was placed in a water bath with temperature set to 37° C. and bubbled with $N_2$ for 30 min to remove dissolved $O_2$. When oxygen levels reached concentration close to zero (as indicated by the $O_2$ probe), 7.5 µL of a $H_2O_2$ solution in DDI water (100 mM) was inject to the solution to initiate $O_2$ generation. Oxygen generation and/or pH changes were monitored every 60 s using an Oakton pH 1100 (Thermo Fisher Scientific Inc., USA) coupled with $O_2$-ADPT Oxygen Adapter (Microelectrodes Inc., USA) for $O_2$ measurements. Electrodes were calibrated according to manufacturer's instructions. Saline or αMEM medium with 10% FBS was used as control.

Figure 20:
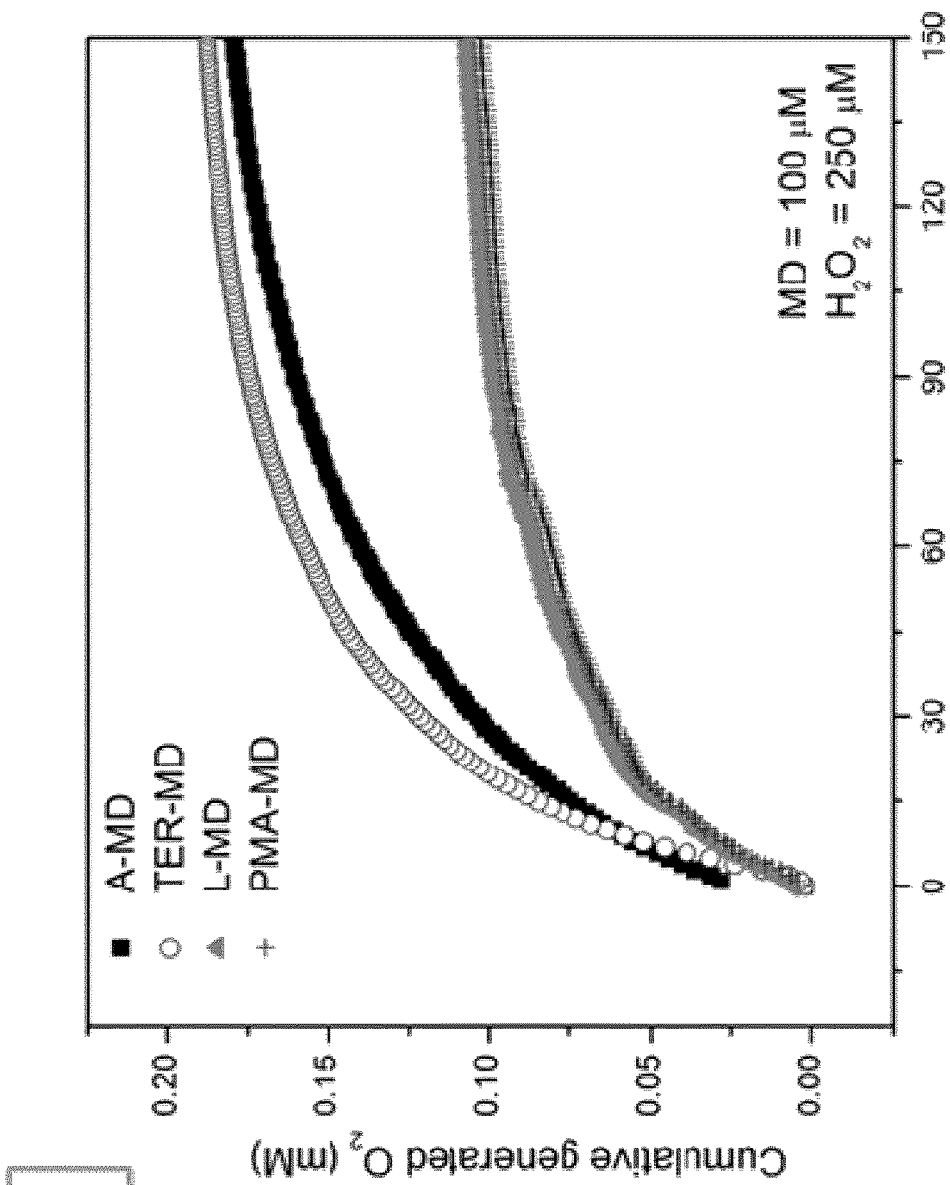
FIG. 20 shows $O_2$ generation by addition of $H_2O_2$ (250 μM) to various MD NP formulations. A-MD, TER-MD, L-MD and PMA-MD NPs. Measurements were performed (n=3) in cell culture medium containing 10% FBS at 37° C.

The oxygen generation curves of different MD-containing NP formulations are compared in FIG. 20. All formulations (albumin, lipid and polymer-based) generated measurable amounts of oxygen at endogenous concentrations of $H_2O_2$. Significant amounts of $O_2$ (up to 0.20 mM within 30 min) was produced by the reaction of 100 µM of MD with 250 µM $H_2O_2$. The results showed that the kinetics of the MD reaction towards $H_2O_2$ and rates of oxygen generation and can be controlled by the carrier. More hydrophobic PMA-MD and L-MD NPs loaded with oMDNPs showed slower oxygen generation than to the more hydrophilic albumin-containing A-MD and TER-MD NPs. These observations suggest that the MD NP formulations can be engineered for fast oxygen generation (e.g. A-MD and TER-MD) or for slow, prolonged oxygen generation (e.g. lipid-based PMA-MD and L-MD).

Example 9: Multifunctionality of A-MD Nanoparticles in Culture Medium

The multifunctionality of the A-MD NPs to generate $O_2$ and to increase the medium pH in vitro upon reaction with $H_2O_2$ at endogenous levels was examined. The reaction between MD and $H_2O_2$ is a complex reaction leading to the decomposition of $H_2O_2$ and the production $O_2$ as summarized in FIG. 5a. Besides the production of $O_2$, the reaction causes an increase in the local pH by the consumption of $H^+$ ions and the production of an intermediate Mn-oxo-hydroxide $(MnOOH)$[26]. This phenomenon can be particularly useful for the regulation of local pH in cancer cells and tumour tissue. Hence we studied if A-MD NPs would generate measurable amounts of oxygen and increase pH at low concentrations of $H_2O_2$ found in the human body (i.e., 100 μM and up to 1 mM)[33]. It was observed that at a very low concentration (~45 μM of MD), the NPs were able to completely quench 1 mM $H_2O_2$ in cell medium within 40 minutes (FIG. 5b). Further investigation of the $O_2$ generating properties of the NPs used an in-house-made hypoxia-maintaining chamber coupled with both a commercially available oxygen probe and a pH microelectrode 9. Significant amounts of $O_2$ was produced (FIG. 5c) accompanied by an increase in the pH of physiological buffer (phosphate/saline buffer) by one pH unit from pH 6.8 to pH 7.8 (FIG. 5d) by the reaction of 45 μM of MD with 250 μM $H_2O_2$. In an attempt to simulate in vivo conditions where $H_2O_2$ is continuously generated by tumor cells, we measured the $O_2$ production by the NPs during the continuous addition of exogenous $H_2O_2$ (250 μM) into the chamber every 30 min. We observed that a single dose of the NPs (90 μM MD) continuously generated $O_2$ for at least 6 cycles of 30 min each (FIG. 5e). These results demonstrated that $H_2O_2$ and protons can diffuse rapidly across the polyelectrolyte-albumin complex, access the reactive sites of the MD cores, produce $O_2$ and increase pH in a sustained manner under hypoxic conditions.

Example 10: In Vitro Oxygen Generation in Presence of Hypoxic Cancer Cells $O_2$ generated by MD-containing NPs was measured in a semi-sealed chamber coupled with a MI-730 micro-oxygen electrode (Microelectrodes Inc, USA), at 37° C. In brief, in a small glass vial murine breast cancer EMT6 cells ($10^5$ cells per mL) were suspended and stirred in αMEM medium. The vial was plugged with rubber stoppers and pierced with the oxygen probe and two hypodermic needles for gassing, as represented in the schematic in FIG. 21a. The cell suspension was made hypoxic by introducing a mixture of 95% $N_2$ and 5% $CO_2$ for 20 min at 37° C. When oxygen levels reached concentration close to zero (as indicated by the $O_2$ probe), a small aliquot of the NPs was injected to make the MD concentration in the medium 100 μM and the oxygen levels monitored every 60 s using an Oakton pH 1100 (Thermo Fisher Scientific Inc, USA) coupled with $O_2$-ADPT Oxygen Adapter (Microelectrodes Inc, USA). Electrode was calibrated according to manufacturer's instructions. αMEM medium with 10% FBS, with or without cells was used as control.

Figures 21, 22:
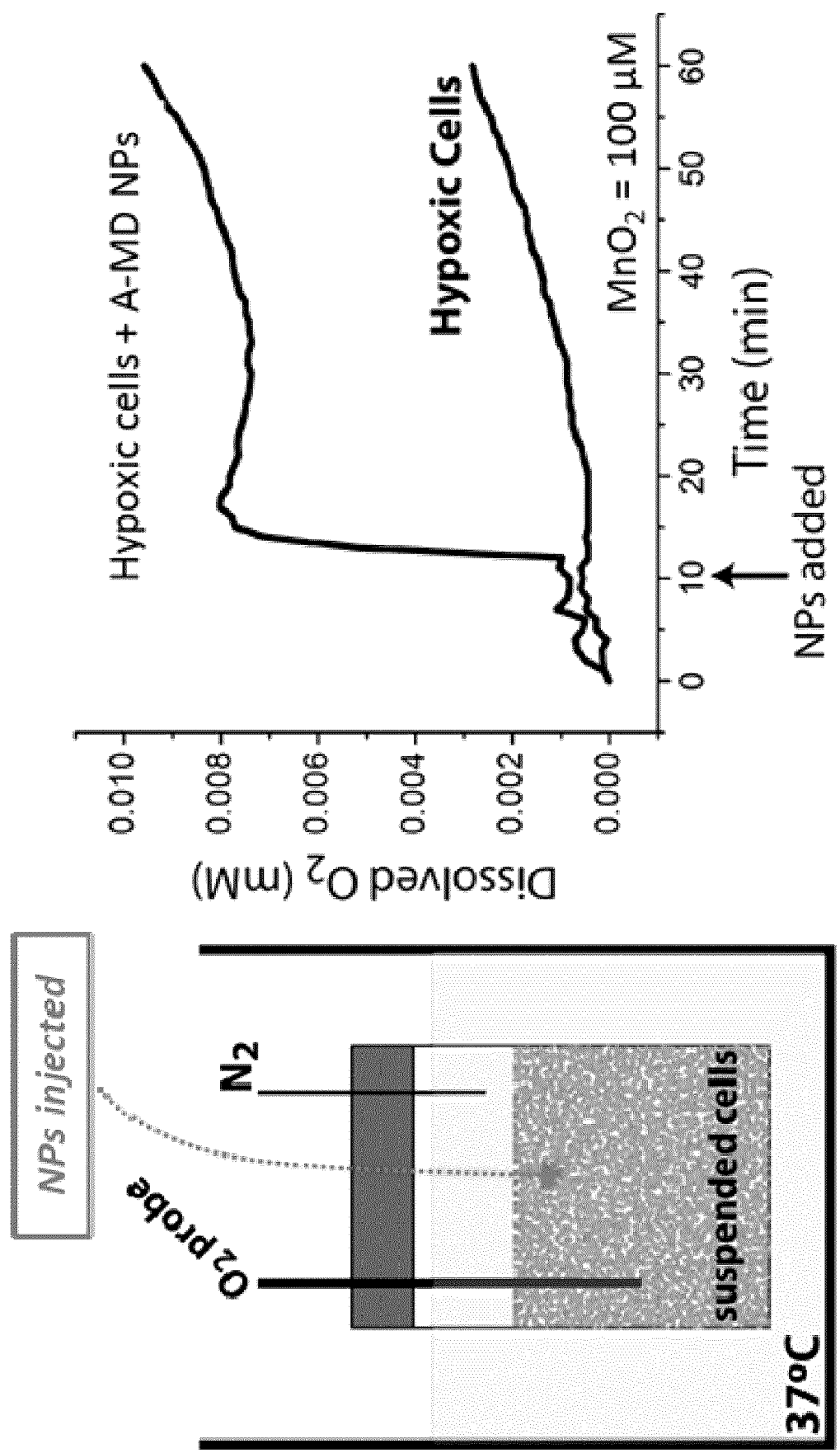
FIG. 21 shows a schematic of the apparatus for measurement of generated Oxygen with suspended hypoxic cells.
FIG. 22 shows $O_2$ generation by A-MD NPs incubated with suspended hypoxic cancer cells (n=3). Suspended cells are made hypoxic and upon addition of NPs to the culture oxygen is generated by the reactivity of the MD content of the NPs towards $H_2O_2$ released by hypoxic cancer cells. Measurements were performed (n=3) in cell culture medium containing 10% FBS at 37° C.

FIG. 21b shows that protein-based MD (A-MD) NPs incubated with hypoxic breast cancer cells reacted quickly with endogenous $H_2O_2$ produced by the cells under hypoxic stress, thus producing $O_2$. Significant amounts of $O_2$ (~6-fold increase of $O_2$ levels in the medium) were detected within 2 min by reacting with $H_2O_2$ released by the cancer cells. These results indicate that the endogenous levels of $H_2O_2$ released by hypoxic cancer cells in vitro is sufficient to react with the NPs and generate measurable $O_2$ without addition of exogenous $H_2O_2$ to the culture medium.

Example 11: Cytotoxicity and Cellular Uptake of Various $MnO_2$ NP Formulations

Figure 6A:
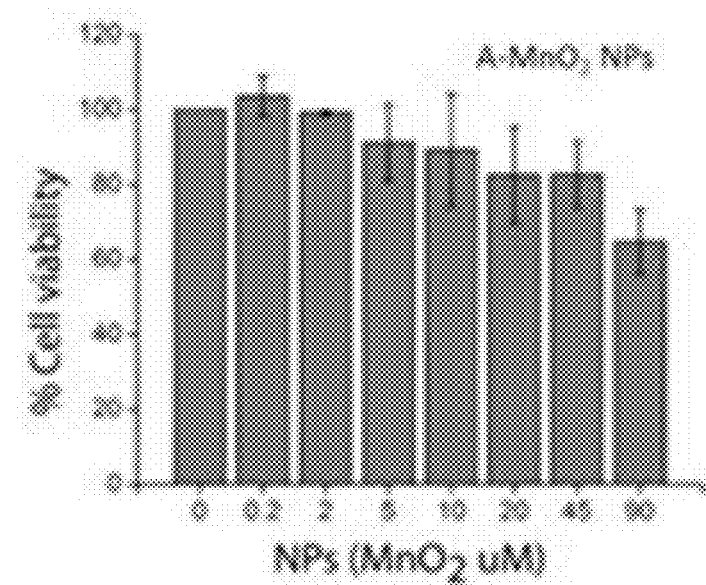
FIG. 6 shows cytotoxicity and cellular uptake of various MD NP formulations. (a) Viability of murine EMT6 cancer cells (10$^5$ cells/mL) exposed to various concentrations of A-MD NPs for 48 h. Viability of (b) human breast cancer MDA-MB 231 and (c) murine breast cancer EMT6 incubated with L-MD and TER-MD NPs for 48 h. (d) Uptake of A-MD NPs at 37° C. by EMT6 murine breast cancer cells after 1 h incubation determined by fluorescence microscopy. (e) TEM images of cellular uptake of A-MD NPs. (f) and (g) show cellular uptake of different MD NPs formulations at various time points. TER-MD: MD NPs loaded in a terpolymer crosslinked denatured protein matrix; L-MD and PMA-MD: oleic acid-conjugated MD (oMD) loaded in PEG-lipid and amphiphilic polymer, respectively. Percent of cell viability was determined with MTT assay. (n=3) Error bars represent standard errors of the mean.
Figure 6B:
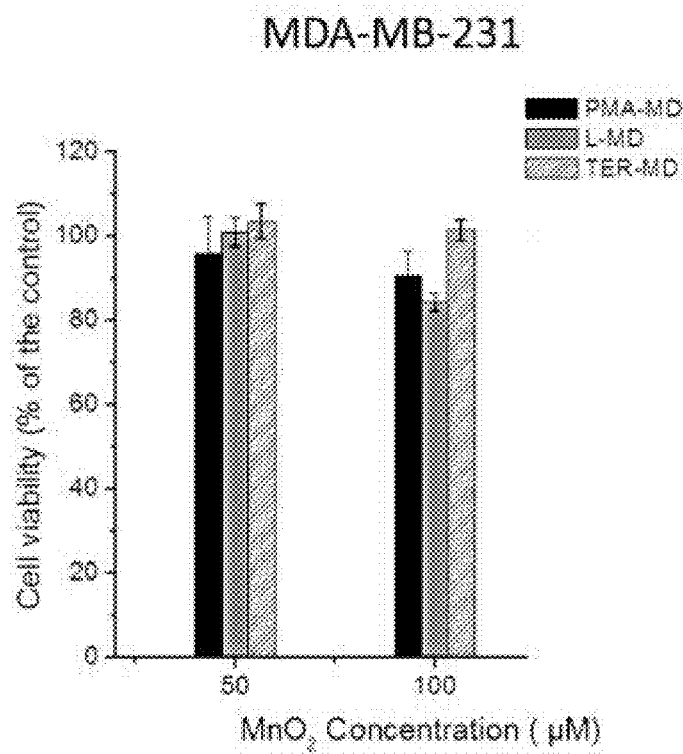
Figure 6C:
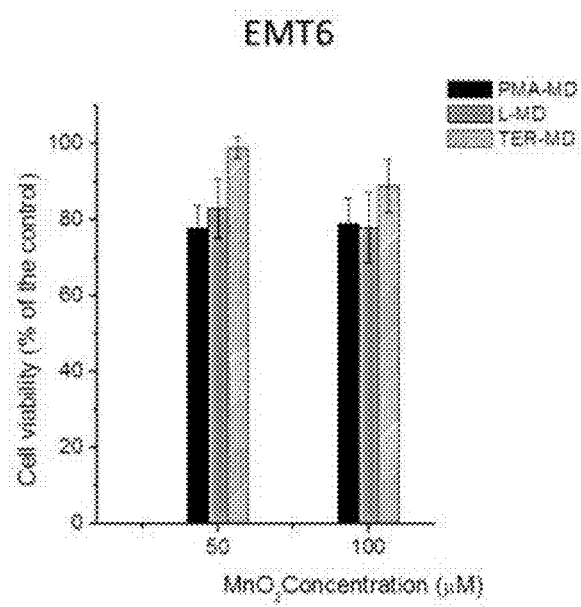
Figure 6E:
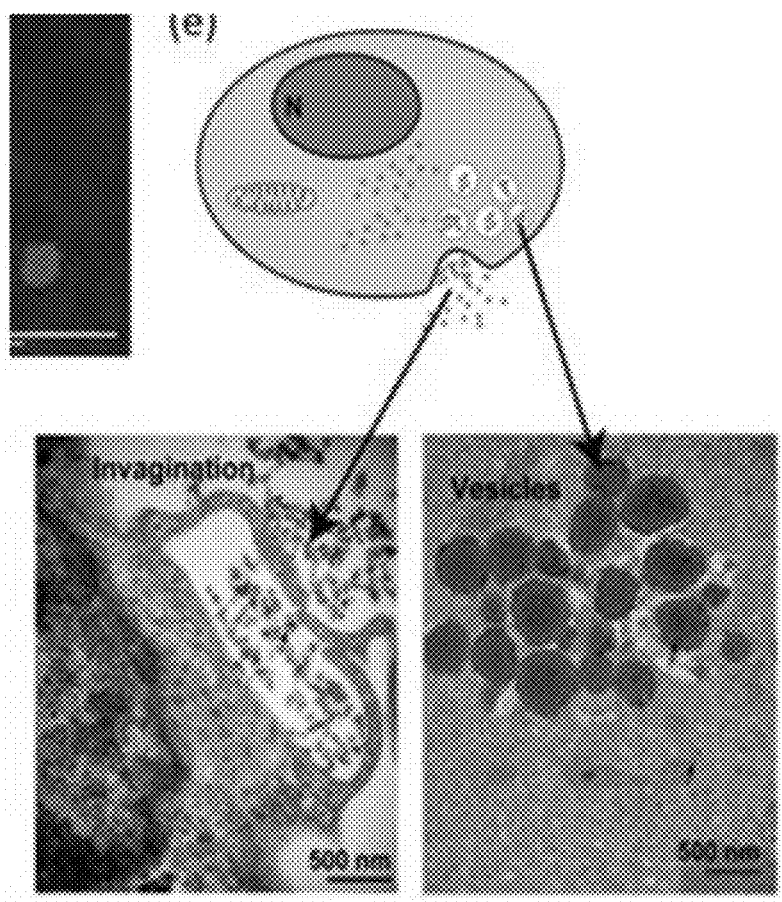

The viability of human breast cancer MDA-MB 231 and murine breast cancer EMT6 exposed to various concentrations of MD NPs for 48 h was evaluated. In brief, platted cells (10 000 cells per well/96 well plate) were incubated with different NP formulations dispersed in α-medium at desired concentrations (i.e., for 50 and 100 uM $MnO_2$). Cells were incubated with NPs for 48 h Murine EMT6 breast tumor cells ($10^5$ cells) were incubated for 1 h with MD NPs (45 μM) at 37° C. before microscopic analysis. Cell uptake of NPs by transmission electron microscopy (TEM) was performed using a H7000 TEM microscope (Hitachi, Japan), following standard methods for sample preparation. An EVOS fluorescence microscope (AMG, USA) was used to image live cells following incubation with red fluorescent dye labelled A-MD NPs. Cell nuclei were stained blue with HOESCHT 33342 (Invitrogen Molecular Probes, USA). The cellular uptake of NPs at various time points was also evaluated. For this experiment, NPs were made fluorescent by conjugating fluorescein isothiocynate (FITC) to the NPs as previously described. Platted cells (500,000 cells per well/6 well plate) were incubated with FITC labelled MD NPs dispersed in culture medium at the concentration 100 μM MD. Cells were incubated with NPs for several time points: 0.5, 1, 2, 4 and 24 h. After incubation time cells were washed twice with PBS, trypsinized and replated in 96 well plate (10,000 cells per plate). Fluorescence was measured with a microplate reader, ex: 485 nm and em: 520 nm. These results are summarized in FIG. 6. Cell viability studies showed that all formulations (A-MD, L-MD, TER-MD and PMA-MD NPs) are not toxic to the cancer cells at MD concentrations used in vitro and in vivo (i.e., 100 μM MD) (FIGS. 6a-c). It is known that the aberrant metabolism of cancer cells leads to significantly elevated cellular concentrations of $H_2O_2$ If the NPs could be taken up by cancer cells, they could react quickly with endogenous $H_2O_2$ produced by cancer cells under hypoxic stress, thus producing $O_2$ in situ. To test this hypothesis, the cellular uptake of the NPs was determined by incubating EMT6 murine breast cancer cells with fluorescence-labelled A-MD NPs, and observed significant cellular uptake of NPs within 60 min of incubation (FIG. 6d). This finding was confirmed by transmission electron microscopy (TEM). TEM images (FIG. 6e) showed EMT6 cells in vitro underwent membrane invagination and engulfment of the NPs and the NPs taken up by the cell were distributed within the cell cytoplasm and vesicles after 1 h incubation. Different formulations showed similar cellular uptake profile over the time for two different cancer cell lines (FIGS. 6 f-g). Cellular uptake of the NPs was observed within 60 min of incubation with EMT6 cells (FIG. 6f).

Example 12: Animal Tumor Models for In Vivo Studies

For in vivo studies, transplantable mouse mammary tumor cells EMT6 were grown in eight-week old female Balb/c mice (Jackson Laboratory, Bar Harbor, Me., USA). For this purpose $1\times10^6$ EMT6 cells suspended in 30 μL of cell culture medium (αMEM, 10% FBS) were inoculated in the mammary fat paid of mice. Briefly, for the breast tumor model mice were anaesthetized with 1% isoflurane and injected with a pain killer (buprenorphine, 0.05 mg/kg), a 5 mm incision was made in the skin over the lateral thorax, exposing the mammary fat pad. A 30 μL volume of $1\times10^6$ EMT6 cells in cell culture medium (αMEM, 10% FBS) was injected into the mammary fat pad using a 27-gauge needle. Exposing the fat pad ensured the injection of cells into the fat pad and not into the subcutaneous space. The incision was closed with sutures and surgical glue and the mice were monitored during recovery until sternal recumbency was observed, at which point the mice were returned to a clean cage. Mice were monitored daily for 2 days after tumor implantation, and tumor growth was monitored weekly until reaching the desirable size, approximately 100 mm³ for irradiation experiments (about 2 weeks) and 300-400 mm³ for biodistribution studies (about 3-4 weeks). Tumors were implanted in one or two sides of the animal, depending on the experiment. All animal experiments were performed in accordance with guidelines and regulation of animal Care Committee at University Health Network (AUP 2407). The animal care committee operates under the standards of animal care set forth by the Canadian Council of Animal Care.

Example 13: In Vivo Biodistribution of Different MnO$_2$ NPs Formulations

The in vivo biodistribution and tumor accumulation capacity of different formulations was determined using EMT-6 grafted Balb/c mice following tumor growth to volumes of 300-400 mm³. Once tumor reached the required size, 100 μL of formulation such as TER-MD, L-MD or PMA-MD (1 mM MD based on ICP analysis) was intravenously injected through the tail vein of the animals. The NIR-labelled formulation were synthesized by co-loading the near infra-red dye ICG (in case of L-MD and PMA-MD), whereas in case of TER polymer NPs ICG was linked to the particles surface through electrostatic interaction. After the injection, biodistribution and tumor uptake characteristics of the NPs were monitored non-invasively for up to 24 hours using the Xenogen IVIS Spectrum Imaging System (Caliper Life Sciences Inc., USA). During imaging, mice were anaesthetized with isoflurane, and whole body fluorescence images were acquired using 745 nm excitation and 820 nm emission filters. For all of the recorded images, the fluorescence intensity was equalized. For ex vivo biodistribution studies at 4 and 24 hours after injection, the animals were euthanized and the organs were collected. Ex vivo fluorescence images of whole organ was obtained using the Xenogen IVIS Spectrum Imaging System. The biodistribution and ex vivo images of the resected organs (FIGS. 15 a-b) showed that NPs (lipid- and polymer-based) reached and accumulated in the tumor site within 1 h post i.v. injection and remained in the tumor during 24 h duration of the experiment.

Example 14: Effect of L-MD and TER-MD Nanoparticle Formulations on Enhancement of Radiation Therapy Solid tumors of EMT6 murine breast cancer cells were grown orthotopically in Balb/c mice. Cells were implanted on both sides and treatments were initiated when the tumors reached an approximate volume of 100 mm³. Mice were divided into 6 groups (n=3/group): 1) Saline, 2) Saline+RT, 3) TER-MD NPs, 4) TER-MD NPs+RT, 5) L-MD NPs, 6) L-MD NPs+RT. Tumors on both sides were treated with 50 μL intratumoral (i.t.) injection of different MD NP formulations (1 mM MD in saline) or saline (control). The mice were restrained in a specially designed acrylic box, and the tumors from only one side were irradiated locally with 10 Gy, 30 min post i.t injections. In one experiment, mice were sacrificed 24 h post-treatment and tumors were resected, formalin fixed and analyzed for: histopathology analysis (H&E), apoptosis (using terminal deoxynucleotidyltransferase UTP nick end labelling (TUNEL), cell proliferation (Ki-67), and DNA double-strand breaks (DNA DSB) (anti-gamma-H2AX antibody).

In another experiment, the tumor size was measured as a function of time with vernier calipers in two dimensions and tumor volumes were calculated by the formula V=[(length)× (width)²]/2. At the end of experiment (i.e., 5 days post-treatments), the animals were sacrificed and the tumor masses were excised and weighed. Tumor tissue was also formalin fixed and stained for: histopathology analysis (H&E). Tumor tissue preparation and analysis were performed by the CMHD Pathology Core laboratory at Mount Sinai Hospital, Toronto. Slides were scanned with a Nano-Zoomer 2.0 RS whole slide scanner (Hamamatsu, Japan) and images were analysed with Visiopharm 4.4.4.0 software.

Figure 24A:
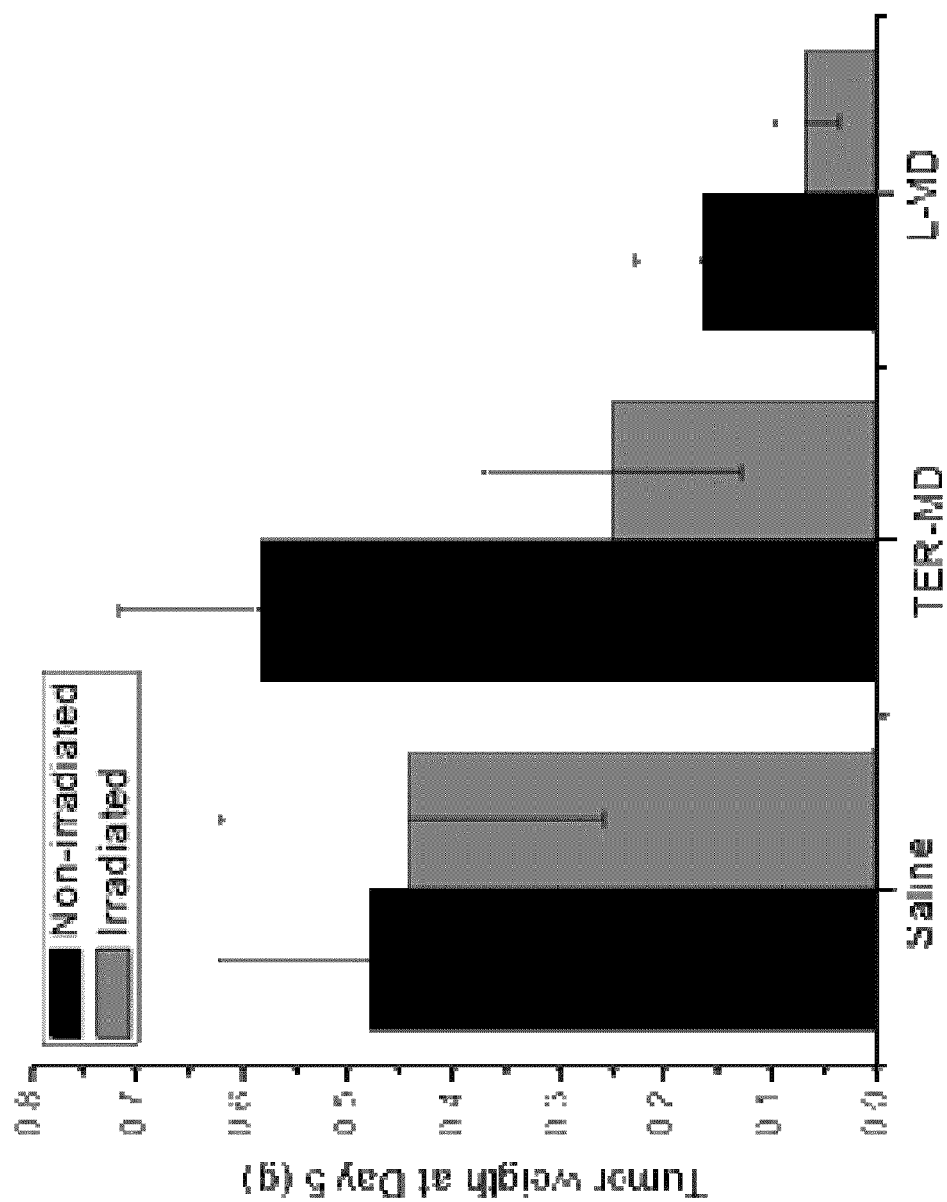
FIG. 24 shows effect on tumor weight of a single treatment with various MD-containing NP formulations and NPs+RT at Day 5 post the treatment. (a) Ex vivo measurement of tumor weight at the end of Day 5. (b) Pictures of tumors taken 5 days post treatment. (c) Images of three tumor samples taken from the same treatment group (not to scale).

A significant change in tumor volume was observed in mice treated with the combination of NPs and RT compared to saline control groups. The combination of TER-MD NPs+RT and L-MD NPs+RT led to tumor regression of −31% and −87% of initial tumor volume, respectively (FIG. 23a). Moreover, L-MD NPs alone led to a tumor volume regression of about −44% (FIG. 23b). Tumor weight was also significantly lower in the NPs+RT groups (FIG. 24a). Decreased tumor weight was observed in the L-MD NP alone treated group compared to saline and TER-MD groups (irradiated and non-irradiated). Visual analysis of resected tumors also showed smaller, less vascularized and less inflammatory tumors in the NP+RT treated groups than saline group (FIGS. 24 b-c).

Figure 25:
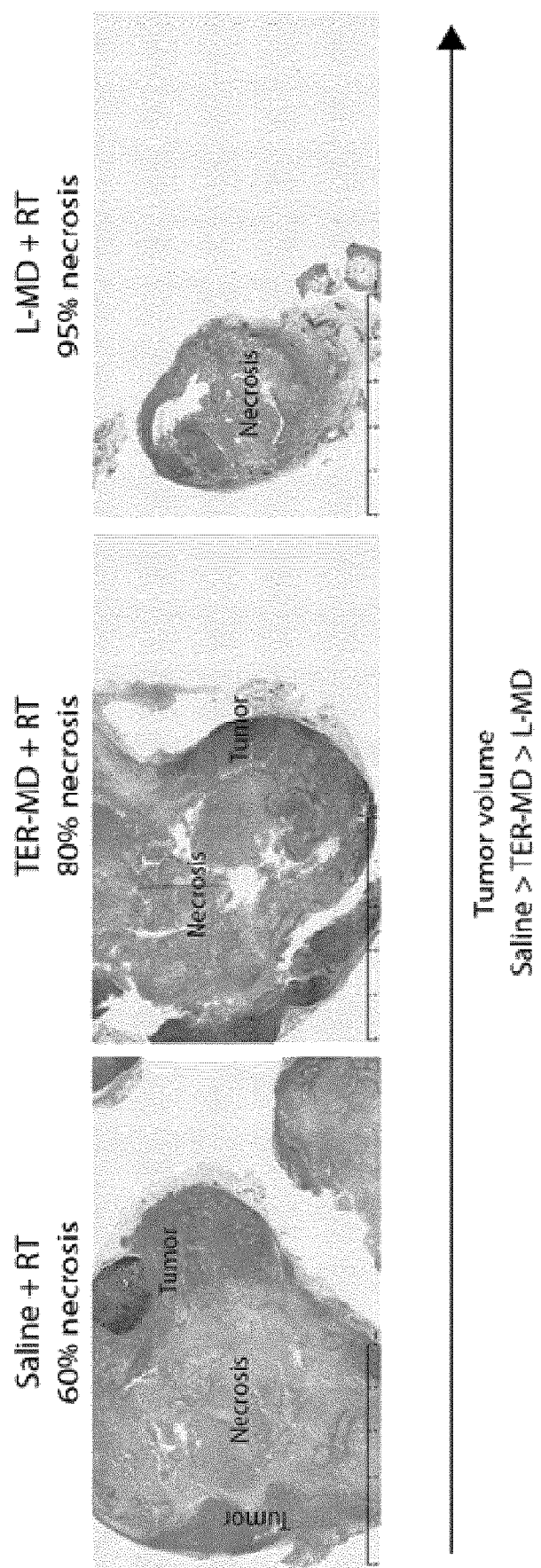
FIG. 25 shows effect of the combination of irradiation with L-MD and TER-MD NPs on tumor necrosis. Panel: Representative Hematoxylin and Eosin (H&E)-stained tissue sections of EMT6 tumors after treatment with NPs+RT–5 days post-treatment (saline was used as a control). Tumors treated with NPs+RT showed massive necrosis. Overall, L-MD NPs+RT group are the smallest in the group and by far the most necrotic. Scale bar=5 mm.

Histopathology analysis of resected tumor tissue revealed that the combination of NPs with irradiation led to significant increase in tumor necrosis as compared to the control group (FIG. 25). Tumors treated with L-MD or TER-MD NPs+single irradiation dose (10 Gy) showed massive tumor necrosis (80-85% and 90-95% of the total tumor area, respectively), while saline+RT group showed only 50-60% tumor necrosis 5 days post-treatment. For L-MD+RT treated group, only the fibrous capsule of the tumor was left 5 days post-treatment, indication of almost total regression of the tumor. Also, treatment with L-MD NPs alone led to similar tumor necrosis as saline+RT group, about 60% of the total tumor area.

The percentage of tumor apoptotic areas was also determined by TUNEL staining. Tumors treated with L-MD NPs+RT showed a four-fold increase in cell apoptosis compared to the control (saline+RT) group. Moreover, tumors treated with L-MD NPs alone showed comparable cell death to the saline+RT group.

Figure 26B:
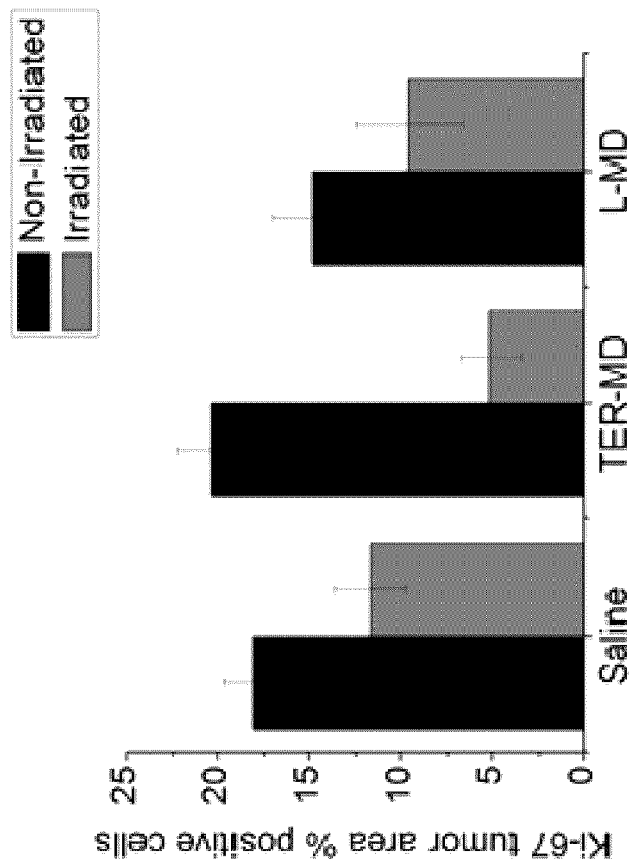
FIG. 26b shows increased radiation-induced necrosis in human PC3 prostate cancer cells treated with L-MD NPs in vitro. Representative Hematoxylin and Eosin (H&E)-stained tissue sections of PC3 tumors after treatment with saline+RT (Left Panels) or L-MDNPs+RT (Right Panels) 5 days post-treatment. Tumors treated with NPs+RT showed significant necrosis while there was no histological evidence of necrosis in the saline control group. Scale bar=4 mm (1.25×) and 1 mm (3×). (c) The in vivo biodistribution and tumor accumulation of ICG-loaded L-MD nanoparticles in a male SCID mouse bearing PC3 prostate tumor implanted into abdominal side. Images were recorded both at the (i) prone and (ii) supine positions. Fluorescence images of tumor-bearing mice were obtained prior to i.v. (base line), and at different time points up to 24 hours post-injection. Tumor is shown with arrow. d) Ex vivo fluorescence images of different organs collected after 24 hours of nanoparticle administration.
Figure 26A:
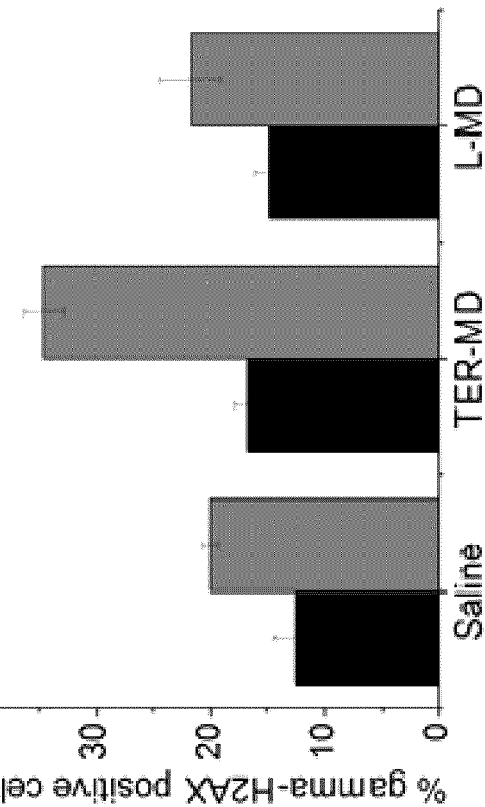
FIG. 26 shows evaluation of the acute effect of MD-containing NP formulations and NPs+RT–24 h treatment. (a) Quantification of DNA DSBs determined by measuring % of positive gamma-H2AX cells in EMT6 tumors treated with Saline, L-MD NPs and TER-MD NPs. (b) Quantification of cell proliferation marker Ki-67.

The immediate effect of the NP formulations on the irradiation-induced cell kill was determined by measuring radiation-induced DNA damage 24 h post-treatment by using gamma H2AX staining to stain for DNA DSBs. These results showed that combined treatment with TER-MD NPs and irradiation resulted in increased DNA damage (35%) compared to the saline control with irradiation (20%) in the EMT6 solid tumor (FIG. 26a). This enhanced effect can be attributed to the fast oxygen generation properties of the hydrophilic formulation.

The effect of the treatments on the cell proliferation was determined by staining using the cell proliferation marker Ki-67. In all groups, irradiation treatment consistently led to decreased cell proliferation compared to respective non-irradiated groups (FIG. 26b). However, the combination of NP treatment and RT led to an even higher decrease in cell proliferation. Treatment with TER-MD NPs decreased cell proliferation from 20% to 5% 24 h post-irradiation, while saline-treated group went from 18% to 11% cell proliferation 24 h post-irradiation. Interestingly, decreased cell proliferation was observed following treatment with L-MD NPs alone when compared to the saline control (15%).

Example 15: Safety of MD Nanoparticles Formulations

EMT6 murine breast cancer cells were grown orthotopically in Balb/c mice. Mice were divided into 3 groups (n=3/group): 1) Saline, 2) TER-MD NPs and 3) L-MD NPs. Treatments were initiated when the tumors reached an approximate volume of 300 mm$^3$. The mice received daily 100 µL intravenous injections of the treatments (1 mM MD in saline or saline) for 7 consecutive days. At the end of experiment, the animals were sacrificed and the organs (lungs, heart, kidneys, spleen and liver) were resected, formalin fixed and H&E for histopathology analysis.

The safety of the NPs to healthy tissue was evaluated through histological analysis of the organs. There was no histological evidence of accumulated toxicity in the different organs associated with i.v. administration of TER-MD and L-MD NPs once daily for 7 days, demonstrating the excellent in vivo biocompatibility of these NP formulations.

Example 16: MD NPs as Radiosensitizers in Prostate Cancer Cell Lines and In Vivo Human Prostate Cancer Model In vitro studies using the human PC-3 prostate cancer cell line were conducted. PC-3 cells were cultured in alpha-MEM media supplemented with 10% FBS. The cells were plated in 96-well plate (1000 cells/well) and incubated for 6 hours at a temperature of 37° C. and 5% $CO_2$. Cells in hypoxia group were then incubated in hypoxic work station (HypOxystation H35, HypOxygen, MD) at 37° C. and 0.2% $O_2$ for 18 hours; cells in normoxia group were left in the 5% $CO_2$ incubator for a total of 24 hours. On the second day, the cells were exposed to MD NPs (100 µM, suspended in saline) either in hypoxia chamber or in normoxia for 1 hour, followed by irradiation (X-Rad 320, Precision X-ray Inc.). The cells were washed with PBS and fresh media was added to the wells 1 hour after irradiation. MTT assay was performed according to the established protocol 24 hours following irradiation.

Figure 27A:
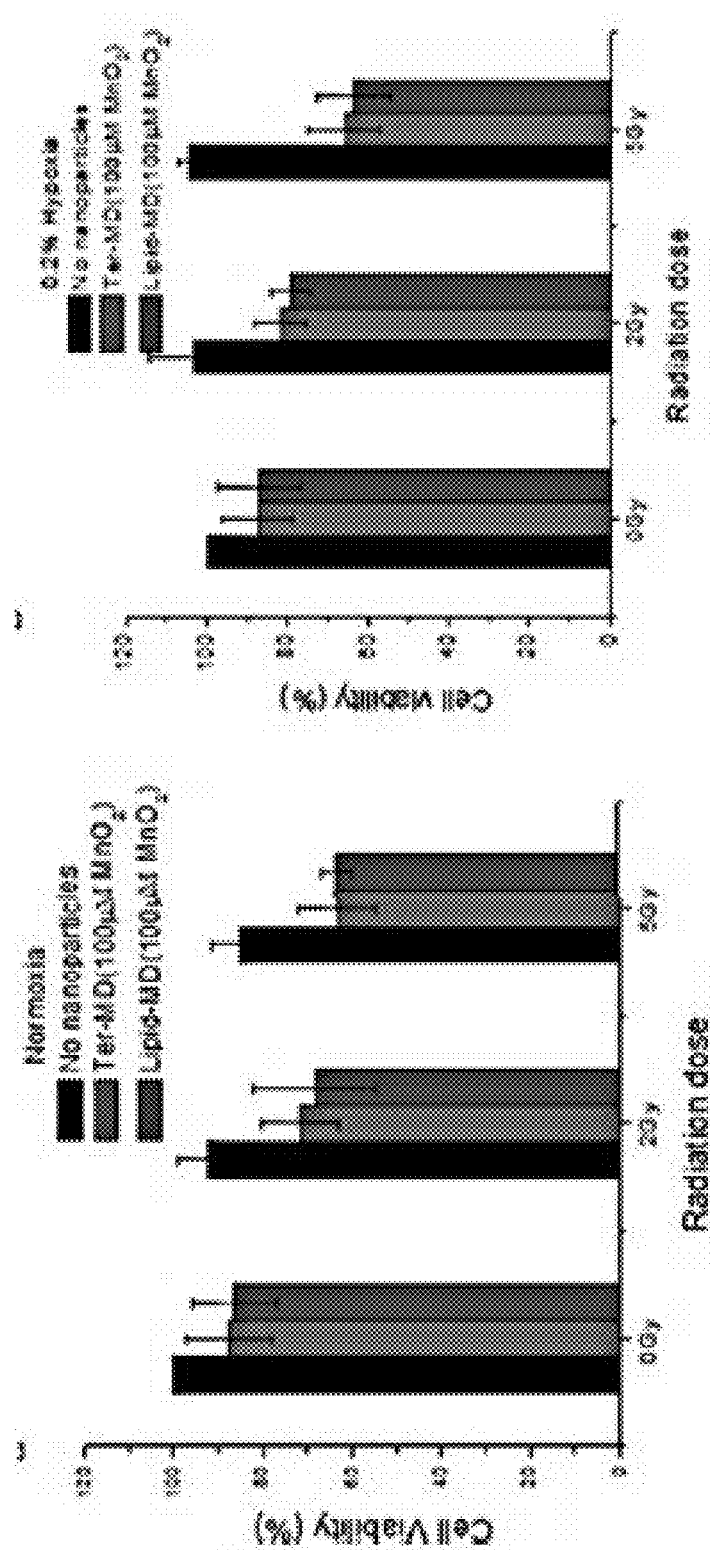
FIG. 27 shows the effects of L-MD NPs on human prostate cancer cells in vitro (a) and in vivo (b). (a) Graphical representation of cell viability data obtained following treatment of PC3 human prostate cells with saline control, TER-MD NPs, or L-MD NPs under normoxic (left) and hypoxic (right) conditions and following radiation.

In normoxia, PC-3 exhibited moderate radiosensitivity as reported in literature; on the other hand, exposure to hypoxia (0.2% $O_2$ for 18 hours) resulted in radioresistance (up to 5 Gy) (FIG. 27a). In all irradiated groups, cells that were treated with MD NPs showed lower viability compared to the cells without the MD NPs, demonstrating the radiosensitizing effect of the MD NPs. There were no significant differences in cellular response to TER-MD and L-MD (FIG. 27a). Notably, radioresistant (hypoxic) cells exposed to MD NPs treatment were sensitive to irradiation (60% cell viability with 5 Gy irradiation), suggesting that the MD NPs could overcome cellular radioresistance induced by hypoxia. Data were normalized to the control group (0 Gy, no nanoparticles) for both normoxia and hypoxia group.

Human PC-3 prostate tumors were established by subcutaneous injection of 2×10$^6$PC-3 cells at abdominal side of SCID mice. After about four weeks, when tumor volume reached ~100 mm$^3$, the mice were divided into 2 groups: 1) Saline+RT and 2) L-MD NP+RT and the treatments were initiated. The mice were restrained in a specially designed box of acrylic polymer, and the tumors were irradiated locally at 10 Gy, 30 min after i.t administration 50 uL of saline (control) or 1 mM MD NPs in saline. The tumor size was measured with a Vernier caliper in two dimensions and tumor volumes were calculated by the formula V=[(length)× (width)$^2$]/2. At the end of experiment, the animals were sacrificed and the tumor masses were excised and weighed. Tumor tissue was fixed in formalin and H&E stained to determine percent necrosis.

Figure 27B:
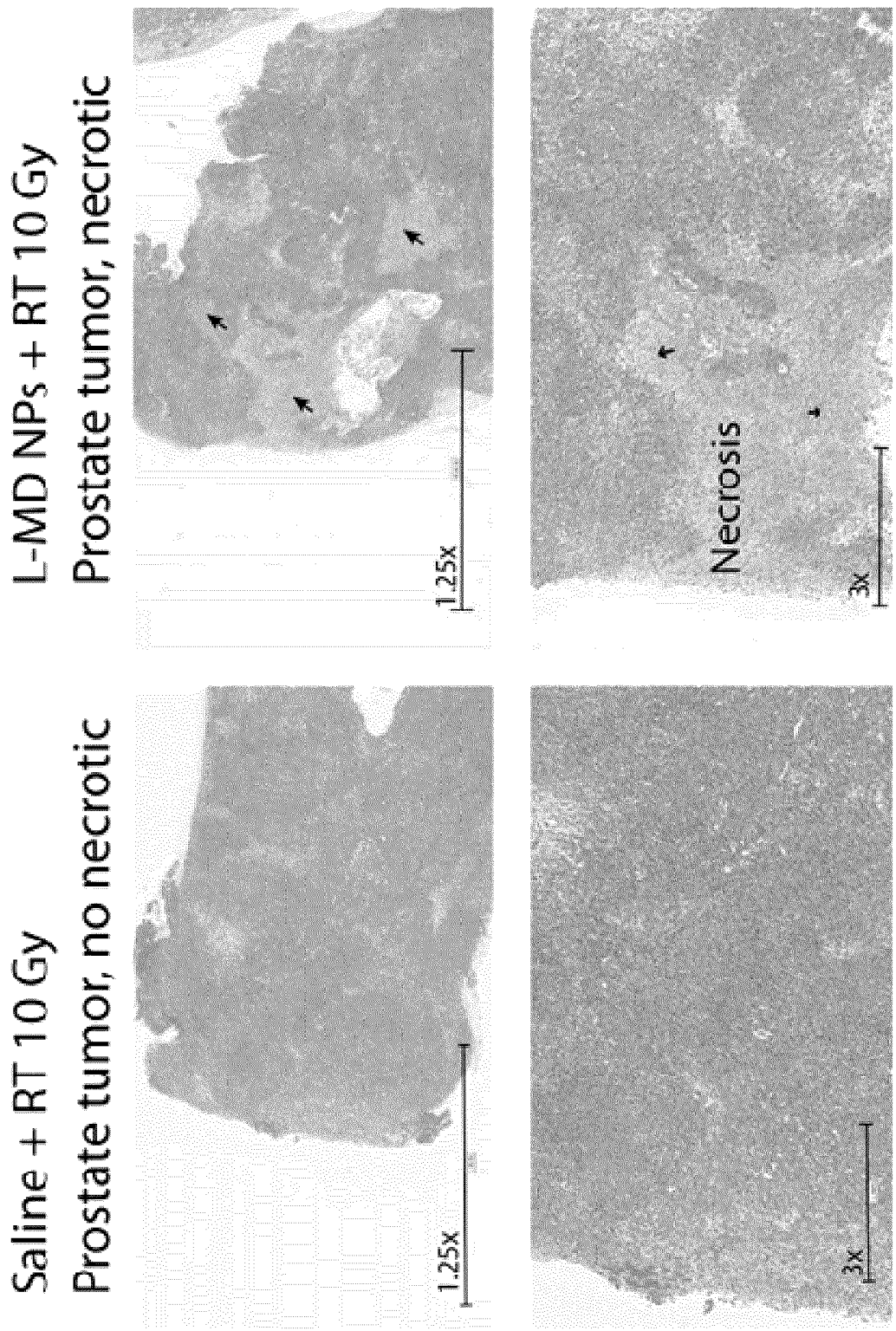

Histopathology analysis of resected tumor tissue revealed that the combination of the L-MD NPs with irradiation led to significant increase in tumor necrosis as compared to the control group. Tumors treated with L-MD NPs+RT at a single dose of 10 Gy showed significant tumor necrosis, while the tumors in the saline+RT group showed no histological evidence of necrosis 5 days post-treatment (FIG. 27b).

Figure 27C:
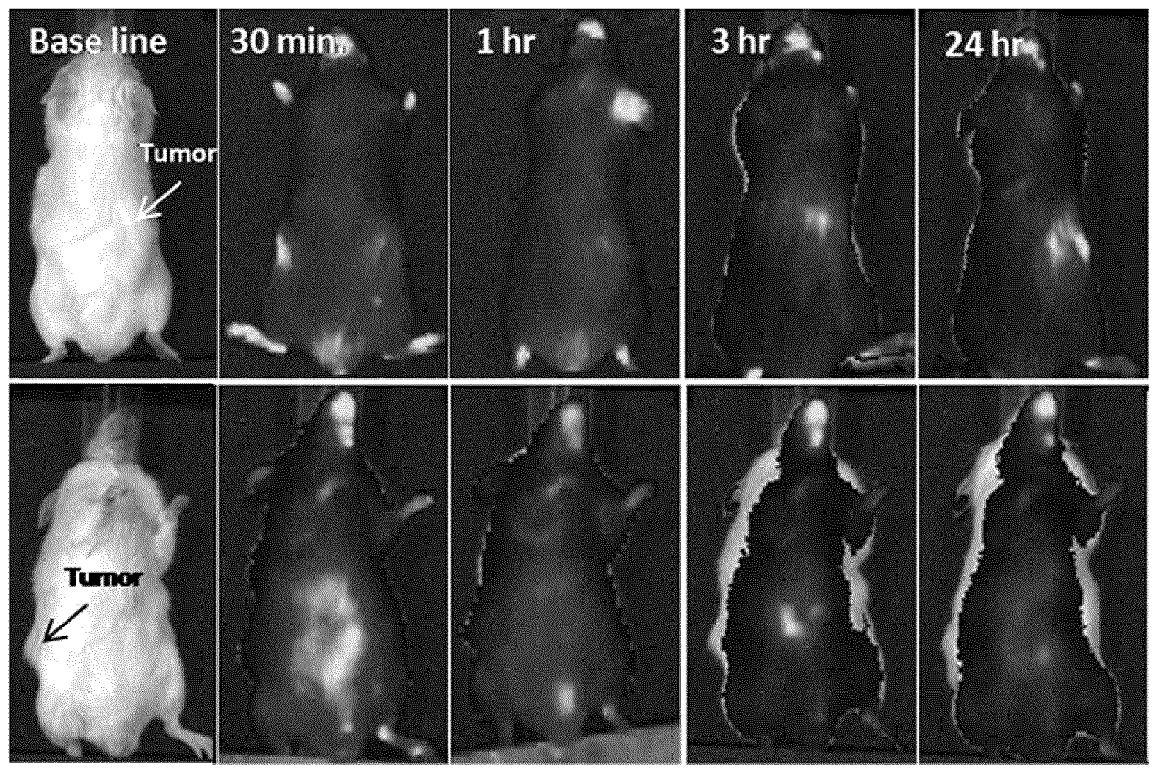
Figure 27D:
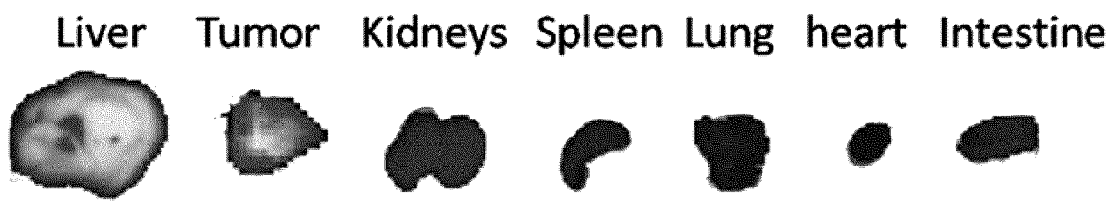

The in vivo biodistribution and tumor accumulation ability of L-MD nanoparticles was determined using human PC3-grafted SCID male mice. In detail, once the tumor reached a volume of 400-500 mm$^3$, 100 µL of L-MD nanoparticles (1 mM $MnO_2$ based on ICP analysis) synthesized by co-loading the hydrophobic near infrared dye indocyanine green was injected intravenously. Mice were anaesthetized with isoflurane and at different time points, whole body fluorescence images were acquired using 745 nm excitation and 820 nm emission filter under Xenogen IVIS Spectrum Imaging System (Caliper Life Sciences Inc., USA). Biodistribution of L-MD nanoparticles using ex vivo analysis was also determined. For ex vivo biodistribution studies, animals were euthanized and different organs collected 24 hours post-nanoparticle injection. Ex vivo fluorescence images of organs were then obtained using the Xenogen IVIS Spectrum Imaging System using 745 nm excitation and 820 emission filter. From whole body real-time imaging, tumor uptake of L-MD nanoparticles was easily determined, and 24 hours post-injection, tumor was easily delineated from the surrounding healthy tissue (FIG. 27c). The ex vivo optical data of excised tissue showed a significant uptake of L-MD nanoparticles by tumor 24 hours post-particle administration (FIG. 27d). In FIGS. 27c and 27d, lighter shade indicates higher fluorescence emission.

REFERENCES

1. Gatenby, R. A.; Gillies, R. J. A Microenvironmental Model of Carcinogenesis. *Nat. Rev. Cancer.* 2008, 8, 56-61.
2. Rockwell, S.; Dobrucki. I. T.; Kim, E. Y.; Marrison, S. T.; Vu, V. T. Hypoxia and Radiation Therapy: Past History, Ongoing Research, and Future Promise. *Curr. Mol. Med.* 2009, 9, 442-458.
3. Lundgren, K.; Holm, C.; Landberg, G. Hypoxia and Breast Cancer: Prognostic and Therapeutic Implications. *Cell. Mol. Life Sci.* 2007, 64, 3233-3247.
4. Chan N, Milosevic M and Bristow R G. Tumor hypoxia, DNA repair and prostate cancer progression: new targets and new therapies. Future Oncol 3(3): 329-41, 2007.

5. Vaupel, P.; Schlenger, K.; Knoop, C.; Hockel, M. Oxygenation of Human Tumors: Evaluation of Tissue Oxygen Distribution in Breast Cancers by Computerized $O_2$ Tension Measurements. *Cancer Res.* 1991, 51, 3316-3322.
6. Bertout, J. A.; Patel, S. A.; Simon, M. C. The Impact of $O_2$ Availability on Human Cancer. *Nat. Rev. Cancer,* 2008, 8, 967-975.
7. Rademakers, S. E.; Span, P. N.; Kaanders, J. H.; Sweep, F. C.; van der Kogel, A. J.; Bussink, J. Molecular Aspects of Tumour Hypoxia. *Mol Oncol.* 2008, 2, 41-53.
8. Semenza, G. Hypoxia-Inducible Factors: Mediators of Cancer Progression and Targets of Cancer Therapy. *Trends Pharmacol. Sci.* 2012, 33, 207-214.
9. Liao, D.; Johnson, R. S. Hypoxia: A Key Regulator of Angiogenesis in Cancer. *Cancer Metastasis Rev.* 2007, 26, 281-290.
10. Forsythe, J. A.; Jiang, B. H.; Iyer, N. V.; Agani, F.; Leung, S. W.; Koos, R. D.; Semenza, G. L. Activation of Vascular Endothelial Growth Factor Gene Transcription by Hypoxia-Inducible Factor 1. *Mol Cell Biol.* 1996, 16, 4604-4613.
11. Gatenby, R. A.; Gillies, R. J. Why Do Cancers Have High Aerobic Glycolysis? *Nat. Rev. Cancer.* 2004, 4, 891-899.
12. Chiche, J.; Brahimi-Horn, M. C.; Pouysségur, J. Tumour Hypoxia Induces a Metabolic Shift Causing Acidosis: A Common Feature In Cancer. *J. Cell Mol. Med.* 2010, 14, 771-794.
13. López-Lázaro, M. Dual Role of Hydrogen Peroxide in Cancer: Possible Relevance to Cancer Chemoprovention and Therapy. *Cancer Lett.* 2007, 252, 1-8.
14. Chung-Pu Wu, Chia-Hung Hsieh, Yu-Shan Wu, The emergence of drug transporter-mediated multidrug resistance to cancer chemotherapy, Mol. Pharmaceutics 2011, 8, 1996-2011.
15. Deng L., Lin-Lee Y. C., Claret F. X., Kuo M. T., 2-acetylaminofluorene up-regulates rat mdr1b expression through generating reactive oxygen species that activate NF-kappa B pathway. J. Biol. Chem. 2001, 276 (1), 413-20.
16. Watenberg M., Ling F. C., Sauer H., Down-regulation of intrinsic P-glycoprotein expression in multicellular prostate tumor spheroids by reactive oxygen species. J. Biol. Chem., 2001, 276 (20) 17420-8.
17. Gerwek L. E., Vijayappa S., Kozin S., Tumor pH controls the in vivo efficacy of weak acid and base chemotherapeutics. Mol. Cancer Ther. 2006, 5 (5), 1275-9.
18. Calcinotto A. et al. Modulation of Microenvironment Acidity Reverses Anergy in Human and Murine Tumor-Infiltrating T Lymphocytes. Cancer Res; 72(11), 2012, OF1-OF11.
19. Fischer B., Muller B., Fischer K. G., Baur N., Kreutz W. (2000). Acidic pH inhibits non-MHC-restricted killer cell functions. Clin. Immunol. 96, 252-263.
20. Bradley M. Tebo, J. R. B., Brian G. Clement, Gregory J. Dick, Karen J. Murray, Dorothy Parker, Rebecca Verity, Samuel M. Webb BIOGENIC MANGANESE OXIDES: Properties and Mechanisms of Formation. *Annual Reviews Earth and Planetary Sciences* 32, 287-328 (2004).
21. Michael P. Lisanti, Ubaldo E. Martinez-Outschoom, Zhao Lin, Stephanos Pavlides, Diana Whitaker-Menezes, Richard G. Pestell, Anthony Howell, Federica Sotgia. Hydrogen peroxide fuels aging, inflammation, cancer metabolism and metastasis. Cell Cycle 10:15, 2440-2449; 2011.
22. Hellman, S. Principles of Cancer Management: Radiation Therapy. In Principles & Practice of Oncology; Devita Jr, V. T., Hellman, S., Rosenberg, S. A., Eds.; Fifth edition. Philadelphia: Lippincott-Raven Publishers, 1997; pp 307-331.
23. Wu, W.; Yang, Q.; Li, T.; Zhang, P.; Zhou, R.; Yang, C. Hemoglobin-Based Oxygen Carriers Combined with Anticancer Drugs May Enhance Sensitivity of Radiotherapy and Chemotherapy to Solid Tumors. *Artif. Cells Blood Substit. Immobil. Biotechnol.* 2009, 37, 163-165.
24. Overgaard, J.; Horsman, M. R. Modification of Hypoxia Induced Radioresistance in Tumors by the Use of Oxygen and Sensitizers. *Semin. Radiat. Oncol.* 1996, 10-12.
25. Gordijo, C. R.; Shuhendler, A. J.; Wu, X. Y. Glucose-Responsive Bio-Inorganic Nanohybrid Membrane oor Self-Regulated Insulin Release. *Adv. Func. Mater.* 2010, 20, 1404-1412.
26. Luo, X. L.; Xu, J. J.; Zhao, W.; Chen, H. Y. A Novel Glucose ENFET Based on the Special Reactivity of $MnO_2$ Nanoparticles. *Biosens. Biolectron.* 2004, 19, 1295-1300.
27. Yildirimer, L.; Thanh, N. T. K.; Loizidou, M; Seifalian, A. M. Toxicological Considerations of Clinically Applicable Nanoparticles. *Nano Today.* 2011, 6, 585-607.
28. Bai, Y.; Du, Y.; Xu, J. Choline Biosensors Based on a Bi-Electrocatalytic Property of $MnO_2$ Nanoparticles Modified Electrodes to $H_2O_2$. *Electrochem. Commun.* 2007, 9, 2611-2616.
29. Liu, X.; Wang, Q.; Zhao, H.; Zhang, L.; Su, Y.; Lv, Y. BSA-Templated $MnO_2$ Nanoparticles as Both Peroxidase and Oxidase Mimics. *Analyst* 2012, 137, 4552-4558.
30. Luo, Y. Preparation of $MnO_2$ Nanoparticles by Directly Mixing Potassium Permanganate and Polyelectrolyte Aqueous Solutions. *Mater. Lett.* 2007, 61, 1893-1895.
31. Kaibara, K.; Okazaki, T.; Bohidar, H. B.; Dubin, P. L. pH-Induced Coacervation in Complexes of Bovine Serum Albumin and Cationic Polyelectrolytes. *Biomacromolecules* 2000, 1, 100-107.
32. Alkilany, A. M.; Nagaria, P. K.; Hexel, C. R.; Shaw, T. J.; Murphy, C. J.; Wyatt, M. D. Cellular Uptake and Cytotoxicity of Gold Nanorods: Molecular Origin of Cytotoxicity and Surface Effects. *Small* 2009, 5, 701-708.
33. Halliwell, B.; Clement, M. V.; Long, L. H. Hydrogen Peroxide in The Human Body. *FEBS Letters* 2000, 486, 10-13.
34. Wojtkowiak, J. W.; Verduzco, D.; Schramm, K. J.; Gillies, R. J. Drug Resistance and Cellular Adaptation to Tumor Acidic pH Microenvironment. *Mol. Pharmaceutics* 2011, 8, 2032-2038.
35. Desai, N. Nab Technology: A Drug Delivery Platform Utilizing Endothelial Gp60 Receptor-Based Transport and Tumour-Derived SPARC for Targeting. *Drug Delivery Report* 16th edition. 2007, 37-41.
36. Desai, N. Nanoparticle Albumin Bound (Nab) Technology: Targeting Tumors through the Endothelial Gp60 Receptor and SPARC. *Nanomedicine: Nanotechnology, Biology and Medicine* 2007, 3, 339.
37. Desai, N.; Trieu, V.; Damascelli, B.; Soon-Shiong, P. SPARC Expression Correlates with Tumor Response to Albumin-Bound Paclitaxel in Head and Neck Cancer Patients. *Transl. Oncol.* 2009, 2, 59-64.
38. Desai, N., Trieu, V.; Yao, Z., Louie, L.; Ci, S.; Yang, A.; Tao, C.; De, T.; Beals, B.; Dykes, D.; et al. Increased Antitumor Activity, Intratumor Paclitaxel Concentrations, and Endothelial Cell Transport of Cremophor-Free, Albumin-Bound Paclitaxel, ABI-007, Compared with Cremophor-Based Paclitaxel. *Clin. Cancer Res.* 2006, 12, 1317-1324.
39. Zhang, H. F.; Maslov, K.; Stoica, G.; Wang, L. V. Functional Photoacoustic Microscopy for High Resolution and Noninvasive In Vivo Imaging. *Nat. Biotech.* 2006, 34, 848-851.
40. Fukumura. D.; Duda, D. G.; Munn, L. L.; Jain, R. K. Tumor Microvasculature and Microenvironment: Novel Insights through Intravital Imaging in Pre-Clinical Models. *Microcirculation* 2010, 17, 206-225.
41. Goldberg, E. P.; Hadba, A. R.; Almond, B. A.; Marotta, J. S. Intratumoral Cancer Chemotherapy and Immunotherapy: Opportunities for Nonsystemic Preoperative Drug Delivery. *J. Pharm. Pharmacol.* 2002, 54, 159-180.
42. Yang, L.; Wang, B.; Qiao, W.; Liu, P. A Novel Combination Chemotherapy Integrating with Intratumoral Chemotherapy. *Med. Hypotheses* 2009, 73, 334-335.
43. Hight, M. R.; Nolting, D. D.; McKinley, E. T.; Lander, A. D.; Wyatt, S. K.; Gonyea, M.; Zhao, P.; Manning, H. C. Multispectral Fluorescence Imaging to Assess pH in Biological Specimens. *J. Biomed. Opt.* 2011, 16, 0160071-7.
44. Kalliomaki, T.; Hill, R. P. Effects of Tumour Acidification with Glucose+MIBG on the Spontaneous Metastatic Potential of Two Murine Cell Lines. *Brit. J. Cancer* 2004, 90, 1842-1849.
45. Gillies, R. J.; Raghunand, N.; Garcia-Martin, M. L.; Gatenby, R. A. pH Imaging—A Review of pH Measurement Methods and Applications in Cancers. *IEEE Eng. Med. Biol. Mag.* 2004, 23, 57-64.
46. Peyratout, C. S.; Dahne, L. Tailor-Made Polyelectrolyte Microcapsules: From Multilayers to Smart Containers. *Angew. Chem. Int. Ed.* 2004, 43, 3762-3783.
47. Rivera-Gill, P.; De Koker, S.; De Geest, B. G.; Parak, W. J. Intracellular Processing of Proteins Mediated by Biodegradable Polyelectrolyte Capsules. *ACS Nano.* 2009, 9, 4398-4402.
48. Rademakers, S. E.; Lok, J.; van der Kogel, A. J.; Bussink, J.; Kaanders, J. H. Metabolic Markers in Relation to Hypoxia; Staining Patterns and Colocalization of Pimonidazole, HIF-1α, CAIX, LDH-5, GLUT-1, MCT1 And MCT4. *BMC Cancer.* 2011, 11, 167-177.
49. Wu, H.; Huang, C.; Chang, D. Anti-Angiogenic Therapeutic Drugs for Treatment of Human Cancer. *J. Cancer Mol.* 2008, 4, 37-45.
50. Carmeliet, P.; Jain, R. K. Angiogenesis in Cancer and Other Diseases, *Nature* 2000, 407, 249-257.
51. Moroz, E.; Carlin, S.; Dyomina, K.; Burke, S.; Thaler, H. T.; Blasberg, R.; Serganova, I.; Real Time Imaging of HIF-1α Stabilization and Degradation. *PLoS ONE.* 2009, 4, e5077 1-13
52. Emil, M.; Simon, M.; Aashish, S.; George, I. DNA Double-Strand Break Repair as Determinant of Cellular Radiosensitivity to Killing and Target in Radiation Therapy. *Front. Oncol.* 2013, 1-18.
53. Maeda, A.; Leung, M. K. K.; Conroy, L.; Chen, Y.; Bu, J et al. In Vivo Optical Imaging of Tumor and Microvascular Response to Ionizing Radiation. *PLoS ONE.* 2012, 7, e42133 1-15.
54. Shalviri, A.; Raval, G.; Prasad, P.; Chan, C.; Liu, Q.; Heerklotz, H.; Rauth, A. M.; Wu, X. Y. pH-Dependent Doxorubicin Release from Terpolymer of Starch, Polymethacrylic Acid and Polysorbate 80 Nanoparticles for Overcoming Multi-Drug Resistance in Human Breast Cancer Cells. *Eur. J. Pharm. Biopharm.* 2012, 82, 587-597.
55. Zhang, F.; Ali, Z.; Amin, F.; Feltz, A.; Oheim, M.; Parak, W. J. Ion and pH Sensing with Colloidal Nanoparticles: Influence of Surface Charge on Sensing and Colloidal Properties. *Chemphyschem.* 2010, 11, 730-735.
56. del Mercato, L. L.; Abbasi, A. Z.; Parak, W. J. Synthesis and Characterization af Ratiometric Ion-Sensitive Polyelectrolyte Capsules. *Small* 2011, 7, 351-363.
57. Alireza Shalviri, Ho Ka Chan, Gaurav Raval, Mohammad J Abdekhodaie, Qiang Liu, Heiko Heerklotz, Xiao Yu Wu, Design of pH-responsive nanoparticles of terpolymer of poly(methacrylic acid), polysorbate 80 and starch for delivery of doxorubicin. Colloids and surfaces B: Biointerfaces (2012) 101C:405-413.

We claim:

1. A method of enhancing a radiation directed to a tissue or a tumor in a subject comprising the steps of:
    (a) reducing hypoxia in the tissue or tumor by producing oxygen in the tissue or tumor by administering an amount of a multifunctional nanoparticle composition to the subject, the multifunctional nanoparticle composition comprising a matrix having multiple coated nanoparticles that react with $H_2O_2$ present in the tissue or tumor to produce $O_2$ in the tissue or tumor, each coated nanoparticle comprising a metal oxide nanoparticle precursor stabilized by a positively charged polyelectrolyte, and a functional coating on a surface of the metal oxide nanoparticle precursor, and
    (b) applying radiation to the subject,
    wherein the production of oxygen in the tissue or tumor combines with the radiation to make DNA damage in the tissue or tumor permanent thereby the radiation is enhanced in the subject.

2. The method of claim 1, wherein the matrix is selected from the group consisting of organic groups, inorganic compounds, proteins, nucleic acids, polymers, lipids and mixtures thereof.

3. The method of claim 1, wherein each coated nanoparticle further comprises a functional moiety, the functional moiety being selected from the group consisting of a targeting moiety, a detectable moiety, a radioisotope, a radionuclide and mixtures thereof.

4. The method of claim 1, wherein each metal oxide nanoparticle is a manganese dioxide nanoparticle.

5. The method of claim 1, wherein the positively charged electrolyte is poly(allylamine hydrochloride) (PAH).

6. The method of claim 5, wherein the matrix comprises albumin, a graft terpolymer (TER), a polyoxyethylene stearate (lipid-PEG), a lipid or a grafted amphiphilic polymer (PMA).

7. The method of claim 6, wherein:
    (a) the matrix comprises the albumin, the coated nanoparticles are manganese dioxide nanoparticles (MD NP) and the multifunctional nanoparticle composition is albumin-MD NP; or
    (b) the matrix comprises the TER, and the multifunctional nanoparticle composition is TER-MD NP; or
    (c) the matrix comprises the lipid-PEG having a chain of about 2 kDa to about 10 kDa, and wherein the multifunctional nanoparticle composition is a PEG-TER-MD NP; or
    (d) the matrix comprises the lipid, and the lipid matrix comprises a myristic acid and a lipid-PEG, and wherein the multifunctional nanoparticle composition is lipid-MD NP; or (e) the matrix comprises the PMA, the PMA is a poly(isobutylene-alt-maleic anhydride-hexadeylamine), and wherein the multifunctional nanoparticle composition is PMA-MD NP.

8. The method of claim 7, wherein the albumin-MD NP is about 20 nm to about 1000 nm in diameter, the TER-MD NP is about 50 nm to about 1000 nm in diameter, the PEG-TER-MD NP is about 50 nm to about 1000 nm in diameter, L-MD NP is about 50 nm to about 1000 nm in diameter and the PMA-MD NP is about 50 nm to about 1000 nm in diameter.

9. The method of claim 1, wherein the multifunctional nanoparticle composition is negatively charged.

10. The method of claim 1, wherein each coated nanoparticle embedded in the matrix has a mean particle size of 10 nm to 1000 nm.

11. The method of claim 1, wherein the metal oxide is selected from the group consisting of $MnO_2$, $Mn_2O_3$, $Mn_2O_7$, $MnOOH$, $Mn_3O_4$, $Mn(C_2O_4)$, $MgO$, $NiO_2$, $Co_3O_4$, $AgO$, $CuO$, $BiO$, $Rb_2O$, $In_2O$, $Tl_2O_3$, $Cs_2O$, and $HfO_2$.

12. The method of claim 1, wherein the administration is intratumoral, peritumoral, or intravenous injection.

13. The method of claim 1, wherein the step of administering the composition is prior to the step of applying the radiation.

14. The method of claim 1, wherein the composition is intravenously injected to the subject about 1 to about 24 hours prior to the radiation.

15. The method of claim 1, wherein the composition is intratumorally injected to the subject about 5 minutes to about 3 hours prior to the radiation.

16. The method of claim 1, wherein the method is for treating a cancer in the subject.

* * * * *